US007595308B2

(12) United States Patent
Friedman et al.

(10) Patent No.: US 7,595,308 B2
(45) Date of Patent: Sep. 29, 2009

(54) COMPOSITIONS FOR TREATING AND/OR PREVENTING DISEASES CHARACTERIZED BY THE PRESENCE OF METAL IONS

(75) Inventors: Orrie Friedman, Brookline, MA (US); Ivan Correia, Winchester, MA (US); Toby Sommer, Waltham, MA (US); David Alan Kew, Worcester, MA (US)

(73) Assignee: GrenPharma LLC, Waltham, MA (US)

( * ) Notice: Subject to any disclaimer, the term of this patent is extended or adjusted under 35 U.S.C. 154(b) by 180 days.

(21) Appl. No.: 11/132,170

(22) Filed: May 17, 2005

(65) Prior Publication Data

US 2006/0040897 A1    Feb. 23, 2006

Related U.S. Application Data

(63) Continuation-in-part of application No. PCT/US03/37037, filed on Nov. 18, 2003.

(60) Provisional application No. 60/427,105, filed on Nov. 18, 2002, provisional application No. 60/427,104, filed on Nov. 18, 2002, provisional application No. 60/427,201, filed on Nov. 18, 2002, provisional application No. 60/427,203, filed on Nov. 18, 2002, provisional application No. 60/456,345, filed on Mar. 20, 2003, provisional application No. 60/576,425, filed on May 27, 2004, provisional application No. 60/621,481, filed on Oct. 22, 2004.

(51) Int. Cl.
*A01N 55/00* (2006.01)
(52) U.S. Cl. .......................................... 514/63; 514/879
(58) Field of Classification Search .................. 514/63, 514/879
See application file for complete search history.

(56) References Cited

U.S. PATENT DOCUMENTS

| | | | |
|---|---|---|---|
| 4,006,226 A | 2/1977 | Bennett | |
| 4,039,666 A | 8/1977 | Chandler et al. | |
| 5,242,932 A | 9/1993 | Gandy et al. | |
| 5,384,312 A | 1/1995 | Schirlin et al. | |
| 5,385,915 A | 1/1995 | Buxbaum et al. | |
| 5,523,295 A | 6/1996 | Fasman | |
| 5,529,988 A | 6/1996 | Schirlin et al. | |
| 5,532,397 A | 7/1996 | Schirlin et al. | |
| 5,854,215 A | 12/1998 | Findeis et al. | |
| 5,859,277 A | 1/1999 | Whitlock et al. | |
| 6,001,389 A | 12/1999 | Seguin et al. | |
| 6,172,250 B1 | 1/2001 | Seguin et al. | |
| 6,211,393 B1 | 4/2001 | Seguin et al. | |
| 2003/0050272 A1 | 3/2003 | Taylor et al. | |
| 2005/0020541 A1 | 1/2005 | Tacke et al. | |

FOREIGN PATENT DOCUMENTS

| EP | 0273266 A2 | 7/1988 |
|---|---|---|
| EP | 0877027 A2 | 11/1998 |
| FR | 2645863 A1 | 10/1990 |
| WO | WO 2004/045552 | 6/2004 |

OTHER PUBLICATIONS

Barclay, L. "Antibodies Targeting Amyloid-Beta May Be Helpful in Alzheimer's Disease", Jul. 20, 2006, Medscape Medical News, pp. 1-4.*
Birchall, J., et al., "Biological implications of the interaction (via silanol groups) of silicon with metal ions," *US National Library of Medicine*, XP002370605 (1986) (Abstract).
International Search Report and Written Opinion dated Mar. 30, 2006 from International Application No. PCT/2005/038304, filed Oct. 24, 2005.
Tacke, R. et al., "Sila-substitution—a useful strategy for drug design?" *Endeavor, New Series* 1988, 10(4), 191-197.
Tacke, R. et al., "Syntheses and Properties of Bioactive Organo-Silicon Compounds," *Topics in Current Chemistry*, 1979, 84,1-75.
Amberla, K., et al., "Long-term treatment with tacrine (THA) in Alzheimer's Disease—evaluation of neuropsychological data," *Acta Neural Scand*, vol. 149, pp. 55-57 (1993).
Amorphous Silica, in Kirk-Othmer Encyclopedia of Chemical Technology, Third Edition, vol. 20, Ed. H. F. Mark et al., John Wiley & Sons, New York, pp. 768-770 (1982).
Armstrong, C., et al., "Comparative effects of metal chelating agents on the neuronal cytotoxicity induced by copper ($Cu^{+2}$), iron ($Fe^{+3}$) and zinc in the hippocampus," Brain Research, vol. 892, pp. 51-62 (2001).

(Continued)

*Primary Examiner*—Sreeni Padmanabhan
*Assistant Examiner*—Kendra D Carter
(74) *Attorney, Agent, or Firm*—Wolf, Greenfield & Sacks, P.C.

(57) ABSTRACT

The present invention generally relates to the treatment and/or prevention of Alzheimer's disease, other neurodegenerative diseases, and/or diseases characterized by the presence of certain metal ions, by using certain compositions including organosilicon compounds. A composition of the invention may be administered to a mammal, such as a human. In some cases, the composition may include a silanol, a silandiol, a silantriol, or a cyclic organosilane, and/or be able to form a silanol, a silandiol, or a silantriol upon exposure to physiological conditions such as are found in the blood, in the stomach and/or gastrointestinal tract, or in the brain or other organ. In certain cases, the organosilicon compound may be bound to a moiety able to be transported across the blood-brain barrier into the brain, for example, an amino acid, a peptide, a protein, a virus, etc. The organosilicon compound may also be labeled (e.g., fluorescently or radioactively) in certain instances. In some embodiments, the composition, or a portion thereof, may sequester aluminum, copper, iron or other ions, for example, by electrostatically binding to the ions. The composition may also include other functionalities such as amines, certain alkyl and/or aryl moieties (including substituted alkyls and/or aryls), or hydrophobic moieties, for example, to facilitate transport of the organosilicon compound through the blood-brain barrier.

2 Claims, 40 Drawing Sheets

OTHER PUBLICATIONS

Banin, E., et al., "Toxic Effects of Alumino-Silicates on Nerve Cells," *Neuroscience*, vol. 39, No. 1, pp. 171-178 (1990).

Berthon, G., "Relevance of aluminium-acid complex equilibria," *Metal Ions in Biology and Medicine*, vol. 2, pp. 253-258 (1992).

Birchall, J. D., "Acute toxicity of aluminium to fish eliminated in silicon-rich acid waters," *Nature*, vol. 338, pp. 146-148 (1989).

Birchall, J. D., "The Solution Chemistry of Aluminium and Silicon and Its Biological Significance," *Imperial Chemical Industries*, pp. 231-242, (1988).

Birchall, J. D., et al., "The Chemistry of Aluminum and Silicon in Relation to Alzheimer's Disease," *Clinical Chemistry*, vol. 34, No. 2, pp. 265-267 (1988).

Birchall, J. D., "The Toxicity of Aluminium and the Effect of Silicon on its Bioavailability", *Aluminium in Chem. Biol. and Med.*, 1:53-69(1991) (I).

Brichall, J. D., et al., "Aluminium, Water Chemistry and Alzheimer's Disease," *The Lancet*, pp. 953 (1989).

Bush, A. I., "Metal complexing agents as the therapies for Alzheimer's disease," *Neurobiology of Aging*, vol. 23, pp. 1031-1038 (2002).

Bush, A.I., "Metals and neuroscience," *Current Opinion in Chemical Biology*, vol. 4, pp. 184-191 (2000).

Bush, A.I., "The metallobiology of Alzheimer's disease," *TRENDS in Neurosciences*, vol. 26, pp. 207-214 (2003).

Campbell, A., et al., "Mechanisms by which metals promote events connected to neurodegenerative diseases," *Brain Research Bulletin*, vol. 55, No. 2, pp. 125-132 (2001).

Carlisle, E. M., "Effect of Dietary Silicon and Aluminum on Silicon and Aluminum Levels in Rat Brain," *Alzheimer Disease and Associated Disorders*, vol. 1, No. 2, pp. 83-89 (1987).

Cherny, R. A., et al., "Chelation and Intercalation: Complementary Properties in a Compound for the Treatment of Alzheimer's Disease," *Journal of Structural Biology*, vol. 130, pp. 209-216 (2000).

Cherny, R. A., et al., "Treatment with a Copper-Zinc Chelator Markedly and Rapidly inhibits β-Amyloid Accumulation in Alzheimer's Disease Transgenic Mice," *Neuron*, vol. 30, pp. 665-676 (2001).

Crompton, D. E., et al., "Neuroferritinopathy: A Window on the Role of Iron in Neurodegeneration," *Blood Cells, Molecules and Diseases*, vol. 29, No. 3, pp. 522-531 (2002).

Cui, Z., et al., "Novel D-penicillamine carrying nanoparticles for metal chelation therapy in Alzheimer's and other CNS diseases," *European Journal of Pharmaceutics and Biopharmaceutics*, vol. 59, pp. 263-272 (2005).

Dedeoglu, A., et al., "Preliminary studies of a novel bifunctional metal chelator targeting Alzheimer's amyloidogenesis," *Experimental Gerontology*, vol. 39, pp. 1641-1649 (2004).

Dobbie, J.W., et al., "Urinary and serum silicon in normal and uraemic individuals," *Silicon Biochemistry*.

Doll, S.R., "Review: Alzheimer's Disease and Environmental Aluminium," *Age and Ageing*, vol. 22, pp. 138-153 (1993).

Edwardson, J.A., et al., "Aluminosilicates and the ageing brain: implications for the pathogenesis of Alzheimer's diseas," *Silicon Biochemistry*, pp. 160-179 (1986).

Edwardson, J.A., et al., "Effect of silicon on gastrointestinal absorption of aluminium," *The Lancet*, vol. 342, pp. 211-212 (1993).

Eichhorn, G.L., "Is there any relationship between Aluminum and Alzheimer's Disease?", *Experimental Gerontology*, vol. 28, pp. 493-498 (1993).

Epstein, S. G., "Aluminum Intake and Its Effects," *The Aluminum Association, Inc.*, pp. 189-200.

Fasman, G. D., et al., "Solubilization of β-amyloid-(1-42)-peptide: Reversing the β-sheet conformation induced by aluminum with silicates," *Proc. Natl., Acad. Sci.*, vol. 92, pp. 369-371 (1995).

Fasman, G.D., et al., "The solubilization of model Alzheimer tangles: Reversing the β-sheet conformation induced by aluminum with silicates," *Proc. Natl. Acad. Sci.*, vol. 91, pp. 11232-11235 (1994).

Flaten, T. P., "Geographical Associations between Aluminium in Drinking Water and Registered Death Rates with Dementia (including Alzheimer's Disease) in Norway," *Department of Chemistry, University of Trodheim*, pp. 245-256, (1990).

Garzon-Rodriguez, W., et al., "Binding of ZN(II), CU(II), and FE(II) Ions to Alzheimer's Ab Peptide Studies by Fluorescence," *Bioorganic & Medicinal Chemistry Letters*, vol. 9, pp. 2243-2248 (1999).

Gillette-Guyonnet, S., et al., "Cognitive impairment and composition of drinking water in women: findings of the EPIDOS Study," *Am. J. Clin. Nutr.*, vol. 81, pp. 897-902 (2005).

Goedert, M., et al., "Neurofibrillary tangles and β-amyloid deposits in Alzheimer's disease," *Current Biology, Ltd.*, vol. 1, pp. 441-447 (1991).

Good, P.F., et al., "Selective Accumulation of Aluminum and Iron in the Neurofibrillary Tangles of Alzheimer's Disease: A Laser Microprobe (LAMMA) Study," *American Neurological Association*, vol. 31, No. 3, pp. 286-292 (1992).

Hanin, I., "A Survey of Current Treatment Strategies in Alzheimer's Disease," *Drugs in Development*, vol. 2, pp. 195-200 (1993).

Hench, L. L., et al, "Biocompatibility of silicates for medical use," *Bioglass Research Center*, pp. 231-246(1986).

Henig, R. M., "Is Misplacing Your Glasses Alzheimer's?," *New York Times*, Apr. 24, 1994, pp. 72-76 (1994).

Hollosi, M., "Stable intrachain and interchain complexes of neurofilament peptides: A putative link between $Al^{3+}$ and Alzheimer disease," *Proc. Natl. Acad. Sci.*, vol. 91, pp. 4902-4906 (1994).

Hollosi, M., et al., "$Ca^{2+}$-Induced Conformational Transitions of Phosphorylated Peptides," *Biopolymers*, vol. 33, pp. 497-510 (1993).

Hollosi, M., et al., "Metal Ion-induced Conformational Changes of Phosphorylated Fragments of Human Neurofilament (NF-M) Protein," *J. Mol. Biol.*, vol. 223, pp. 673-682 (1992).

Holly, S., et al., "FT-IR Spectroscopy indicates that $Ca^{2+}$-binding to phosphorylated C-terminal fragments of the midsized neurofilament protein subunit results in β-sheet," *Biochemical and Biophysical Research Communications*, vol. 197, No. 2, pp. 755-762 (1993).

Jimenez Del Rio, M., et al., "Transition Metal-Induced Apoptosis in Lymphocytes Via Hydroxyl Radical Generation, Mitochondria Dysfunction, and Caspase-3 Activation: An In Vitro Model for Neurodegeneration," *Archives of Medical Research*, vol. 35, pp. 185-193 (2004).

Jones, K. C., "Human Exposure to Environmental Aluminium,", pp. 243-244, (1988) Geochemistry and Health.

Knapp, M.J., et al., "A 30-Week Randomized Controlled Trial of High-Dose Tacrine in Patients with Alzheimer's Disease," *JAMA*, vol. 271, No. 13, pp. 985-991 (1994).

Kruck, T.P.A., "Aluminium—Alzheimer's link?," *Nature*, vol. 363, pp. 119 (1993).

Landsberg, et al., "Aluminium in Alzheimer's?", *Nature*, vol. 362, pp. 418, (1993).

Landsberg, J. P., et al., "Absence of aluminium in neuritic plaque cores in Alzheimer's disease," *Nature*, vol. 360, pp. 65-68 (1992).

Landsberg, J. P., et al., "Alzheimer's response," *Nature*, vol. 364, pp. 294 (1993).

Leterrier, J.F., et al., "A Molecular Mechanism for the Induction of Neurofilament Bundling by Aluminum Ions," *Journal of Neurochemistry*, vol. 58, No. 6, pp. 2060-2070 (1992).

Lovell, M.A., "Laser Microprobe Analysis of Brain Aluminum in Alzheimer's Disease," *American Neurological Association*, vol. 33, No. 1(1993).

Maltby, N., et al., "Efficacy of tacrine and lecithin in mild to moderate Alzheimer's disease: double blind trial," *BMJ*, vol. 308, pp. 879-883 (1994).

Markesbery, W.R., et al., "Aluminum and Alzheimer's Diseas," *Clinical Neuroscience*, vol. 1, pp. 212-218 (1993).

Martin, R. B., "Aluminosilicate Stabilities Under Blood Plasma Conditions," *Polyhedron*, vol. 9, No. 2/3, pp. 193-197(1990).

Martyn, C.N., et al., "Geographical Relation between Alzheimer's Disease and Aluminium in Drinking Water," *The Lancet*, pp, 59-62 (1989).

McLachlan, D. R., et al., "Would decreased aluminum ingestion reduce the incidence of Alzheimer's disease?," *Can Med Assoc. J*, vol. 145, No. 7, pp. 793-829 (1991).

Misra, V., et al., "Binding of Silicic Acid by Proteins and its Relation to Toxicity of Silicate Dusts," *Journal of Applied Toxicology*, vol. 3, No. 3, pp. 135-138 (1983).

Morgan, C., et al., "Structure and function of amyloid in Alzheimer's disease," *Progress in Neurobiology*, vol. 74, pp. 323-349 (2004).

Naylor, G.J., et al., "Raised serum aluminum concentration in Alzheimer's disease," *Trace Elements in Medicine*, vol. 6, No. 3, pp. 93-95 (1989).

Otvos, L., et al., "Phosphorylation Loops in Synthetic Peptides of Human Neurofilament Protein Middle-Sized Subunit," *Journal of Protein Chemistry*, vol. 7, No. 4, pp. 365-376 (1988).

Otvos, L., et al., "Reversed-phase high-performance liquid chromatographic separation of synthetic phosphopeptide isomers," *Journal of Chromatography*, vol. 512, pp. 265-272 (1990).

Owens, N.J., "Focus on tacrine HC1," *Hosp Formul*, vol. 28, pp. 679-691 (1993).

Perry, G., et al., "Senile Plaques and Neurofibrillary Tangles: What Role Do They Play in Alzheimer's Disease?," *Clinical Neuroscience*, vol. 1, pp. 199-230 (1993).

Qian, Y., et al., "Differential profiles of copper-induced ROS generation in human neuroblastoma and astrocytoma cells," *Molecular Brain Research*, vol. 134, pp. 323-332 (2005).

Scarpini, E., et al., "Treatment of Alzheimer's disease: current status and new perspectives," *Neurology*, vol. 2, pp. 539-547 (2003).

Schehr, R. S., "Therapeutic Approaches to Alzheimer's Disease," *Bio/Technology*, vol. 12, pp. 140-144 (1994).

Schwarz, K., et al., "Growth-promoting Effects of Silicon in Rats," *Nature*, vol. 239, pp. 333- 334 (1972).

Shen, Z.M., "Study of $Al^{3+}$ Binding and Conformational Properties of the Alanine-Substituted C- Terminal Domain of the NF-M Protein and Its Relevance to Alzheimer's Disease," *Biochemistry*, vol. 33, pp. 9627-9636 (1994).

Silicic Acid, in Cumulated Index Medicus, vol. 32, U. S. Dept. of Health and Human Services, NIH Publication No. 92-259, pp. 582, 12277 (1991).

Stevenson, R., "Drug leads begin to penetrate Alzheimer gloom," *Chemistry in Britain*, pp. 165-167 (1994).

Tiffany-Castiglioni, E., et al., "Astroglia as Metal Depots: Molecular Mechanisms for Metal Accumulation, Storage and Release," *NeuroToxicology*, vol. 22, pp. 577-592 (2001).

Villemagne, V.L., et al., "Imaginem oblivionis: the prospects of neuroimaging for early detection of Alzheimer's disease," *Journal of Clinical Neuroscience*, vol. 12, No. 3, pp. 221-230 (2005).

Vogt, T., "A Possible Relationship between Aluminium in Drinking Water and Alzheimer's Disease in Southern Norway," *The Central Bureau of Statistics of Norway*, pp. 257-266, (1986).

Wisniewski, H.M., et al., "Aluminium and Alzheimer's Disease," *Ciba Foundation Symposium 169*, pp. 142-164 (1992).

Wu, C.W., et al., "Hemoglobin promotes Aβ oligomer formation and localizes in neurons and amyloid deposits," *Neurobiology of Disease*, vol. 17, pp. 367-377 (2004).

International Search Report dated Jun. 22, 2005 from International Application No. PCT/2003/37037, filed Nov. 18, 2003.

* cited by examiner

NH₃⁺-Asp-Ala-Glu-Phe-Arg-His-Asp-Ser-Gly-Tyr-Glu-Val-His-His-
Gln-Lys-Leu-Val-Phe-Phe-Ala-Glu-Asp-Val-Gly-Ser-Asn-Lys-Gly-Ala-
Ile-Ile-Gly-Leu-Met-Val-Gly-Gly-Val-Val-Ile-Ala-COO⁻

(SEQ. ID NO: 1)

2b, R₁ = (CH₂)₃OP(OCH₃)O₂⁻

2c, R₁ = (CH₂)₇CH₃

2d, R₁ = (CH₂)₃CN

3

3a, R₁ =R₂=phenyl

3b, R₁ =(CH₂)₅CH₃
R₂= CH₃

3c, R₁ =phenyl
R₂= CH₃

3d, R₁ =R2= CH₂CH₃

3e, R₁ =(3-cyanobutyl)
R₂= CH₃

3f, R₁ =(CH₂)₃CN
R₂= CH₃

3g, R₁ =(CH₂)₂CN
R₂= CH₃

4

4a, R₁ =R₂=R₃=CH₃

4b, R₁ =R₂= C (CH₃)₃
R₃= CH₃

4c, R₁ =R₂=R₃=CH₂CH₃

4d, R₁ =R2= CH₂CH₃
R₃ =benzyl

Peptide 1 with Fe(III) and compound 3f

Peptide 1 with Fe(III) and compound 3f

```
                        SEQUENCE LISTING

<160> NUMBER OF SEQ ID NOS: 1

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

COMPOSITIONS FOR TREATING AND/OR PREVENTING DISEASES CHARACTERIZED BY THE PRESENCE OF METAL IONS

RELATED APPLICATIONS

This application is a continuation-in-part of International Patent Application No. PCT/US03/37037, filed Nov. 18, 2003, entitled "Compositions for Treating and Preventing Alzheimer's Disease," by O. Friedman, et al., published as WO 2004/045552 on Jun. 3, 2004; which application claims priority to: U.S. Provisional Patent Application Ser. No. 60/427,203, filed Nov. 18, 2002, entitled "Compositions for Treating and Preventing Alzheimer's Disease," by O. Friedman, et al.; U.S. Provisional Patent Application Ser. No. 60/427,105, filed Nov. 18, 2002, entitled "Compositions for Treating and Preventing Alzheimer's Disease," by O. Friedman, et al.; U.S. Provisional Patent Application Ser. No. 60/427,104, filed Nov. 18, 2002, entitled "Compositions for Treating and Preventing Alzheimer's Disease," by O. Friedman, et al.; U.S. Provisional Patent Application Ser. No. 60/427,201, filed Nov. 18, 2002, entitled "Chelating Agents," by O. Friedman, et al.; and U.S. Provisional Patent Application Ser. No. 60/456,345, filed Mar. 20, 2003, entitled "Compositions for Treating and Preventing Alzheimer's Disease," by O. Friedman, et al. This application also claims the benefit of priority to: U.S. Provisional Patent Application Ser. No. 60/576,425, filed May 27, 2004, entitled "Compositions for Treating and/or Preventing Diseases Characterized by the Presence of Metal Ions," by O. Friedman, et al.; and U.S. Provisional Patent Application Ser. No. 60/621,481, filed Oct. 22, 2004, entitled "Silicon-Amino Compositions for Treating and/or Preventing Diseases Characterized by the Presence of Metal Ions," by T. Pochapsky, et al. Each of the above applications is incorporated herein by reference.

FIELD OF THE INVENTION

This invention generally relates to the treatment and/or prevention of diseases characterized by the presence of metal ions, such as Alzheimer's disease and, in particular, to the treatment and/or prevention of such diseases using certain compositions comprising chelating agents and/or silicon compounds.

DESCRIPTION OF THE RELATED ART

Many diseases can be characterized by an excess or an imbalance of metal ions within the body, for example, within an organ or a tissue. An excess of metal ions may, in some cases, affect protein structure or function, or lead to or facilitate certain diseases, such as Alzheimer's disease, Parkinson's disease, various homeostatic diseases, cardiac arrhythmia, various central nervous system (CNS) disorders, blood plasma imbalances, dermatitis, Gerstmann-Stäussler-Scheinker disorder, familial insomnia, Menkes's syndrome, lead poisoning and other heavy metal toxicities, or various prion diseases such as transmissible spongiform encephalopathy or Creutzfeld-Jakob disease. In some cases, an excess of metal ions may also interfere with ion channel function, protein structure or folding, or enzyme function, which can lead to disease states. For example, many proteins and enzymes use metal ions to stabilize their conformation at or as a reactive site.

Physiological removal or sequestration of metal ions may be useful in treating such diseases. However, very few biocompatible agents able to bind ions that can be delivered to a target site are known to exist. One example of a compound able to bind ions within the body is ethylenediaminetetraacetic acid ("EDTA"). The half-life of EDTA in the body, however, is relatively short. Typical doses of EDTA last for only about 1 hour in the body, limiting the effectiveness of this form of treatment.

One disease that can be characterized by an excess of metal ions is Alzheimer's disease. Alzheimer's disease is a common form of senile dementia. Some studies have suggested that 25-50% of all people in their eighties may have Alzheimer's disease. Symptoms of Alzheimer's disease include memory loss, loss of language or cognitive ability, declines in reasoning ability, and reduced use of speech. Behavioral disorders may also be present. Changes in brain physiology may also occur, for example, enlarged ventricles, narrow cortical gyri, or widened sulci. These changes have been attributed to neuronal loss. The deterioration in mental abilities and brain function appears to be irreversible, and may eventually lead to death.

Alzheimer's disease is actually a family of related neurodegenerative diseases. One feature of Alzheimer's disease and other such neurodegenerative diseases is the appearance and accumulation of fibrous proteinaceous structures, commonly known as neurofibrillary tangles or senile plaques. Tau (T) protein is one constituent of neurofibrillary tangles. Tau proteins may form filaments that can give rise to neurofibrillary tangles, for example, when the tau protein is hyperphosphorylated. Beta-amyloid peptide ($A\beta_{1-42}$ or $A\text{-beta}_{1-42}$), a protein containing about 42 amino acids, is one important component of certain senile plaques (FIG. 1).

Causes of Alzheimer's disease include, genetic factors (for instance, certain genes on chromosomes 1, 14, 19, and 21 have been implicated in increased susceptibility to Alzheimer's disease), or environmental factors, especially greater than normal aluminum concentrations. Some studies have shown that increased aluminum concentrations within the brain may be associated with neurofibrillary tangles or senile plaques. Certain studies have suggested a link between the aluminum found in water supplies and the incidence of Alzheimer's disease. Aluminum may also arise from pharmaceuticals or other compounds, such as antacid tablets. Aluminum may be found in the body complexed to other species such as organic species, or dissolved in solution (e.g., within the blood or the cerebrospinal fluid). For example, the aluminum may be present as $Al^{3+}$, $Al(OH)_3$, $Al_2O_3$, or $Al_2(SO_4)_3$, etc.

SUMMARY OF THE INVENTION

This invention, in certain aspects, relates to the treatment and/or prevention of diseases characterized by the presence of metal ions, such as Alzheimer's disease. The subject matter of this invention involves, in some cases, interrelated products, alternative solutions to a particular problem and/or a plurality of different uses of one or more systems and/or articles.

In one aspect, the invention includes a composition. In one set of embodiments, the composition, or at least a portion thereof, is able to enter an organ, e.g., the brain through transport across the blood-brain barrier. In some cases, the composition also includes a pharmaceutically acceptable carrier.

In certain embodiments, the composition includes at least one of a silanol, a silandiol, a silantriol, and/or a compound able to form at least one of a silanol, silandiol, or a silantriol, e.g., upon exposure to physiological conditions. Such compounds may include, for example, a halogenated organosilicon compound or a cyclic organosilicon compound. In some cases, the compound is unable to significantly polymerize in solution. In another set of embodiments, at least 50%, at least 75%, at least 90%, at least 95%, at least 97%, or at least 99% of the compound is able to retain a monomeric structure in vivo.

In one set of embodiments, the composition includes a compound having a structure:

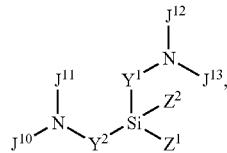

or a salt thereof, where each of $Z^1$ and $Z^2$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. Each of $Y^1$ and $Y^2$ is an moiety interconnecting Si and an N (for example, an alkyl moiety, an aryl moiety, a cyclic moiety, etc.). Each of $J^{10}$, $J^{11}$, $J^{12}$, and $J^{13}$ independently is H or comprises at least one of a carbon atom, a nitrogen atom, an oxygen atom, or a sulfur atom. In one embodiment, each of $J^{10}$, $J^{11}$, $J^{12}$, and $J^{13}$ is independently hydrogen, an alkyl, or an aryl. In another embodiment, at least one of $J^{10}$, $J^{11}$, $J^{12}$, and $J^{13}$ is an alkyl having no more than three or four carbon atoms. In yet another embodiment, at least one of $Y^1$ and $Y^2$ has a structure:

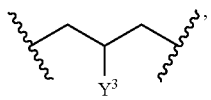

where $Y^3$ may include a hydrogen or a non-hydrogen atom. In still another embodiment, $Y^3$ comprises a hydrophobic moiety. As used herein in reference to various chemical structures, the symbol $\xi$ indicates where a chemical structure is attached to a parent chemical structure, as is readily understood by those of ordinary skill in the art. For example, in the above structure, for at least one of $Y^1$ and $Y^2$, the two $\xi$ symbols indicate where the above structure respectively attaches to N and Si in the parent chemical structure immediately preceding the above structure.

In another set of embodiments, the composition includes a silicon compound comprising an aminoalkyl moiety. In one embodiment, the compound has a structure:

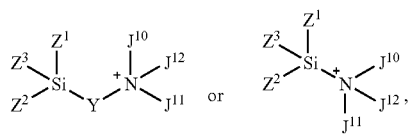

or a salt thereof, where each of $Z^1$, $Z^2$, and $Z^3$ is independently one of H, X, R, OH, $OR^1$, or $NJ^1J^2$, with R comprising at least one carbon atom, X being a halogen or a pseudohalogen, and $R^1$ comprising at least one carbon atom. Each J independently is H or comprises at least one of a carbon atom, a nitrogen atom, an oxygen atom, or a sulfur atom, and Y is a moiety interconnecting Si and N (for example, an alkyl moiety, an aryl moiety, a cyclic moiety, etc.).

In still another set of embodiments, a composition of the invention includes a compound having a structure:

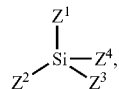

or a salt thereof, where each of $Z^1$, $Z^2$, $Z^3$, and $Z^4$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. The compound may include at least one carbon atom, i.e., at least one of $Z^1$, $Z^2$, $Z^3$, and $Z^4$ comprises at least one carbon atom. In certain embodiments, $Z^1$, $Z^2$, $Z^3$, and $Z^4$ are not all, simultaneously, one of H or R; and $Z^1$, $Z^2$, $Z^3$, and $Z^4$ are not all simultaneously acetate.

In another set of embodiments, the compound may have a structure such as:

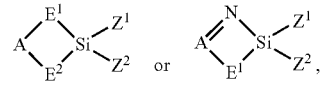

or a salt thereof, where each of $Z^1$ and $Z^2$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. In this structure, A is a moiety including at least one of a carbon atom and a silicon atom. Each of $E^1$ and $E^2$ (where applicable) independently is either (a) one of O and $NJ^3$, or (b) absent such that Si is covalently bonded to moiety A. $J^3$ is H or comprises at least one of a carbon atom, a nitrogen atom, an oxygen atom, or a sulfur atom. In certain instances, $E^1$ and $E^2$ (where applicable) are not both absent.

In yet another set of embodiments, a composition of the invention includes cyclic organosilicon compound, i.e., a cyclic organic compound containing at least one silicon atom. For example, the cyclic organosilicon compound may have a structure such as:

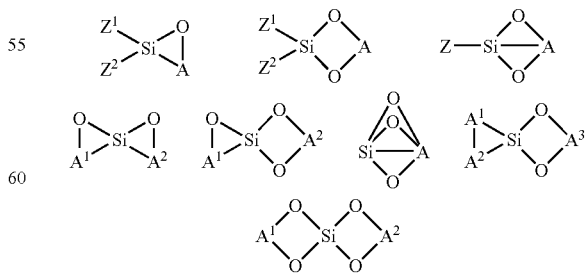

In these structures, each A independently is a moiety having at least one of a carbon atom and a silicon atom, and each Z independently is one of H, X, R, OH, OR$^1$, or NJ$^1$J$^2$, with R comprising at least one carbon atom, X being a halogen or a pseudohalogen, R$^1$ comprising at least one carbon atom, and J$^1$ and J$^2$ each independently being H, or comprising at least one of a carbon atom, a nitrogen atom, an oxygen atom, or a sulfur atom. In some cases, the composition may include a salt of any of the above-described structures.

In still another set of embodiments, a composition of the invention comprises a compound having at least two silicon atoms. In one embodiment, the compound has a structure:

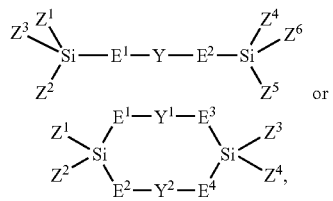

or a salt thereof, where each of Z$^1$, Z$^2$, Z$^3$, Z$^4$, Z$^5$, and Z$^6$ independently is one of H, X, R, OH, OR$^1$, or NJ$^1$J$^2$, with R comprising at least one carbon atom, X being a halogen or a pseudohalogen, R$^1$ comprising at least one carbon atom, and J$^1$ and J$^2$ each independently being H, or comprising at least one of a carbon atom, a nitrogen atom, an oxygen atom, or a sulfur atom. In another embodiment, the composition includes a polymer having a repeat unit comprising at least one silicon atom. In yet another embodiment, the compound may have a structure such as:

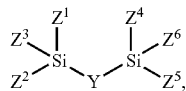

or a salt thereof, where each of Y, Y$^1$ and Y$^2$ independently is an interconnecting moiety comprising at least one carbon atom (for example, an alkyl moiety, an aryl moiety, a cyclic moiety, etc.), and each of Z$^1$, Z$^2$, Z$^3$, Z$^4$, Z$^5$, and Z$^6$ independently is one of H, X, R, OH, OR$^1$, or NJ$^1$J$^2$, with R comprising at least one carbon atom, X being a halogen or a pseudohalogen, R$^1$ comprising at least one carbon atom, and J$^1$ and J$^2$ each independently being H, or comprising at least one of a carbon atom, a nitrogen atom, an oxygen atom, or a sulfur atom. Each of E$^1$, E$^2$, E$^3$, and E$^4$ independently is either (a) one of O and NJ$^3$, or (b) absent such that a Si is covalently bonded to a Y moiety. J$^3$ can be H or comprise at least one of a carbon atom, a nitrogen atom, an oxygen atom, or a sulfur atom. Typically, at least one E moiety is present within the structure.

In another set of embodiments, a compound of the invention includes a chelating agent able to bind to aluminum, copper, ferric, ferrous, or another metal ion (or is able to form a chelating agent able to bond to aluminum or another metal ion). In one embodiment, a compound of the invention has a structure:

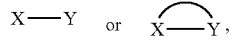

where X is a chelating agent able to bond to aluminum, copper, ferric, ferrous, or another metal ion, or is able to form a chelating agent able to bond to aluminum or another metal ion. Additionally, Y is a structure able to facilitate transport of the compound (or a portion thereof) across the blood-brain barrier, the structure comprises at least one chemical bond, and the structure—is a moiety that can be hydrolyzed under physiological conditions, e.g., within the brain or within the bloodstream, for example, to OH. In some cases, the chelating agent may be any agent able to bind or otherwise immobilize an ion, for example, so that it becomes complexed or otherwise bound to the chelating agent instead of remaining free in solution.

In another aspect, the invention is a method. In one set of embodiments, the method includes administering, to a subject, a therapeutically effective amount of a composition comprising at least one of a silanol compound, a silandiol compound, a silantriol compound, a cyclic organosilicon compound, and/or a compound able to be hydrolyzed within the subject to at least one of a silanol compound, a silandiol compound, or a silantriol compound. In another set of embodiments, the method includes administering, to a subject, one or more of the compounds described above. In some cases, the subject is susceptible to or exhibits symptoms of Alzheimer's disease. In other cases, the subject is susceptible to or exhibits symptoms of a disease characterized by an excess of an ion such as a metal ion. In certain cases, the subject is not otherwise indicated for treatment with the composition. For example, the subject may not be indicated as having a disease treatable by the inhibition of leukocyte elastase.

In some embodiments, a compound of the invention is able to bind to (or otherwise interact with) aluminum, copper, ferric, ferrous, and/or other metal ions such as divalent or trivalent metal ions, and/or is able to be hydrolyzed within the subject to form a compound able to bind to aluminum and/or other metal ions. In certain embodiments, the organosilicon compound, or at least a portion thereof, is able to enter an organ, e.g., the brain through transport across the blood-brain barrier. In other embodiments, however, the organosilicon compound is not able to enter an organ such as the brain, but instead, remains in circulation in the bloodstream, for example, to remove or sequester aluminum or other ions within the blood before they enter the brain or other organs. The composition may also include a pharmaceutically acceptable carrier in certain cases.

In another set of embodiments, the method includes administering, to a subject, a therapeutically effective amount of a composition comprising a compound having a structure:

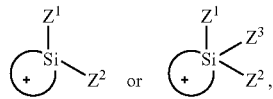

or a salt thereof, where each of Z$^1$, Z$^2$, and Z$^3$ independently is one of H, X, R, OH, OR$^1$, or NJ$^1$J$^2$, with R comprising at least one carbon atom, X being a halogen or a pseudohalogen, R$^1$ comprising at least one carbon atom, and J$^1$ and J$^2$ each independently being H, or comprising at least one of a carbon atom, a nitrogen atom, an oxygen atom, or a sulfur atom. For clarity, in any of the chemical structures described herein, such as in the above-described chemical structures, not all of the atoms bonded to silicon are drawn. In some cases, the subject is susceptible to or exhibits symptoms of Alzheimer's disease or other disease characterized by an excess of metal ions. The structure

indicates a portion of the compound that can be positively charged when the compound is located within the subject, for example, in an active site. In one embodiment, the subject is not otherwise indicated for treatment with the composition. In another embodiment, the structure

is a portion of the compound that has a structure that allows the compound, or at least a portion thereof, to enter into an organ, or cross the blood-brain barrier.

In one set of embodiments, the method includes administering to a subject a composition that includes a compound able to be converted, within the subject, into a form able to bind aluminum, copper, ferric, ferrous, and/or other metal ions such as divalent or trivalent metal ions, e.g., through hydrolysis. In another set of embodiments, the method includes administering, to a subject, a therapeutically effective amount of a composition including a compound able to cross the blood-brain barrier and/or bind aluminum, copper, ferric, ferrous, and/or other metal ions.

In another set of embodiments, the method includes administering, to a subject, a therapeutically effective amount of a composition comprising a compound comprising, within the molecular structure of the compound, at least two silicon atoms. In one embodiment, the compound can have a molecular weight of at least about 100 g/mol, at least about 200 g/mol, at least about 300 g/mol, at least about 400 g/mol, at least about 500 g/mol, at least about 600 g/mol, at least about 700 g/mol, at least about 800 g/mol, at least about 900 g/mol, at least about 1000 g/mol, or more in some cases. In another embodiment, the compound is a salt.

In yet another set of embodiments, the method includes administering, to a subject, a therapeutically effective amount of a composition comprising a compound having, within the molecular structure of the compound, a silicon atom and a nitrogen atom.

In still another set of embodiments, the method is a method of chelating metals in vivo. In one embodiment, the method includes administering, to a subject, a therapeutically effective amount of a composition comprising a silicon polymer and, in some cases, a pharmaceutically acceptable carrier. In some instances, the silicon polymer may be hydroxylated and/or halogenated.

In another set of embodiments, the method is a method of facilitating the reversion of a protein having a non-functional or a dysfunctional conformation (i.e., functioning at a less than physiologically normal level) to a functional conformation. The method, in one embodiment, includes the step of introducing a compound comprising silicon into a subject, where the subject has, or is suspected of having, a disease or condition characterized by having a protein, a lipid, or a sugar bound to one or more metal atoms. The protein, lipid, or sugar may have a non-functional or a dysfunctional conformation when so bound to the one or more metal atoms. The method can also include allowing at least some of the metal atoms to be transferred from the protein, lipid, or sugar to the silicon compound. In some cases, the silicon polymer may be hydroxylated and/or halogenated.

In yet another set of embodiments, the method includes administering, to a neurological system of a subject susceptible to or exhibiting symptoms of Alzheimer's disease, a therapeutically effective amount of a composition comprising a compound having a silicon atom. In one embodiment, the composition includes a compound having a structure:

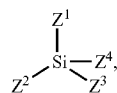

a salt thereof, where each of $Z^1$, $Z^2$, $Z^3$, and $Z^4$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. In some cases, one, two, three, or four of $Z^1$, $Z^2$, $Z^3$, and $Z^4$ may each be OH and/or acetate. In another embodiment, the composition includes a silicate, such as sodium silicate, and/or a metasilicate, such as sodium metasilicate, or the like. In yet another embodiment, the composition includes a silicon salt.

In still another aspect, the invention comprises a composition. In one set of embodiments, the composition comprises a compound having a structure:

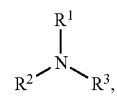

where each of $R^1$, $R^2$, and $R^3$ independently is —H or having a structure:

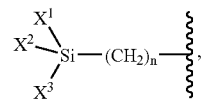

such that at least one of $R^1$, $R^2$, and $R^3$ has a structure:

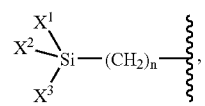

where, independently for each of $R^1$, $R^2$, and $R^3$, each of $X^1$, $X^2$, and $X^3$ independently is a halogen or an alkoxy and n is a positive integer. $R^1$, $R^2$, and $R^3$ are not all simultaneously —H.

The composition, in another set of embodiments, includes a compound having a structure:

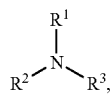

each of $R^1$, $R^2$, and $R^3$ independently being —H, an alkyl, or having a structure:

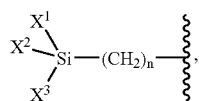

such that at least one of $R^1$, $R^2$, and $R^3$ has a structure:

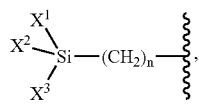

where, independently for each of $R^1$, $R^2$, and $R^3$, each of $X^1$, $X^2$, and $X^3$ independently is a halogen, an alkyl, —OH, or an alkoxy and n is a positive integer.

In another set of embodiments, the composition comprises a compound having a structure:

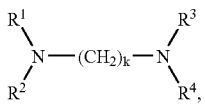

where k is a positive integer and each of $R^1$, $R^2$, $R^3$, and $R^4$ independently is —H or has a structure:

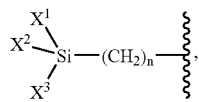

such that at least one of $R^1$, $R^2$, and $R^3$ has a structure:

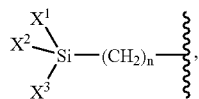

where, independently for each of $R^1$, $R^2$, $R^3$, and $R^4$, each of $X^1$, $X^2$, and $X^3$ independently is a halogen or an alkoxy and n is a positive integer. $R^1$, $R^2$, $R^3$ and $R^4$ are not all simultaneously —H.

In yet another set of embodiments, the composition comprises a compound having a structure:

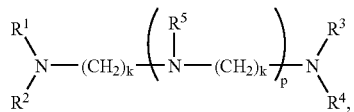

where k and p each independently being a positive integer and each of $R^1$, $R^2$, $R^3$, $R^4$, and $R^5$ independently is —H or has a structure:

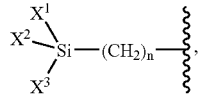

such that at least one of $R^1$, $R^2$, and $R^3$ has a structure:

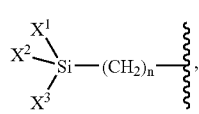

where, independently for each of $R^1$, $R^2$, $R^3$, and $R^4$, each of $X^1$, $X^2$, and $X^3$ independently is a halogen or an alkoxy and n is a positive integer. $R^1$, $R^2$, $R^3$, $R^4$, and $R^5$ are not all simultaneously —H.

Examples of such compositions include, but are not limited to $[(CH_3O)_3Si—CH_2)_3]_2NH$, or $[(CH_3O)_3Si—CH_2)_3]NH—CH_2—CH_2—NH[(CH_2)_3—Si(OCH_3)_3]$.

In another embodiment, the composition may include a compound having a structure:

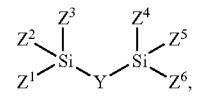

where each of $Z^1$, $Z^2$, $Z^3$, $Z^4$, $Z^5$, and $Z^6$ independently is one of H, X, R, OH, $OR^1$, or $NJ^1J^2$, R comprises at least one carbon atom, X is a halogen, $R^1$ comprises at least one carbon atom, and $J^1$ and $J^2$ each independently are H, or comprises at least one of a carbon atom, a nitrogen atom, an oxygen atom, or a sulfur atom, and Y comprises at least one carbon atom, or a salt thereof.

In some embodiments, any one or more of the above compositions may also include a pharmaceutically acceptable carrier.

In another aspect, the invention provides a method. In one set of embodiments, the method includes administering, to a subject, any one or more of the above compositions or other compositions described herein, optionally in combination with a pharmaceutically acceptable carrier. In some cases, the subject is diagnosed as having or being at risk of a disease characterized by the presence of metal ions, such as Alzheimer's disease, as further discussed herein. In certain instances, the method includes administering, to a subject, any one or more of the above compositions in an amount of a composition sufficient to treat the disease.

In another aspect, the method is a method of treating or preventing Alzheimer's disease or other neurological disorder. In one set of embodiments, the method includes an act of administering, to a subject, a therapeutically effective amount of a composition comprising one or more compounds having the structures:

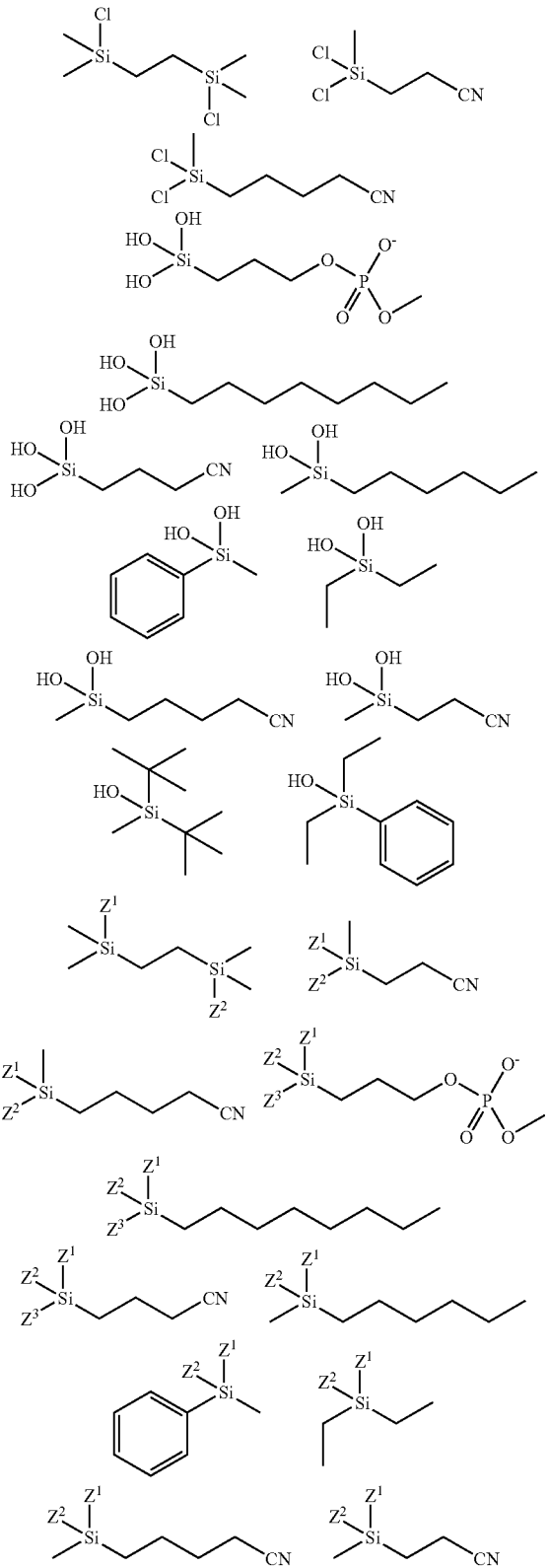

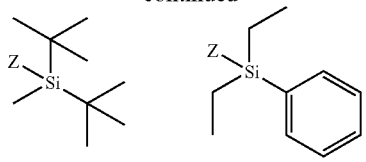

In the above structures, each Z independently is a halogen, —OH, or —OR, R being an alkyl.

In another set of embodiments, the method includes an act of administering, to a subject, a therapeutically effective amount of a composition comprising a compound having a structure:

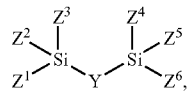

where each of $Z^1$, $Z^2$, $Z^3$, $Z^4$, $Z^5$, and $Z^6$ independently is one of H, X, R, OH, $OR^1$, or $NJ^1J^2$, R includes at least one carbon atom, X is a halogen, $R^1$ comprises at least one carbon atom, and $J^1$ and $J^2$ each independently are H, or comprises at least one of a carbon atom, a nitrogen atom, an oxygen atom, or a sulfur atom, and Y comprises at least one carbon atom, or a salt thereof.

In another aspect, the invention includes the use of a composition in the manufacture of a medicament for treatment of diseases such as Alzheimer's disease characterized by the presence of metal ions. In one set of embodiments, the composition comprises one or more of the compounds described above. It should be understood that everywhere a method of treating a subject with a composition is described herein, the invention also involves, in another aspect, the use of that composition in the manufacture of a medicament for the treatment of the subject.

In still another aspect, the invention is directed to a method of making any of the embodiments described herein. In yet another aspect, the invention is directed to a method of using any of the embodiments described herein. In another aspect, the invention is directed to a method of promoting any of the embodiments described herein.

Other advantages, novel features, and objects of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

BRIEF DESCRIPTION OF THE DRAWINGS

Non-limiting embodiments of the present invention will be described by way of example with reference to the accompanying drawings in which:

FIG. 1 illustrates an A-beta$_{1-42}$ sequence (SEQ ID NO: 1);

DETAILED DESCRIPTION

Figure 2A:
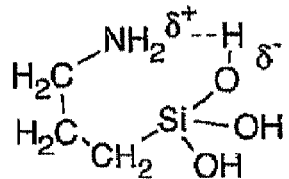
FIGS. 2A-2U illustrate various chemical structures useful in the invention.
Figure 2B:
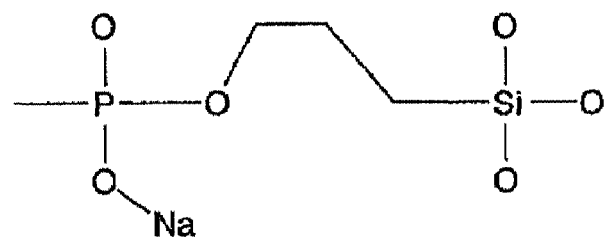
Figure 2C:
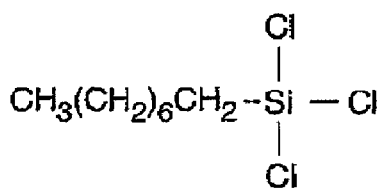
Figure 2D:
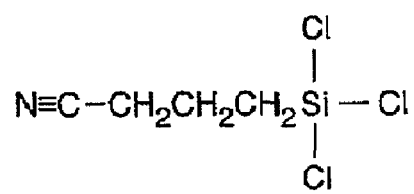
Figure 2E:
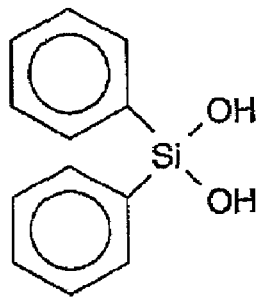
Figure 2F:
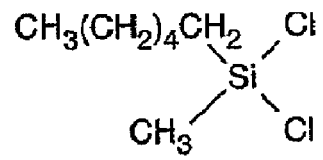
Figure 2G:
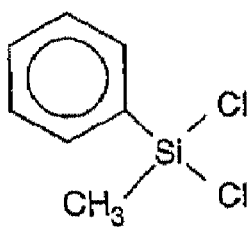
Figure 2H:
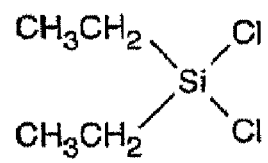
Figure 2I:
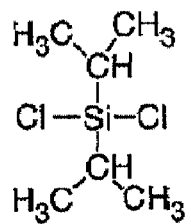
Figure 2J:
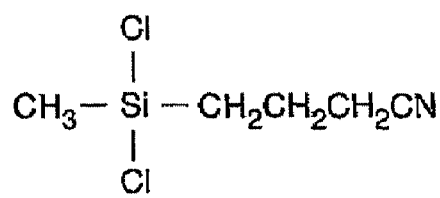
Figure 2K:
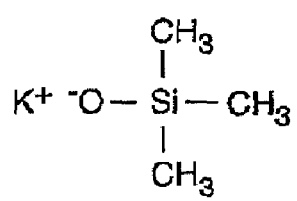
Figure 2L:
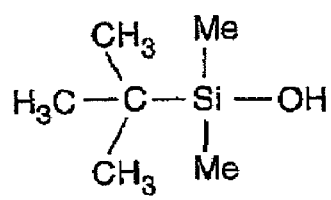
Figure 2M:
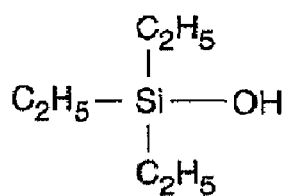
Figure 2N:
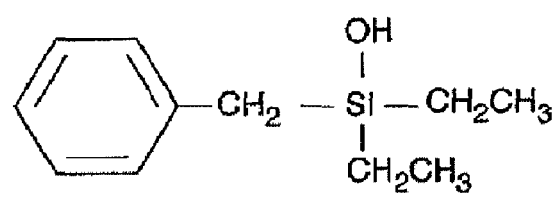
Figure 2O:
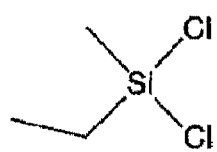
Figure 2P:
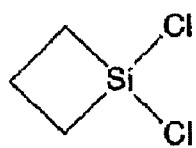
Figure 2Q:
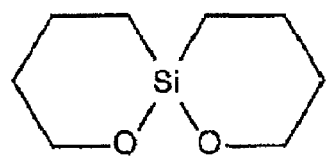
Figure 2S:
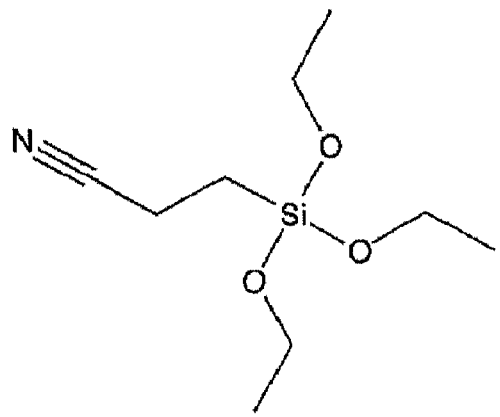
Figure 2T:
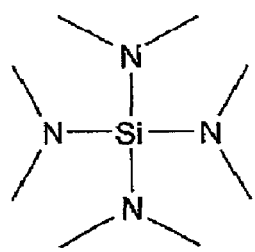
Figure 2R:
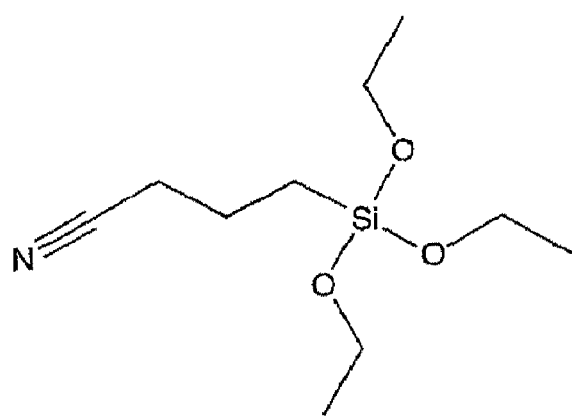

The present invention generally relates to the treatment and/or prevention of Alzheimer's disease, other neurodegenerative diseases, and/or diseases characterized by the presence of certain metal ions, by using certain compositions including organosilicon compounds. A composition of the invention may be administered to a mammal, such as a human. In some cases, the composition may include a silanol, a silandiol, a silantriol, or a cyclic organosilane, and/or be able to form a silanol, a silandiol, or a silantriol upon exposure to physiological conditions such as are found in the blood, in the stomach and/or gastrointestinal tract, or in the brain or other organ. In certain cases, the organosilicon compound may be bound to a moiety able to be transported across the blood-brain barrier into the brain, for example, an amino acid, a peptide, a protein, a virus, etc. The organosilicon compound may also be labeled (e.g., fluorescently or radioactively) in certain instances. In some embodiments, the composition, or a portion thereof, may sequester aluminum, copper, ferric, ferrous, or other ions, for example, by electrostatically binding to the ions. The composition may also include other functionalities such as amines, certain alkyl and/or aryl moieties (including substituted alkyls and/or aryls), or hydrophobic moieties, for example, to facilitate transport of the organosilicon compound through the blood-brain barrier.

The following are incorporated herein by reference: U.S. Pat. No. 5,523,295, issued Jun. 4, 1996, entitled "Method for Treating and Preventing Alzheimer's Disease," by G. D. Fasman; U.S. Provisional Patent Application Ser. No. 60/427,203, filed Nov. 18, 2002, entitled "Compositions for Treating and Preventing Alzheimer's Disease," by O. Friedman, et al.; U.S. Provisional Patent Application Ser. No. 60/427,105, filed Nov. 18, 2002, entitled "Compositions for Treating and Preventing Alzheimer's Disease," by O. Friedman, et al.; U.S. Provisional Patent Application Ser. No. 60/427,104, filed Nov. 18, 2002, entitled "Compositions for Treating and Preventing Alzheimer's Disease," by O. Friedman, et al.; U.S. Provisional Patent Application Ser. No. 60/427,201, filed Nov. 18, 2002, entitled "Chelating Agents," by O. Friedman, et al.; U.S. Provisional Patent Application Ser. No. 60/456,345, filed Mar. 20, 2003, entitled "Compositions for Treating and/or Preventing Diseases Characterized by the Presence of Metal Ions," by O. Friedman, et al.; U.S. Provisional Patent Application Ser. No. 60/576,425, filed May 27, 2004, entitled "Compositions for Treating and/or Preventing Diseases Characterized by the Presence of Metal Ions," by O. Friedman, et al.; U.S. Provisional Patent Application Ser. No. 60/621,481, filed Oct. 22, 2004, entitled "Silicon-Amino Compositions for Treating and/or Preventing Diseases Characterized by the Presence of Metal Ions," by T. Pochapsky, et al.; and International Patent Application No. PCT/US03/37037, filed Nov. 18, 2003, entitled "Compositions for Treating and Preventing Alzheimer's Disease," by O. Friedman, et al., published as WO 2004/045552 on Jun. 3, 2004.

The indefinite articles "a" and "an," as used herein in the specification and in the claims, unless clearly indicated to the contrary, should be understood to mean "at least one."

The term "determining," as used herein, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction.

As used herein, a material is "able to cross the blood-brain barrier" if it is capable of being transported (passively or actively) from the blood to the brain or central nervous system in vivo under physiological conditions using endogenously available transport processes such as diffusion or certain endogenous transport systems. For example, a composition of the invention (or a portion thereof) may include a sugar or a peptide, and/or be able to be substituted as a substrate (i.e., a mimic) in a sugar and/or a peptide transport system of the blood-brain barrier (e.g., endogenous transport proteins), thus allowing transport of the composition across the blood-brain barrier to occur. As used herein, the "blood-brain barrier" is given its ordinary meaning as used in the art, i.e., the cellular barrier separating the bloodstream from the "neurological system," i.e., the brain and central nervous system, including the spinal cord.

"Treatment of Alzheimer's disease," as used herein, includes preventing, arresting, altering, and/or reversing formation of neurofibrillary tangles and/or senile plaques within the brain, and may be performed on subjects "in need of such treatment," i.e., a subject that exhibits symptoms of Alzheimer's disease, a subject susceptible to or otherwise at increased risk for Alzheimer's disease, or a subject not exhibiting symptoms of Alzheimer's disease, but for whom it is desired to decrease the risk of Alzheimer's disease (e.g., a vaccination or a prophylactic treatment). The term "patient" or "subject" as used herein includes mammals such as humans, as well as non-human mammals such as non-human primates, cows, horses, pigs, sheep, goats, dogs, cats, rabbits, or rodents such as mice or rats.

It should be understood that any of the compositions or methods described herein in reference to Alzheimer's disease can also be used, in some cases, to treat other diseases characterized by an excess of metal ions. As used herein, a disease "characterized by an excess of an ion" includes any disease where an excess of an ion (e.g., a metal ion) within an organ or a system of the body may lead to health-related problems. Examples of such ions include, but are not limited to, iron$^{2+}$ (ferrous), iron$^{3+}$ (ferric), copper, lead, aluminum, magnesium, calcium, mercury, strontium, beryllium, cobalt, zinc, nickel, arsenic, etc. The ions may be divalent or trivalent (i.e., having a net charge of ±2 or ±3, respectively) in certain instances. In some cases, the disease may result in misfolded proteins, due to the presence of excess ions. As one example, Alzheimer's disease can be characterized by an excess of aluminum ions in the brain. Other brain diseases which may be characterized by an excess of ions include, for example, certain prion diseases such as transmissible spongiform encephalopathy or Creutzfeldt-Jakob disease. Other diseases where an excess of ions such as metal ions has been implicated include Parkinson's disease, various homeostatic diseases, cardiac arrhythmia, various central nervous system (CNS) disorders, blood plasma imbalances, dermatitis, Gerstmann-Staussler-Scheinker disorder, familial insomnia, Menkes's syndrome, or heavy metal toxicity or poisoning. In some cases, the disease may be created by environmental factors, for example, an excess of ions such as aluminum, lead, copper or iron from the environment. In other cases, the disease ions may be created through diet, drinking water, or the like. The organ or system may be any organ or system in the body, for example, within the bloodstream, within the brain, liver, kidneys, skin, fatty tissue, etc. Other diseases characterized by an excess of ions may be readily identified by those of ordinary skill in the relevant art.

As used herein, an "amino acid" is given its ordinary meaning as used in the field of biochemistry. An amino acid typically has a structure:

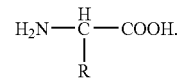

In this structure, R may be any suitable moiety; for example, R may be a hydrogen atom, a methyl, or an isopropyl. A series of amino acids can be connected to form a peptide or a protein, by reaction of the $NH_2$ of one amino acid with the COOH of the next amino acid to form a peptide (—NH—C(O)) bond. The amino acid may be a natural amino acid or an unnatural amino acid. As used herein, the "natural amino acids" are the 20 amino acids commonly found in nature, i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Conversely, an "unnatural amino acid" is an amino acid corresponding to the above structure, where the R moiety does not correspond to one of the 20 natural amino acids. In some cases, the amino acid may also be derivatized in some fashion. For example, the amino acid may be amidated, esterified, side moieties may be attached to the amino acid, etc. Other amino acid derivatization reactions will be known to those of ordinary skill in the art.

As used herein, an "alkyl" is given its ordinary meaning as used in the field of organic chemistry. Alkyl or aliphatic moieties may contain a number of carbon atoms. The moieties may include, for example, between 1 and 15 carbon atoms, between 1 and 10 carbon atoms, or between 1 and 5 carbon atoms. In certain embodiments, the alkyl moiety will have less than 10 carbon atoms, less than 6 carbon atoms, less than 5 carbon atoms, less than 4 carbon atoms, or less than 3 carbon atoms. In some embodiments of the invention, alkyl chains having a certain size may be used to control the hydrophobicity of the composition. The carbon atoms may be arranged in an appropriate configuration within the alkyl moiety, for example, as a straight chain (i.e., an n-alkyl such as methyl ("Me"), ethyl ("Et"), propyl ("Pr"), butyl ("Bu"), pentyl ("Pe"), or hexyl ("Hx")) or a branched chain (e.g., a tert-butyl moiety, or an isoalkyl moiety such as an isopropyl moiety). The alkyl moiety may contain zero or one or more double or triple bonds within its structure, for example, as in an alkene, an alkyne, an alkadiene, an alkadiyne, an alkynene, etc. The alkyl moiety may also contain substituents in some cases. For example, the alkyl moiety may contain a halogen, an alkoxy (e.g., methoxy, ethoxy, or propoxy), an amine (e.g., a primary, secondary, tertiary, or quaternary amine), an ether, a carbonyl (e.g., an acetyl ("Ac") moiety) or a hydroxide as a substituent (i.e., a "substituted alkyl"). If more than one substituent is present, then the substituents may each be the same or different. In some cases, the alkyl moiety includes only carbon and hydrogen atoms; however, in other cases, the atoms within the alkyl moiety may also include nitrogen atoms, oxygen atoms, sulfur atoms, silicon atoms, or any other suitable atom.

Similarly, a "cyclic" moiety, as used herein, is given its ordinary definition as used in the field of organic chemistry, i.e., a moiety that contains at least one ring of atoms, and may contain more than one ring of atoms. That is, a cyclic moiety has at least one chain of atoms that does not have a terminal end. The chain may have, for example, three, four, five, six, seven, eight, nine, or ten or more atoms arranged in a ring. In some embodiments, the cyclic moiety has a maximum size of at most ten atoms, at most eight atoms, or at most seven atoms. In some cases, the cyclic moiety includes only carbon atoms within the ring of the cyclic moiety; however, in other cases, the atoms within the ring may also include nitrogen atoms, oxygen atoms, sulfur atoms, silicon atoms, or any other atom able to covalently bond to at least two different atoms (i.e., a "heterocyclic" moiety). If the cyclic moiety contains more than one ring, the rings may be arranged in any orientation with respect to each other, e.g., the rings may be fused (i.e., at least two rings have more than one atom in common, for example, as in bicyclic moieties, tricyclic moieties, etc.), spiro (i.e., two rings have only one atom in common), a ring may be a substituent on another ring, two or more rings may be connected through an alkyl moiety, etc. The cyclic moiety may contain zero or one or more double or triple bonds within its structure, for example, as in a cycloalkene, a cycloalkyne, a cycloalkadiene, an aromatic moiety, or the like. The terms "aromatic" or "aryl" moieties are given their ordinary meaning as used in the art, e.g., where at least two or more atoms of the moiety participate in delocalized pi bonding. Aryl moieties which include one or more non-carbon atoms (e.g., nitrogen) participating in delocalized pi bonding are "heteroaryl" moieties.

A "silicon compound," as used herein, includes any chemical compound that contains at least one silicon atom. The silicon compound may be water-soluble, lipid-soluble, or exhibit amphiphillic properties, e.g., when located within a subject. An "organosilicon compound," as used herein, is a compound that includes at least one silicon atom bonded to an organic moiety, such as an alkyl, an aryl, an alkoxy, a cycloalkyl, an amine (primary, secondary, tertiary, or quaternary), etc. An "organosilicon composition" includes at least one organosilicon compound and may include other compounds as well, for example, other physiologically active compounds and/or pharmaceutically acceptable carriers such as those further described below. In some embodiments, the silicon atom within the organosilicon compound may be hypercoordinated (i.e., the silicon atom may have a valency of 5 or 6).

In one set of embodiments, the silicon compound includes one or more "hydrolyzable" moieties (for example, a moiety that can by hydrolyzed under physiological conditions, spontaneously and/or through metabolic processes, e.g., to a hydroxide moiety), such as halogens, hydroxides, alkoxides, esters, ethers, etc. Examples include, but are not limited to, a halosilane, a dihalosilane, a trihalosilane, a silanol, a dihalosilanol, a halosilandiol, a silantriol, a halosilanol, etc. Terms such as "silanol," "silandiol," and "halosilane" are given their ordinary meanings as used in the field of chemistry. For instance, a "silandiol" is a compound which includes two hydroxide moieties covalently bonded to a silicon atom, and a "silantriol" is a compound which includes three hydroxide moieties covalently bonded to a silicon atom. Similarly, a "dihalosilane" (e.g., dichlorosilane or bromochlorosilane) is a compound that includes two halogen atoms (as further defined below) each bonded to a silicon atom (i.e., where the halogen atoms may be the same or different), and a "halosilanol" is a compound that includes a halogen and a hydroxide moiety each bonded to a silicon atom within the compound. Terms such as "trihalosilane," "dihalosilanol," and "halodisilanol" are similarly defined. The term "halogen," (or "halo-"), as used herein, includes halogen-group atoms as ordinarily used in the field of chemistry (e.g., fluorine, chlorine, bromine, or iodine). As used herein, "pseudohalogens" are moieties that are not halogen atoms, but have properties similar to halogen compounds. Examples of pseudohalogens include CN, SCN, NCO, etc., and other hydrolyzable moieties that can form labile bonds with silicon (e.g., imidazoles, triazoles, tetrazoles, etc). In many cases, a pseudohalogen moiety can be substituted for a halogen atom in any of the structures described herein.

The organosilicon compounds of the present invention, in one set of embodiments, may inhibit and/or reverse interaction between ions such as aluminum ions, copper ions and/or ferric ions and/or ferrous ions, and physiological (or neurological) components of the brain or other organs, such as A-beta$_{1\text{-}42}$ (A$\beta_{1\text{-}42}$) peptide or other amyloid compounds, tau proteins, etc. For example, certain types of amyloid proteins may be found in the liver or in muscle tissue. The compounds may inhibit and/or reverse such interactions anywhere within the body, e.g., within the brain or other organ, within the blood-brain barrier, within the bloodstream, etc. The term "inhibit" includes inhibition which occurs before and/or after the metal ion complexes with the component. The inhibition may be partial or complete inhibition. One simple test to illustrate the efficacy of the compositions of the invention is to add the composition to a solution containing a a component such as a suitable disease marker, and determine if the added composition is able to prevent or reduce changes in the structure and/or conformation of the component or marker when the solution is exposed to metal ion, such as aluminum, copper, ferric, or ferrous ion. As an example, for Alzheimer's disease, a suitable marker for the disease may be A-beta$_{1\text{-}42}$ peptide or a tau protein (or a cell able to produce A-beta$_{1\text{-}42}$ peptide or a tau protein) that is sensitive to aluminum, i.e., where the structure and/or conformation of the marker is altered upon exposure to aluminum. The composition may be added before or after the marker is exposed to metal or other ions. An example of this process is discussed in Example 1. Those of ordinary skill in the art will understand that "aluminum," as used herein, refers to any form of aluminum that may appear in the body, for example, as aluminum particles, aluminum oxide particles, aluminum ions (Al$^{3+}$), Al(OH)$_3$, Al$_2$O$_3$, Al$_2$(SO$_4$)$_3$, etc. The aluminum may arise from any environmental source, for example, dissolved within drinking water; from aluminum pots, pans, pipes, utensils, or tools; from dust; from components of medical devices; from medications; from jewelry; from aerosols; from deodorants and other products applied to the skin; from aluminum cans, etc. Likewise, "copper" refers to any form of copper that may appear in the body, for example, as copper particles, copper oxide particles and copper ions (cuprous and/or cupric) such as Cu(OH)$_2$, Cu(NO$_3$)$_2$, Cu$_2$(OH)$_2$CO$_3$, etc. The copper may arise from any environmental source, for example, dissolved within drinking water; from cookware, copper pipes; from dust; from components of medical devices; from medications; from jewelry; from aerosols; from deodorants and other products applied to the skin, etc. Likewise, "iron" refers to any form of iron that may appear in the body, for example, as iron particles, iron oxide particles and ferric and ferrous ions (for example, ferric ions such as Fe(OH)$_3$, Fe(NO$_3$)$_3$, FeCl$_3$, etc.). The iron may arise from any environmental source, for example, dissolved within drinking water; from cookware, from food, from iron pipes; from dust; from components of medical devices; from medications; from jewelry; from aerosols; from deodorants and other products applied to the skin, etc.

In some cases, ions such as aluminum, copper, iron, etc. may arise from endogenous sources, and in some instances, such ions may arise through natural processes such as cycles of protein production and degradation. For example, certain proteins and enzymes of the body incorporate certain ions (e.g., iron in hemoglobin or myoglobin). Upon degradation of such proteins or enzymes, the ions may be released into solution, e.g., into intracellular or extracellular solution. Such ions may then interact with other proteins or enzymes, which may cause undesirable effects, such as diseases characterized by excesses of ions, as described herein. In some cases, such ions may increase in concentration over relatively long time periods (e.g., years or decades), eventually causing and/or exacerbating such diseases.

In some embodiments, however, the organosilicon compounds of the invention are not able to enter the brain or other organ. In such embodiments, the organosilicon compounds may remain where they were introduced into the body, or the organosilicon compounds may remain in circulation in the bloodstream. As one example, if a compound is injected directly into the brain (e.g., as further described below), the compound may be unable to cross the blood-brain barrier and hence is able to remain within the brain. As another example, a compound of the invention may be introduced into systemic circulation, to remove or sequester metal ions within the blood before they enter the brain or other organs.

Compositions of the invention, according to one set of embodiments, may be administered to a subject so as to treat (e.g., reverse), prevent, and/or reduce the formation and/or growth of neurofibrillary tangles or senile plaques within the brain. In persons with Alzheimer's disease or other neurodegenerative diseases, the A-beta$_{1-42}$ (Aβ$_{1-42}$) peptide and/or tau proteins found in senile plaques and neurofibrillary tangles may become, in some cases, phosphorylated and/or complexed in the presence of metal ions such as aluminum, copper or iron and/or assume a dysfunctional or a nonfunctional conformation (e.g., a structure that lacks proper activity, or a structure indicative of a diseased state) such as a beta-sheet. The beta-sheet or other nonfunctional/dysfunctional conformation within these proteins may cause the A-beta$_{1-42}$ peptide and/or tau proteins to become insoluble and/or to precipitate, which may thereby cause the formation of neurofibrillary tangles and/or senile plaques within the brain.

In one set of embodiments, a composition of the present invention may bind to or otherwise sequester ions such as metal ions within the body. In one set of embodiments, the ion is divalent or trivalent. The ion may be present within the body, or within an organ or system within the body, in an excess concentration (e.g., significantly above a concentration that is physiologically desirable). In some cases, the composition may sequester the ion by interaction of the ion with a charged portion of the composition, e.g., of the opposite charge.

In some cases, the composition may allow a molecule or structure affected by an excess of metal ions to revert back to its original conformation, or the composition may prevent the formation of nonfunctional or deformed structures, for example, as in a protein that has been denatured, or improperly folded or configured, due to the presence of an excess of metal ions. Thus, compositions of the invention may be determined by their ability to allow a molecule or structure to revert back to its original conformation, etc. The composition may bind and/or sequester the excess ion, which may prevent, inhibit, and/or reduce interaction of the ion with the molecule or structure. For example, the presence of the compositions of the invention in the brain may allow certain A-beta$_{1-42}$ peptide and/or tau proteins to revert back to their original functional structures, and/or prevent the formation of the beta-sheet conformation or other nonfunctional or dysfunctional structures within the A-beta$_{1-42}$ peptide and/or tau proteins. The organosilicon compound may also bind any aluminum, cupric, ferrous, or ferric ions (or other metal ions) present within the brain or other organ, which may cause at least some sequestering of the ions, preventing and/or reducing interaction of the ions with other components of the brain or other organ, for example, with A-beta$_{1-42}$ peptide or tau proteins. The interaction of the composition with metal ions may be, for instance, via an ionic interaction, a hydrogen bond interaction, a van der Waals interaction, a metal ligand interaction, a dative interaction, a hydrophobic interaction, and/or a combination of these. The degree of such binding can be determined by those of ordinary skill in the art; for example, an organosilicon composition of the invention may be mixed with a solution containing a known concentration of corresponding metal ions, and the resulting decrease in the concentration of free metal ions in solution (if any) may be determined or calculated using known techniques for detecting the dissolved ions in solution, for example, using circular dichroism (CD) techniques, atomic absorption spectroscopy, mass spectroscopy, radioactive tracer measurements, or the like.

In some cases, an ion such as aluminum, copper, ferrous, or ferric ion may be sequestered within the body or the brain or other organ by the organosilicon compositions of the invention, for instance, by sequestering the ions with a negatively charged portion of an organosilicon compound. For example, the organosilicon compound may include one or more hydroxide moieties that can become negatively charged under physiological conditions (i.e., deprotonated), enabling electrostatic attraction or binding of aluminum or other metal ions to the compound. In one set of embodiments, the organosilicon compound may be a silanol, a silandiol, or a silantriol. In another set of embodiments, the organosilicon compound may be a silicon compound able to form a silanol, a silandiol, or a silantriol upon hydrolysis of the compound, for example, within the body under physiological conditions (e.g., at a temperature of 37° C. and/or within a generally aqueous environment). In some embodiments, after formation of a metal ion-organosilicon complex (or other ionic-organosilicon complex), the complex may also be removed from the brain or other organ, e.g., physically removed, or otherwise deactivated.

In one aspect, the composition includes a compound containing silicon. Silicon compounds include, e.g., acids, salts, bases, oxides, etc., for example, silicic acid ($H_4SiO_4$), silicon tetraacetate, sodium silicate, sodium metasilicate, etc. Additional examples are described below. The silicon compound may be capable of binding to or otherwise interacting with aluminum, copper, ferric, ferrous, or other metal ions, e.g., within the central nervous system or other organ, or within the bloodstream, as further described below.

In one set of embodiments, the invention provides a composition comprising one or more of the compounds shown below (numbered 1-49), optionally with a pharmaceutically acceptable carrier:

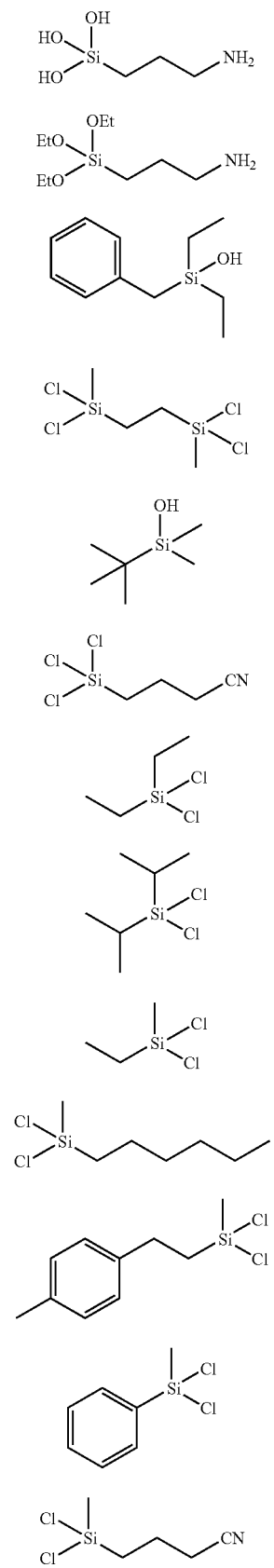
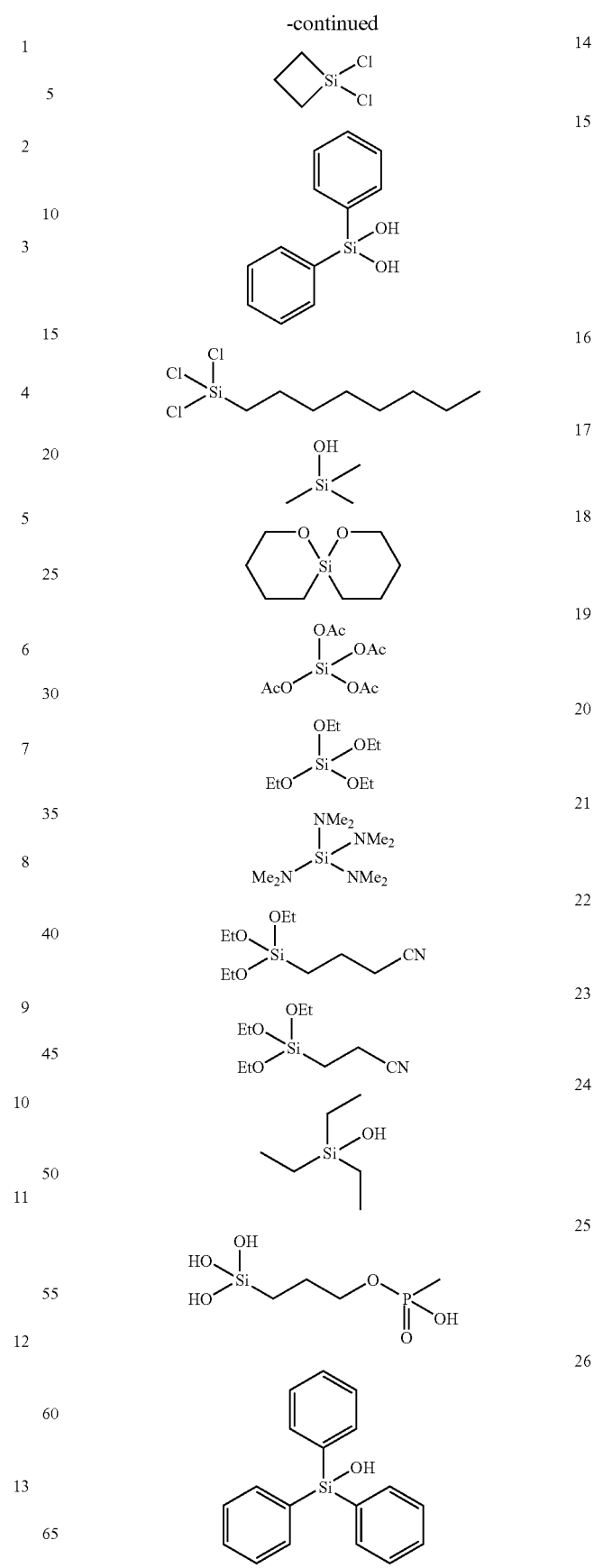

-continued

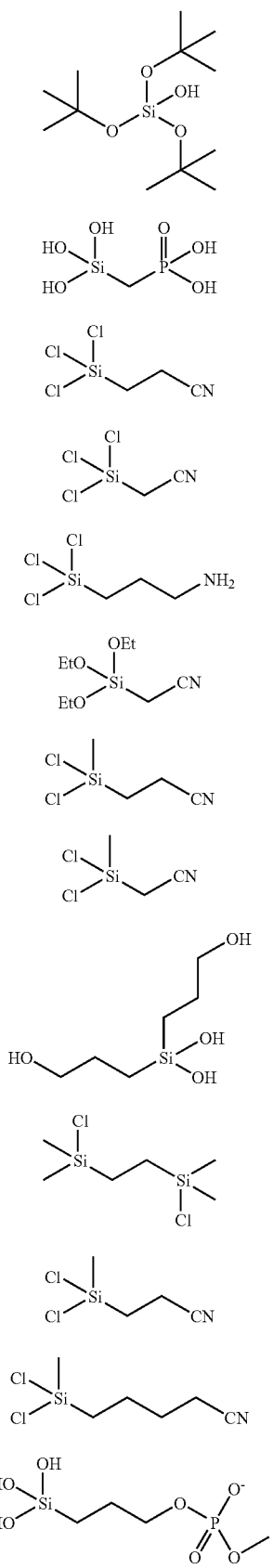

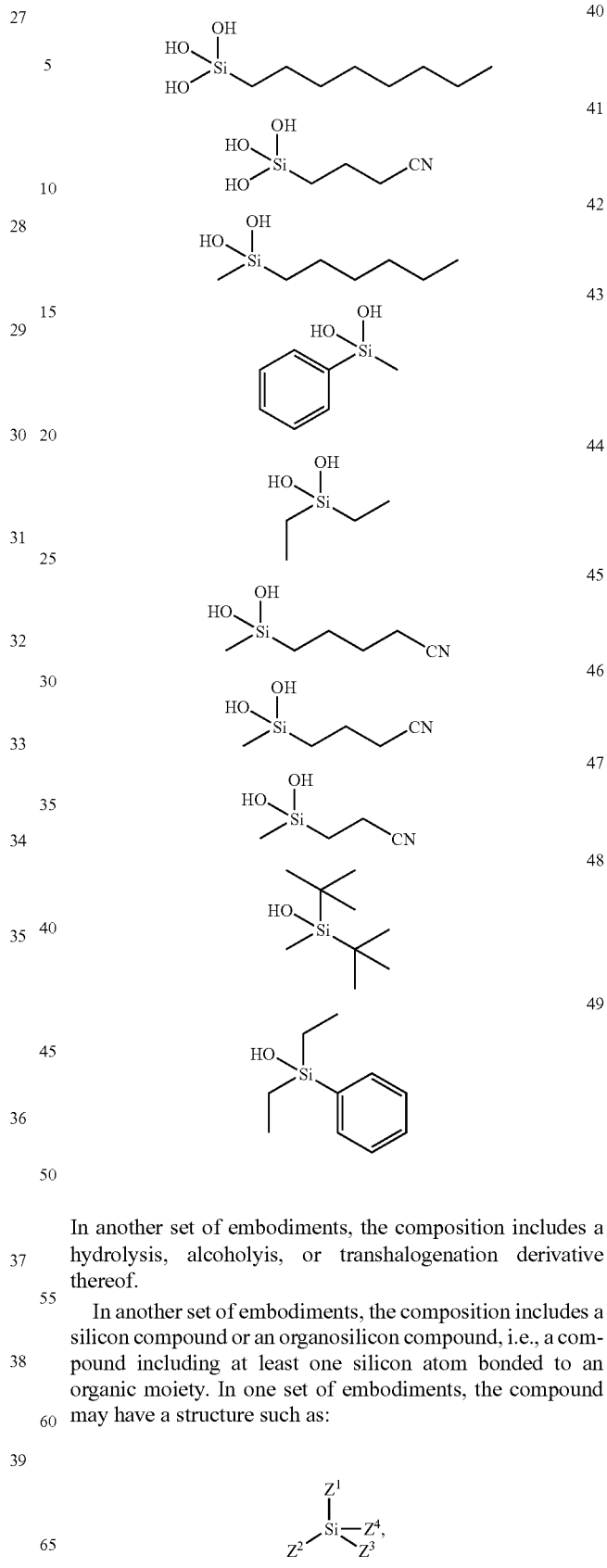

In another set of embodiments, the composition includes a hydrolysis, alcoholyis, or transhalogenation derivative thereof.

In another set of embodiments, the composition includes a silicon compound or an organosilicon compound, i.e., a compound including at least one silicon atom bonded to an organic moiety. In one set of embodiments, the compound may have a structure such as:

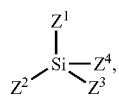

or a salt thereof, where each of $Z^1$, $Z^2$, $Z^3$, and $Z^4$ independently is one of H, X, R, OH, $OR^1$, or $NJ^1J^2$, with R comprising at least one carbon atom, X being a halogen or a pseudohalogen (for example, a nitrile), $R^1$ comprising at least one carbon atom, and $J^1$ and $J^2$ each independently being H, or comprising at least one of a carbon atom, a nitrogen atom, an oxygen atom, or a sulfur atom. The compound, in this instance, includes at least one carbon atom, i.e., at least one of $Z^1$, $Z^2$, $Z^3$, and $Z^4$ comprises at least one carbon atom. In certain embodiments, $Z^1$, $Z^2$, $Z^3$, and $Z^4$ are not all, simultaneously, one of H or R; and $Z^1$, $Z^2$, $Z^3$, and $Z^4$ are not all simultaneously acetate.

In another set of embodiments, the composition includes a compound having a structure:

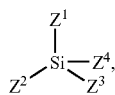

or a salt thereof, where each of $Z^1$, $Z^2$, $Z^3$, and $Z^4$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. In some cases, one, two, three, or four of $Z^1$, $Z^2$, $Z^3$, and $Z^4$ may each be OH and/or acetate. In another embodiment, the composition includes a silicate, such as sodium silicate, and/or metasilicate, such as sodium metasilicate, or the like.

In another set of embodiments, the compound may have a structure such as:

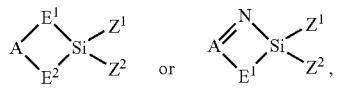

or a salt thereof, where each of $Z^1$ and $Z^2$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. In this structure, A is a moiety having at least one of a carbon atom and a silicon atom. Each of $E^1$ and $E^2$ (where applicable) independently is either (a) one of O and $NJ^3$, or (b) absent such that Si is covalently bonded to moiety A. $J^3$ is H or comprises at least one of a carbon atom, a nitrogen atom, an oxygen atom, or a sulfur atom. In certain instances, $E^1$ and $E^2$ (where applicable) are not both absent, and Si may be bonded to A as well as to $E^1$ or $E^2$, which is not absent.

In yet another set of embodiments, the compound may be a cyclic organosilicon compound. In some cases, more than one ring may be present within the compound, for example, as in a bicyclic or a spiro ring system (i.e., where the rings share one, two, three, or more atoms). In some cases, the two rings of the bicyclic or spiro structure may each comprise alkyl moieties. As an example, the compound, in one embodiment, has a structure such as:

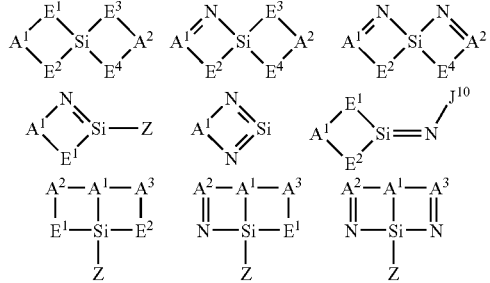

In these structures, each $A^1$, $A^2$, and $A^3$ independently is a moiety having at least one of a carbon atom and a silicon atom, and each of $E^1$ and $E^2$ (where applicable) independently is either (a) one of O and $NJ^3$, or (b) absent such that Si is covalently bonded to moiety $A^1$. Z is one of H, X, R, OH, $OR^1$, or $NJ^1J^2$, with R comprising at least one carbon atom, X being a halogen or a pseudohalogen, and $R^1$ comprising at least one carbon atom. In some cases, $E^1$ and $E^2$ are not both absent. $E^3$ and $E^4$ (where applicable) may independently be either (a) one of O and $NJ^4$, or (b) absent such that Si is covalently bonded to moiety $A^2$. Each J independently is H or comprises at least one of a carbon atom, a nitrogen atom, an oxygen atom, or a sulfur atom. In some cases, the composition of the invention may include a salt of any of the above-described chemical structures.

In some cases, the cyclic organosilicon compound may include one or more hydrolyzable structures, for example, a compound of the invention may be hydrolyzed to form a silanol, a silandiol, or a silantriol, e.g., upon exposure to physiological conditions. For example, the cyclic organosilicon compound may include an ester or an amine moiety that is hydrolyzable to form a hydroxide, which may thus cause one or more rings of the cyclic organosilicon compound to open.

In still another set of embodiments, the compound may be a structure having at least two silicon atoms. In some cases, the compound may be a polymer, for example, a polymer having a repeat unit comprising at least one silicon atom, as further discussed below. In some cases, the compound has a structure such as:

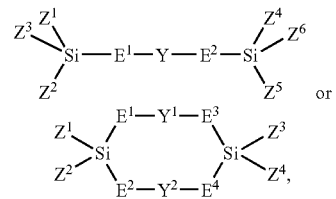

or a salt thereof, where each of Y, $Y^1$ and $Y^2$ independently is an interconnecting moiety comprising at least one carbon atom (for example, an alkyl moiety, an aryl moiety, a cyclic moiety, etc.), and each of $Z^1$, $Z^2$, $Z^3$, $Z^4$, $Z^5$, and $Z^6$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. Each of $E^1$, $E^2$, $E^3$, and $E^4$ (where applicable) independently is either (a) one of O and $NJ^3$, or (b) absent such that a Si is covalently bonded to a Y moiety. $J^3$ can be H or comprises at least one of a carbon atom, a nitrogen atom, an oxygen atom, or a sulfur atom. Typically, at least one E moiety is present within the structure.

In any of the above-described embodiments, any one, two, three, four, five, or six of $Z^1$, $Z^2$, $Z^3$, $Z^4$, $Z^5$, and $Z^6$ (where applicable) may each independently be a halogen (X), for example, F, Cl, Br, I, etc., or a pseudohalogen. In some cases, the halogen or pseudohalogen may be hydrolyzable under physiological conditions to OH.

In another set of embodiments, any one, two, three, four, five, or six of $Z^1$, $Z^2$, $Z^3$, $Z^4$, $Z^5$, and $Z^6$ (where applicable) may each independently be a hydroxide (OH), or an alkoxy (OR$^1$, where $R^1$ comprises at least one carbon atom). The hydroxide, in some instances, can be deprotonated under physiological conditions (i.e., to O$^-$). In some cases, the alkoxy may be hydrolyzable (e.g., within a subject) to form a hydroxide. Non-limiting examples of alkoxy moieties include methoxy (OMe), ethoxy (OEt), propoxy (OPr), isopropoxy, butoxy (OBu), tert-butoxy, sec-butoxy, acetoxy (OAc), etc. The alkoxy moieties may be substituted alkoxy moieties in some cases, for example, a chloromethoxy or a bromochloromethoxy moiety.

Any one, two, three, four, five, or six of $Z^1$, $Z^2$, $Z^3$, $Z^4$, $Z^5$, and $Z^6$ (where applicable) may each independently be a moiety comprising at least one carbon atom in any of the above-described embodiments. For example, R can be an alkyl (e.g., methyl, ethyl, propyl, isopropyl, butyl, isobutyl, sec-butyl, tert-butyl, pentyl, isopentyl, hexyl, isohexyl, heptyl, isoheptyl, octyl, isooctyl, etc.), a cycloalkyl, an aromatic moiety (e.g., phenyl, benzyl, a substituted phenyl or benzyl, etc.), an aminoalkyl, a hydroxyalkyl (e.g., hydroxymethyl, 1-hydroxyethyl, 2-hydroxyethyl, 3-hydroxpropyl, etc.), a cyanoalkyl (i.e., an alkyl comprising at least one CN, such as cyanoethyl, cyanopropyl, cyanobutyl, etc.). Moieties containing nitrites (e.g., ethylnitrile, proprionitrile, butyronitrile, etc.) may be particularly useful in some cases. Nitrile moieties may allow the compound to bind to metal ions such as aluminum, copper or iron. In some cases, the nitrile moiety may facilitate transport or penetration of the compound across the blood-brain barrier, e.g., as further described below. In some embodiments, the alkyl moieties may further include one or more side moieties. The side moiety may be any non-hydrogen atom or moiety, for example, an alkyl moiety such as a methyl moiety or a cycloalkyl moiety. The side moiety (or moieties) may be chosen, for example, to allow for detection of the compound, to allow the compound to have a certain degree of hydrophobicity or other physical properties, to allow the compound to have certain metabolic functions, to allow the compound to have certain immunological properties, etc. In one set of embodiments, a hydrophobic side chain is attached to the compound, for example, an alkyl moiety, a cyclic moiety, or an aryl moiety. In some cases, the cyclic moiety may be an unsaturated structure, such as a cyclohexyl structure.

In any of the above-described embodiments, the compound can include a phosphono moiety, i.e., a moiety having a structure:

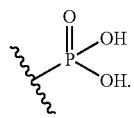

In some cases, for example, under certain physiological conditions, one or both of the OH moieties within the phosphono moiety may be hydrolyzed to O$^-$. In some instances, the phosphono moiety may allow the compound to bind to metal ions such as aluminum, copper or iron (e.g., ferric or ferrous ions).

In any of the above-described embodiments, any one, two, three, four, five, or six of $Z^1$, $Z^2$, $Z^3$, $Z^4$, $Z^5$, and $Z^6$ (where applicable) may each independently comprise a nitrogen-containing moiety, for example, an amine, a hydroxylamine, an oxime, a nitro moiety, etc. As one example, the nitrogen-containing moiety may contain a sulfur atom, which may be bonded to a nitrogen atom, such as in a sulfonamide, i.e., as in the structure N—SO$_2$—Ar, where Ar is an aryl (including a heteroaryl) moiety (bonds removed for clarity). As another example, the nitrogen-containing moiety may contain an oxygen atom, which may be bonded to the nitrogen atom, such as in a hydroxylamine (N—OH), an oxime (N—OR, R comprising at least one carbon atom), or a nitro moiety (NO$_2$). As yet another example, the nitrogen-containing moiety may contain two nitrogen atoms, which may be bonded to each other, such as in a hydrazide (N—NH$_2$), a substituted hydrazide (N—NHJ or N—NHJ$^1$J$^2$, each J comprising at least one of a carbon atom, a nitrogen atom, an oxygen atom, or a sulfur atom, such as acyl, sulfonyl, etc.), or the like.

In any of the above-described embodiments, any one, two, three, four, five, or six of $Z^1$, $Z^2$, $Z^3$, $Z^4$, $Z^5$, and $Z^6$ (where applicable) may each independently have a formula NJ$^1$J$^2$, where J$^1$ and J$^2$ each independently is H or comprises at least one of a carbon atom, a nitrogen atom, an oxygen atom, or a sulfur atom. J$^1$ and J$^2$ each may contain atoms other than carbon and hydrogen atoms, for example, sulfur, nitrogen, or oxygen. As one example, NJ$^1$J$^2$ may be an amine. In some cases, the N of the amine may be covalently bonded to Si. In other cases, however, the N of the amine may not be covalently bonded to Si, and one or more carbon atoms may connect the N of the amine to Si (i.e., a aminocycloalkyl moiety such as an aminoaryl moiety, or an aminoalkyl moiety such as an aminopropyl, an aminobutyl, an aminopentyl, etc). The amine may be a primary amine, a secondary amine, a tertiary amine, or a quaternary amine.

In one set of embodiments, at least one aminoalkyl and/or aminoaryl moiety is chosen such that the amine moiety is able to interact with one or more hydroxide moieties covalently bonded to a silicon atom of the compound. The interaction of the aminoalkyl and/or aminoaryl moiety with the hydroxide moiety (which may be present, for example, as OH or O$^-$) may stabilize the compound, for example, against degradation or polymerization in solution (e.g., spontaneous polymerization in water) in certain instances. Significant or detectable degradation or polymerization in solution may be prevented, for example, by self-interaction within the compound, which may prevent or inhibit substantial and/or stable polymerization of the compound to neighboring molecules. For example, the compound may have a structure, or may be hydrolyzed or protonated within the body to form a structure such as:

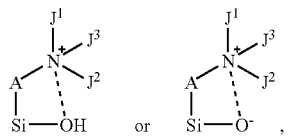

where A is any alkyl and/or aryl moiety that allows substantial interaction between the nitrogen atom and the hydroxide to occur (indicated by ------), and each of $J^1$, $J^2$, and $J^3$ independently is H or comprises at least one of a carbon atom, a nitrogen atom, an oxygen atom, or a sulfur atom. Examples of suitable alkyls include those previously described. In the above structures, not all of the atoms bonded to silicon are drawn for reasons of clarity. As an example, in an aminoalkyl moiety, the aminoalkyl moiety may include 2, 3, 4, 5, or 6 carbon atoms between the nitrogen atom and the silicon atom. In some cases the aminoalkyl moiety may be aminopropyl, aminobutyl, or aminoisobutyl, etc. Non-limiting examples of compounds having aminoalkyl moieties include the following:

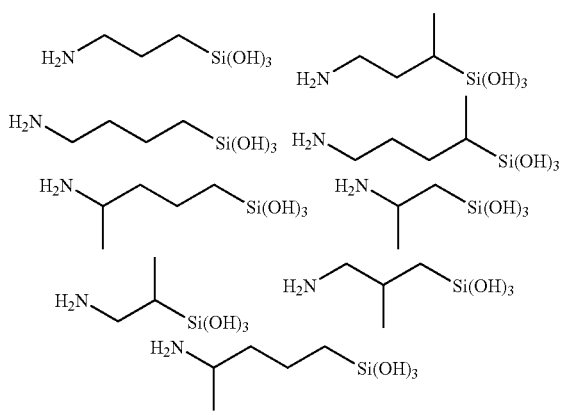

In some embodiments, the aminoalkyl moiety may include more than one amino moiety, for example, as in a bis(aminoalkyl)alkyl moiety or a tris(aminoalkyl)alkyl moiety. Examples of compounds having such structures include, but are not limited to:

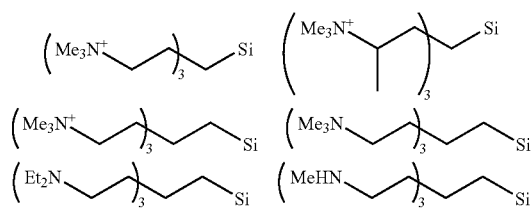

In these structures, not all of the atoms that are bonded to silicon are shown, for reasons of clarity. Combinations of these and other aminoalkyl moieties are also envisioned, for example, a bis(dimethylaminoethyl)(trimethylaminoethyl)ethyl moiety. A further example is provided by the following structures:

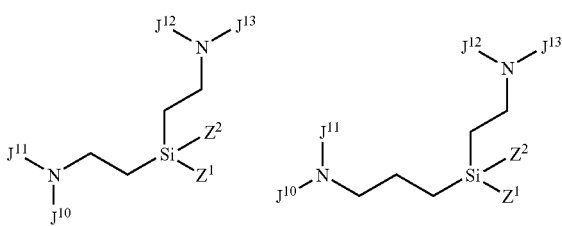

-continued

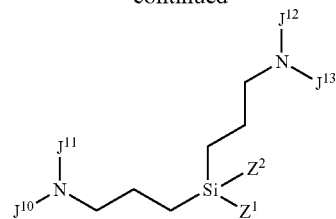

In these structures, each of $Z^1$ and $Z^2$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. Each of $J^{10}$, $J^{11}$, $J^{12}$, and $J^{13}$ is independently H or comprises at least one of a carbon atom, a nitrogen atom, an oxygen atom, or a sulfur atom. In some cases, $Z^1$ and $Z^2$ may each independently be a halogen or a pseudohalogen, such as chlorine or CN, or an alkoxy, such as methoxy. In certain embodiments, each of $J^{10}$, $J^{11}$, $J^{12}$, and $J^{13}$ may independently be an alkyl, for example, methyl, ethyl, propyl, butyl, pentyl, etc.

As another example, an aminoalkyl moiety of the compound may include a cyclic structure (i.e., an aminocycloalkyl moiety), e.g., an aryl moiety, a saturated or unsaturated cyclic moiety, a heteroaryl moiety, etc. The aminocycloalkyl moiety may optionally include one or more alkyl moieties, for example, between an aryl moiety or a cycloalkyl moiety and the silicon atom. Non-limiting examples of aminocycloalkyl compounds include:

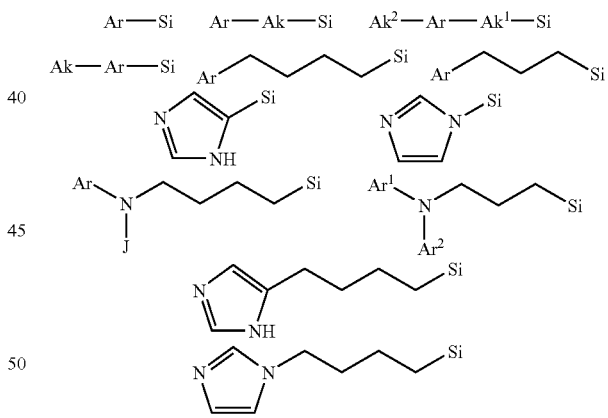

In the above structures, each Ak independently comprises an alkyl, each Ar independently comprises an aryl (for example, an aminoaryl), and J independently is H or comprises at least one of a carbon atom, a nitrogen atom, an oxygen atom, or a sulfur atom. In some cases, the silicon composition may include both aminoalkyl and aminocycloalkyl moieties, including the amines previously discussed.

In one set of embodiments, the compound is an aminosilicon compound, or a salt thereof, i.e., a compound in which a nitrogen atom is covalently bonded to a silicon atom. The compound may be, for example, a silanol, a silandiol, or a silantriol, or a compound able to form a silanol, a silandiol, or a silantriol upon hydrolysis, for example, under physiological conditions. The aminosilicon compound is cyclic in some cases. Non-limiting examples of cyclic aminosilicon compounds include:

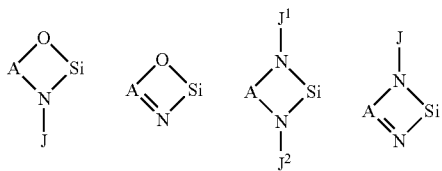

In these structures, A is a moiety having at least one of a carbon atom and a silicon atom (for example, an alkyl, a cycloalkyl, an aryl, etc.), and each J independently is H or comprises at least one of a carbon atom, a nitrogen atom, an oxygen atom, or a sulfur atom. In the above structures, not all of the atoms bonded to silicon are drawn for reasons of clarity. Specific non-limiting examples of cyclic aminosilicon compounds include:

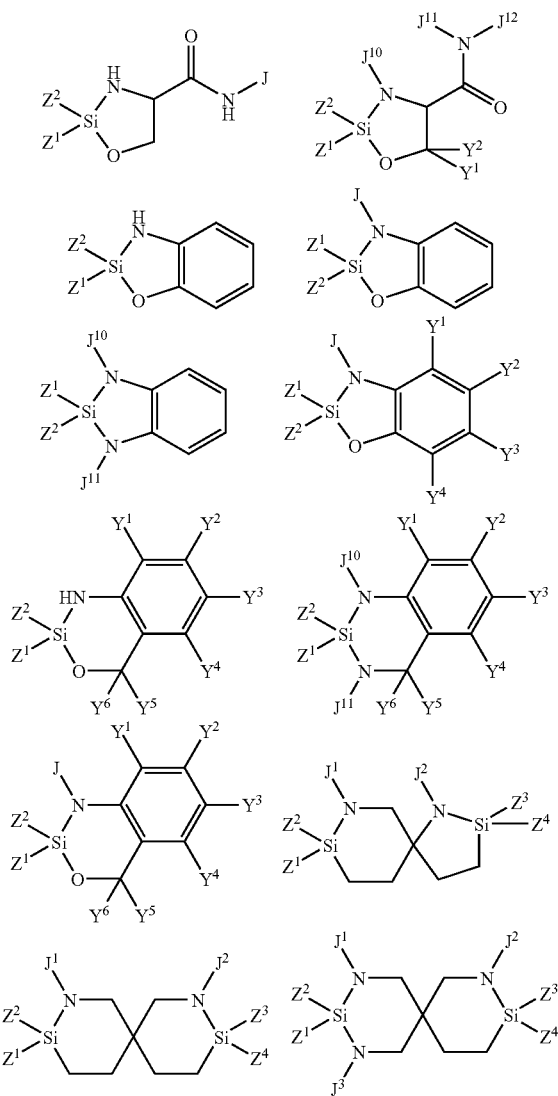

In these structures, each Z is independently one of H, X, R, OH, $OR^1$, or $NJ^1J^2$, with R comprising at least one carbon atom, X being a halogen or a pseudohalogen, $R^1$ comprising at least one carbon atom. Each J is independently H or comprises at least one of a carbon atom, a nitrogen atom, an oxygen atom, or a sulfur atom. Each Y moiety independently comprises at least one atom (for example, hydrogen, a halogen, a pseudohalogen, an alkyl moiety, an aryl moiety, a cyclic moiety, etc.).

In any of the above-described embodiments, any one, two, three, four, five, or six of $Z^1$, $Z^2$, $Z^3$, $Z^4$, $Z^5$, and $Z^6$ (where applicable) may each independently comprise a silicon atom. Thus, the compound may have at least two, at least three, at least four, at least five, etc. silicon atoms within its structure. In one embodiment, the compound is a polymer.

An example of a compound having two silicon atoms within its structure is:

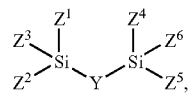

where each of $Z^1$, $Z^2$, $Z^3$, $Z^4$, $Z^5$, and $Z^6$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. Each Y moiety independently comprises at least one atom (for example, hydrogen, a halogen, a pseudohalogen, or a moiety having at least one carbon atom, for instance, an alkyl moiety, an aryl moiety, a cyclic moiety, etc.). For example, the compound may have a structure such as:

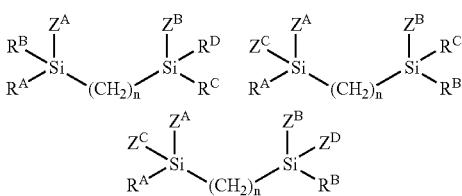

In these structures, n is any positive integer, for example, 1, 2, 3, 4, 5, 6, 7, 8, 9, 10, 11, 12, etc., each R independently comprises at least one carbon atom (e.g., an alkyl), and each Z independently is one of H, X, R, OH, $OR^1$, or $NJ^1J^2$, with R comprising at least one carbon atom, X being a halogen or a pseudohalogen (e.g., Cl, Br, I, etc.), $R^1$ comprising at least one carbon atom (e.g., an alkyl, such as methyl, ethyl, propyl, etc.), and $J^1$ and $J^2$ each independently being H, or comprising at least one of a carbon atom, a nitrogen atom, an oxygen atom, or a sulfur atom. In some cases, $R^1$ has 1, 2, 3, 4, 5, or 6 carbon atoms. In another set of embodiments, the composition includes a hydrolysis, alcoholyis, or transhalogenation derivative thereof.

As additional examples, the compound may have a structure such as the following:

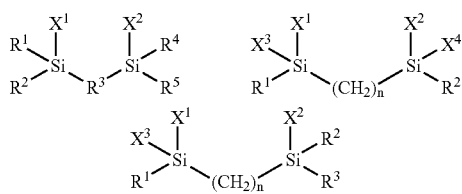

In these structures, each R independently comprises at least one carbon atom (e.g., an alkyl), and each X independently is a halogen or a pseudohalogen. Thus, in one embodiment, the compound may have a structure:

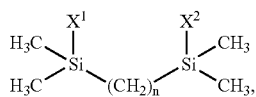

where each X independently is a halogen or a pseudohalogen, and n is any positive integer, for example, 1, 2, 3, 4, 5, 6, 7, 8, 9, 10, 11, 12, etc. For instance, in one embodiment, the compound is:

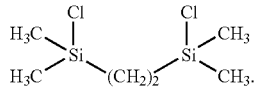

Other examples include, but are not limited to:

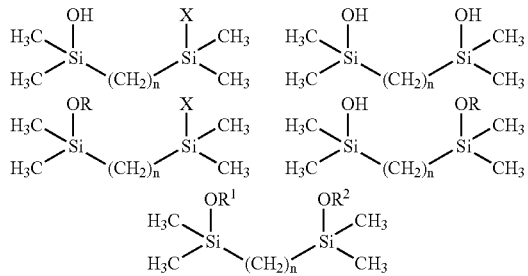

In these structures, each R independently comprises at least one carbon atom (e.g., an alkyl), each X independently is a halogen or a pseudohalogen, and n is any positive integer, for example, 1, 2, 3, 4, 5, 6, 7, 8, 9, 10, 11, 12, etc. In another set of embodiments, the composition includes a hydrolysis, alcoholyis, or transhalogenation derivative thereof.

In some cases, the compound may have a structure that allows, or can be hydrolyzed under physiological conditions to form a structure that allows, multiple silicon hydroxide moieties to simultaneously interact with aluminum, copper, ferric, ferrous, or another metal ion. Schematic non-limiting examples are illustrated below, where M indicates the position of a metal ion, and each R moiety in the illustrated structures independently comprises at least one atom interconnecting the silicon atoms (for example, an alkyl moiety, an aryl moiety, a cyclic moiety, an amine, etc.). $Z^1$ and $Z^2$ each independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. In these non-limiting examples, the (noncovalent) interaction of $SiO^-$ with the metal ion is indicated by - - - :

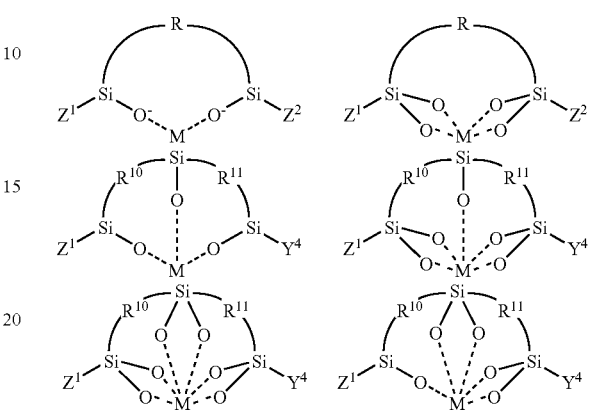

Non-limiting examples of such structures include:

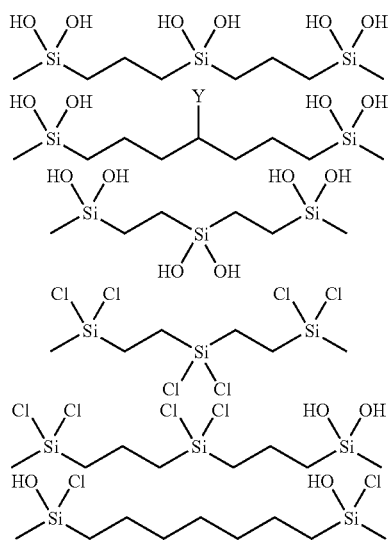

In these structures, Y comprises at least one atom (for example, hydrogen, a halogen, a pseudohalogen, an alkyl moiety, an aryl moiety, a cyclic moiety, etc.).

In certain cases, the compound is a polymer having a repeat unit comprising at least one silicon atom. In some cases, the silicon may be functionalized as described above (e.g., the silicon atom of the repeat unit may be covalently bonded to one or more of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom). For example, in one embodiment, the compound is a polymer comprising a repeat unit having silanol, silandiol, or silantriol functionality, or the polymer comprises a repeat unit that can be hydrolyzed to form silanol, silandiol, or silantriol functionality. Non-limiting examples include:

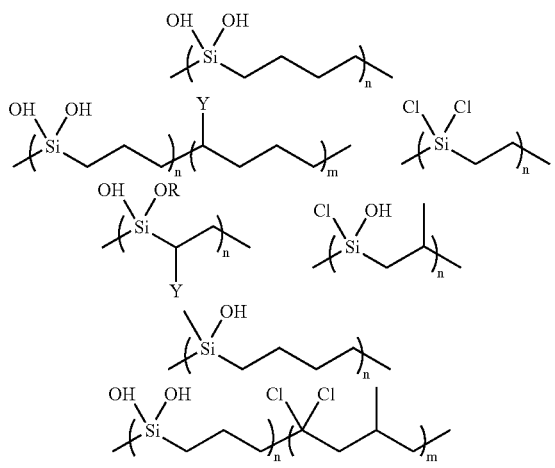

In these structures, Y comprises at least one atom (for example, hydrogen, a halogen, a pseudohalogen, an alkyl moiety, an aryl moiety, a cyclic moiety, etc.), R comprises at least one carbon atom, and n and m are positive integers. If the polymer is a copolymer (e.g., as shown above), the copolymer may be, for example, a block copolymer, a random copolymer, an alternating copolymer, a graft copolymer, etc.

In one set of embodiments, a compound of the invention is a cyclic organosilicon compound having at least one ester moiety, or a salt thereof. Non-limiting examples of such compounds include:

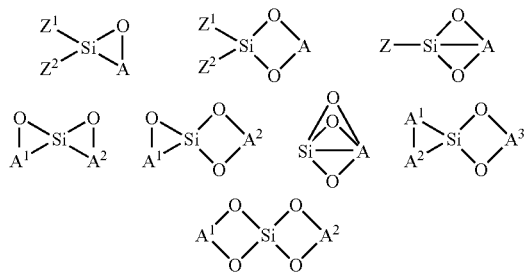

In these structures, each A independently is a moiety having at least one of a carbon atom and a silicon atom, and each Z independently is one of H, X, R, OH, OR$^1$, or NJ$^1$J$^2$, with R comprising at least one carbon atom, X being a halogen or a pseudohalogen, R$^1$ comprising at least one carbon atom, and J$^1$ and J$^2$ each independently being H, or comprising at least one of a carbon atom, a nitrogen atom, an oxygen atom, or a sulfur atom. In some cases, each A may be chosen to render the compound more hydrophobic or less hydrophobic, and/or to facilitate passage of the compound across the blood-brain barrier. Non-limiting examples of cyclic organosilicon esters of the invention include:

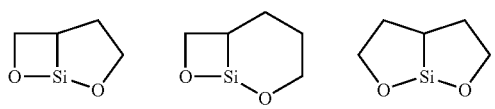

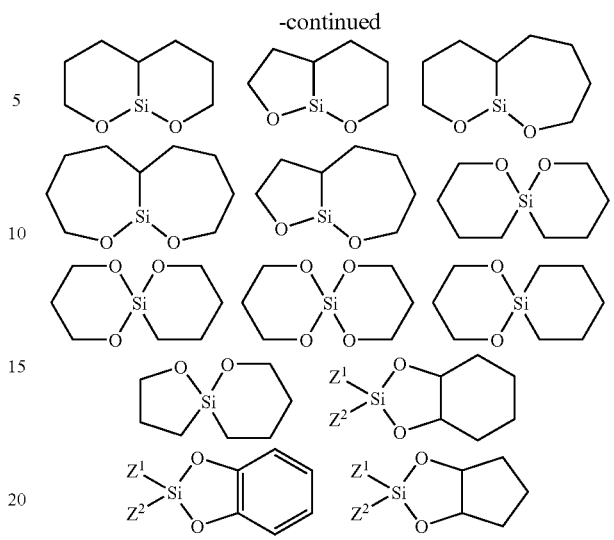

In the above structures, Z$^1$ and Z$^2$ is each independently one of H, X, R, OH, OR$^1$, or NJ$^1$J$^2$, with R comprising at least one carbon atom, X being a halogen or a pseudohalogen, R$^1$ comprising at least one carbon atom, and J$^1$ and J$^2$ each independently being H, or comprising at least one of a carbon atom, a nitrogen atom, an oxygen atom, or a sulfur atom. In the above structures, not all of the atoms bonded to silicon are drawn for reasons of clarity.

In another example, the compound has a structure:

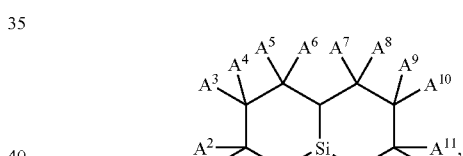

where each of A$^1$, A$^2$, A$^3$, A$^4$, A$^5$, A$^6$, A$^7$, A$^8$, A$^9$, A$^{10}$, A$^{11}$, and A$^{12}$ independently is H or comprises at least one carbon atom. Not all of the atoms bonded to silicon are drawn for reasons of clarity. In some cases, each of the A's may be chosen such that two A moieties joined by a common carbon atom of an oxasilinane ring are the same. In certain cases, each of the A's may be chosen such that the compound is symmetrical or nonchiral, or such that the compound is asymmetrical or chiral. In one embodiment, each A is either H or an alkyl moiety, such as methyl, ethyl, propyl, etc.

As previously discussed, the compound may have more than one silicon atom in some embodiments. Additional non-limiting examples include:

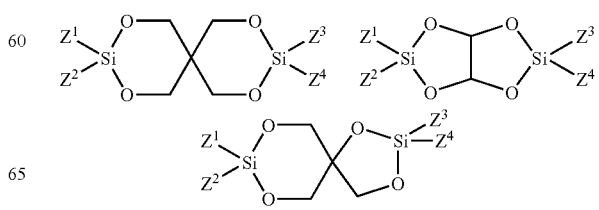

-continued

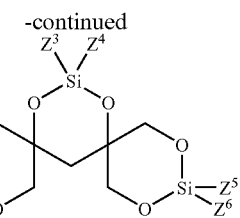

In these structures, each of $Z^1$, $Z^2$, $Z^3$, $Z^4$, $Z^5$, and $Z^6$ is independently one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom.

In yet another aspect, a compound of the invention may have a portion that becomes positively charged (represented schematically herein by the symbol

)

under physiological conditions within the body, which may thereby cause the molecule to become less charged or zwitterionic in some cases (i.e., the molecule has a positively charged portion and a negatively charged portion, or the molecule has a net dipole moment). A less charged compound may facilitate transport of the compound into the brain in some cases, for example, across the blood-brain barrier or across a cell membrane. For instance, the compound may be represented by:

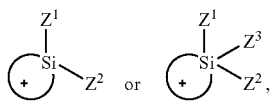

where each of $Z^1$ and $Z^2$ independently is one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. In some cases, the compound may be present as a salt.

In one set of embodiments,

is an amine moiety. For example, the nitrogen atom of the amine moiety may be located on one portion of the compound, which may give that portion of the compound a positive charge when exposed to certain physiological solutions or conditions. Examples of suitable amines include those described above. The amine may be a primary amine, a secondary amine, a tertiary amine, or a quaternary amine. For example, if the amine is a tertiary amine, the amine may be a dimethylamine, an ethylmethylamine, a propylmethylamine, a diethylamine, etc. Specific non-limiting examples include a bis(dialkylaminoalkyl)silandiol, a bis(trialkylaminoalkyl)silandiol, or a tris(trialkylaminoalkyl)silantriol. If more than one amine moiety is present within the compound, the amines may each be the same or different. Other moieties that can provide positive charge (e.g., under physiological conditions) include, for example, amidines, guanidines, aryl amines, heteroaryl amines, pyridines, imidazoles, etc. Combinations of one or more moieties that can be positively charged under physiological conditions within a compound of the invention are also envisioned, for example, a compound having an amine moiety and a guanidine moiety, a guanidine moiety and a pyridine, etc. Of course, when the molecule is charged, one or more counterions may also be present or associated with the compound, for example, an organic or an inorganic anion, such as chloride, fluoride, bromide, sulfate, carbonate, acetate, etc. if the compound is positively charged. Specific non-limiting examples of such compounds include:

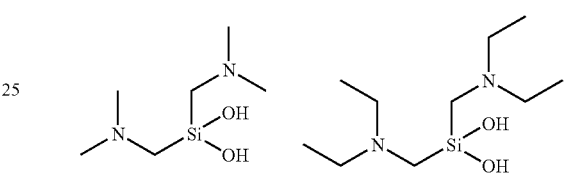

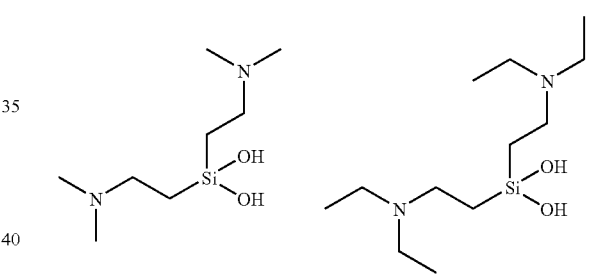

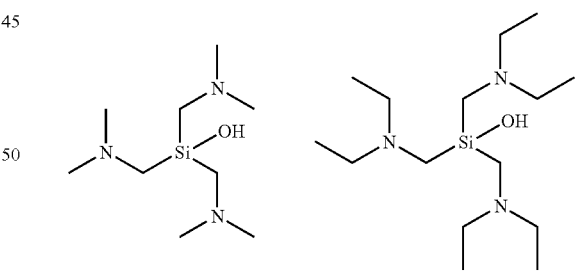

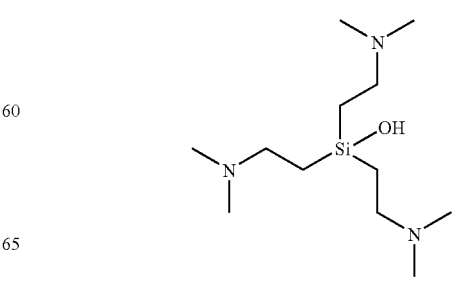

-continued

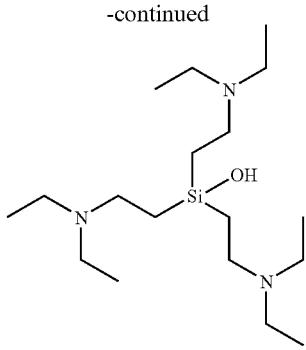

In certain embodiments of the invention a silicon-amino compound, i.e., a compound comprising at least one silicon atom, and at least one amine group is provided. In some cases, the compound may be bidentate, tridentate, or otherwise polydentate. As used herein, "dentate" is given its ordinary meaning as used in the art, i.e., a dentate moiety has one or more atoms therein that can function as an electron pair donor, thereby forming a coordinated bond. Prefixes indicate the number of bonds that the dentate moiety can form, i.e., a "bidentate" moiety can form 2 bonds, a "tridentate" moiety can form 3 bonds, a "tetradentate" moiety can form 4 bonds, etc. A "polydentate" moiety can form 2 or more such bonds. Those of ordinary skill in the art will be able to identify dentate compounds. In certain instances, the silicon-amino compound, or a portion thereof, may sequester aluminum or other ions, for example, by electrostatically binding the ions.

One example of a silicon-amino compound of the invention is represented by the structure:

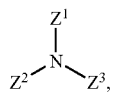

where each of $Z^1$, $Z^2$, and $Z^3$ independently is —H, an alkyl, or has a structure:

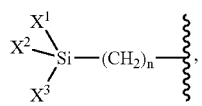

such that at least one of $Z^1$, $Z^2$, and $Z^3$ has the structure:

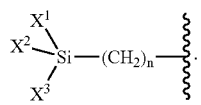

Independently, for each of $Z^1$, $Z^2$, and $Z^3$, each of $X^1$, $X^2$, and $X^3$ independently is a halogen, a pseudohalogen, an alkyl, or an alkoxy, and n is a positive integer, i.e., the moieties extending from the N atom(s) may each be the same or different. In some cases, each n can be less than or equal to 10, and in certain embodiments, each n is 1, 2, 3, 4, or 5. Each of $X^1$, $X^2$, and $X^3$ may be the same or different, and non-limiting examples of suitable moieties include halogens such as —F, —Cl, —Br, or —I, pseudohalogens, alkyls, or alkoxy moieties such as methoxy, ethoxy, propoxy, isopropoxy, butoxy, etc. In some cases, the composition includes a hydrolysis, alcoholyis, or transhalogenation derivative thereof.

For instance, in one set of embodiments, the compound has a structure:

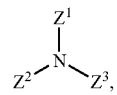

where each of $Z^1$, $Z^2$, and $Z^3$ independently is an alkyl, or has a structure:

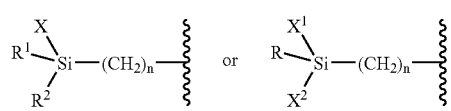

such that at least one of $Z^1$, $Z^2$, and $Z^3$ has a structure:

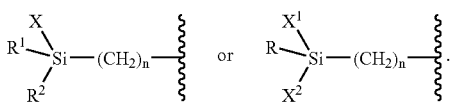

Independently, for each of $Z^1$, $Z^2$, and $Z^3$, each X in the above sub-structures independently is a halogen, a pseudohalogen, a hydroxy (—OH), or an alkoxy, and each R in the above structures independently is an alkyl. In some cases, each n can independently be less than or equal to 10, and in certain embodiments, each n is 1, 2, 3, 4, or 5. In another set of embodiments, the composition includes a hydrolysis, alcoholyis, or transhalogenation derivative thereof.

In one embodiment, the compound has a structure:

[(CH$_3$O)$_3$Si—(CH$_2$)$_3$]$_2$NH.

Another example of a silicon-amino compound of the invention is given by the structure:

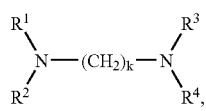

where k is a positive integer, and where each of $R^1$, $R^2$, $R^3$, and $R^4$ independently is —H or has a structure:

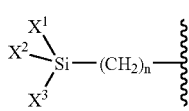

such that at least one of $R^1$, $R^2$, $R^3$, and $R^4$ has a structure:

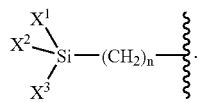

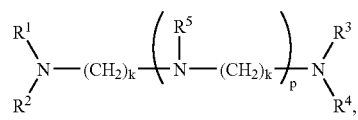

In these structures, k may be less than or equal to 10, and in certain embodiments, k is 1, 2, 3, 4, or 5. Additionally, independently for each of $R^1$, $R^2$, $R^3$, and $R^4$, each of $X^1$, $X^2$, and $X^3$ independently is a halogen, a pseudohalogen, an alkyl, a hydroxy (—OH), or an alkoxy, and n is a positive integer, i.e., the moieties extending from the N atoms may each be the same or different. In one embodiment, none of the moieties extending from the N atoms is —H. In some cases, each n can be less than or equal to 10, and in certain embodiments, each n is 1, 2, 3, 4, or 5. Each of $X^1$, $X^2$, and $X^3$ may be the same or different, and examples of X moieties include halogens such as —F, —Cl, —Br, or —I, pseudohalogens, alkyls, hydroxys, or alkoxy moieties such as methoxy, ethoxy, propoxy, isopropoxy, butoxy, etc. In some cases, the composition includes a hydrolysis, alcoholyis, or transhalogenation derivative thereof.

In one set of embodiments, the compound has a structure:

where k and p each independently are positive integers, and each of $R^1$, $R^2$, $R^3$, $R^4$, and $R^1$ independently is —H or has a structure:

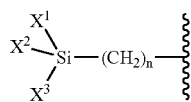

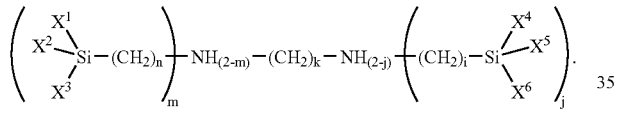

such that at least one of $R^1$, $R^2$, $R^3$, $R^4$, and $R^5$ has a structure:

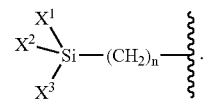

In another set of embodiments, the compound has a structure:

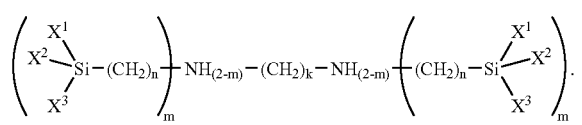

In the above structures, m is 1 or 2, j is 1 or 2, and i is a positive integer. For example, the compound may have a structure:

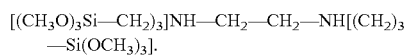

[(CH$_3$O)$_3$Si—CH$_2$)$_3$]NH—CH$_2$—CH$_2$—NH[(CH$_2$)$_3$—Si(OCH$_3$)$_3$].

In another set of embodiments, the composition includes a hydrolysis, alcoholyis, or transhalogenation derivative thereof.

In yet another example, a silicon-amino compound of the invention is polymeric. For example, the silicon-amino compound may have a structure:

In these structures, k may be less than or equal to 10, and in certain embodiments, k is 1, 2, 3, 4, or 5. Additionally, independently for each of R shown above, each of $X^1$, $X^2$, and $X^3$ independently is a halogen, a pseudohalogen, an alkyl, a hydroxy, or an alkoxy, and n is a positive integer, i.e., the moieties extending from the N atoms may each be the same or different. In one embodiment, none of the moieties extending from the N atoms is —H. In some cases, each n can be less than or equal to 10, and in certain embodiments, each n is 1, 2, 3, 4, or 5. Each of $X^1$, $X^2$, and $X^3$ may be the same or different, and examples of X moieties include halogens such as —F, —Cl, —Br, or —I, pseudohalogens, alkyls, hydroxys, or alkoxy moieties such as methoxy, ethoxy, propoxy, isopropoxy, butoxy, etc. In some instances, the composition includes a hydrolysis, alcoholyis, or transhalogenation derivative thereof.

In one set of embodiments, the compound has a structure:

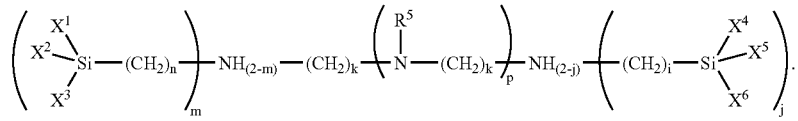

In another set of embodiments, the compound has a structure:

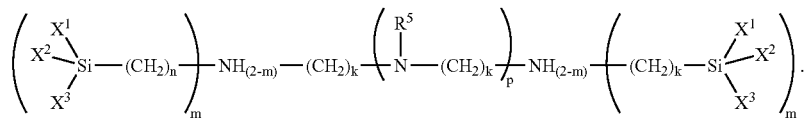

In these structures, m is 1 or 2, j is 1 or 2, and i is a positive integer. In some cases, m is equal to j. In certain cases, n is equal to j. In one embodiment, $R^5$ is —H, and in some cases, p is less than or equal to 10 or less than or equal to 5, for example, 1, 2, 3, 4, 5, etc. In another set of embodiments, the composition includes a hydrolysis, alcoholyis, or transhalogenation derivative thereof.

Non-limiting examples of techniques of making silicon-amino compound of the invention, such as the above-described compounds, include known techniques of reacting olefinic precursors with silicon halides to form an organosilicon compound, e.g., a reaction such as:

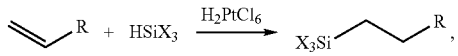

where X represents halogen atoms and/or pseudohalogens and/or alkyls (each of which may be the same or different), and R represents an organic moiety, for example, an organic moiety comprising nitrogen (e.g., an amine). In some cases, the organosilicon compound reacts with an alcohol to form a second organosilicon compound, for example as in the reaction:

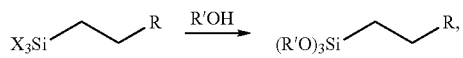

where $R^1$ represents an organic moiety (each of which may be the same as or different from the others), for instance, an alkyl such as methyl, or R' may be a hydrogen (e.g., a hydroxy).

As a specific example, if R is

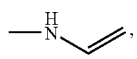

and each X is —Cl, then the reaction with $H_2PtCl_6$ is as follows:

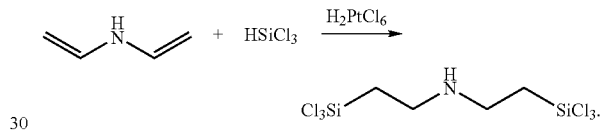

As a further example, the product of this reaction may then be reacted with methanol, thereby producing a compound:

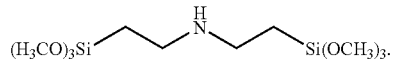

Those of ordinary skill in the art will be able to synthesize the compounds described herein, using techniques similar to those described above or straightforward modifications thereof without undue experimentation.

In another aspect, the compound may have a structure that facilitates transport of the compound into an organ or across the blood-brain barrier. In one set of embodiments, the compound may be designed so as to optimize the hydrophobicity of the composition to facilitate transport of the compound into the organ or across the blood-brain barrier (e.g., via diffusion, or using a transport system such as transport proteins or ion channels). In some cases, the compound's ability to move into the organ or across the blood-brain barrier may be lost when the compound binds to a metal ion such as aluminum, or when the compound enters the brain or other organ, or in transit (i.e., within the cells that form the blood-brain barrier, etc). In other cases, the compound may retain or improve its ability to move into an organ or cross the blood-brain barrier when bound to a metal ion. In one set of embodiments, positive, negative, and/or hydrophobic moieties may be attached to the compound so as to achieve a selected hydrophobicity and/or a selected electric dipole moment of the compound. The hydrophobicity of the compound may be determined by those of ordinary skill in the art using any suitable test, for example, by partitioning the compound in a two-phase liquid system, such as a water-octanol system, or other suitable systems known to those of ordinary skill in the art. For example, the hydrophobicity of a compound may be determined by allowing the compound to partition in a water-octanol system, and determining the percentage of the compound in the octanol phase relative to the water phase (e.g., on a per mass basis or other quantitative measurement). The water-octanol partition coefficient may be chosen such to optimize penetration of the blood-brain barrier in certain instances, and may depend on actual physiological conditions. See, e.g., Lohmann, et al., "Predicting Blood-Brain Barrier Permeability of Drugs: Evaluation of Different *In Vitro Assays*," *J. Drug Targeting*, 10 (4): 263-276, 2002. In some cases, the octanol/water partition ratio for a hydrophobic compound is at least about 1.25:1 (octanol:water), at least about 1.5:1, at least about 1.75:1, at least about 2:1, at least about 5:1, at least about 10:1, at least about 20:1, at least about 50:1, at least about 100:1, at least about 300:1, or at least about 1000:1 or greater. In some cases, a hydrophobic compound may more readily cross the blood-brain barrier or other similar barrier or membrane to enter into the brain or other organ. Thus, in one embodiment, the compound includes one or more hydrophobic or lipophilic moieties, for example, an alkyl moiety, a cycloalkyl moiety, an aryl moiety, or the like.

In another set of embodiments, a compound of the invention includes a chelating agent able to bind to aluminum, copper, iron or another metal ion (or is able to form a chelating agent able to bond to aluminum, copper, iron or another metal ion). In one embodiment, a compound of the invention has a structure:

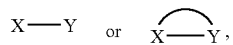

where X is a chelating agent able to bond to a metal ion, or is able to form a chelating agent able to bond to a metal ion. Additionally, Y is a structure able to facilitate transport of the compound (or a portion thereof) across the blood-brain barrier, the structure

comprises at least one chemical bond, and the structure—is a moiety that can be hydrolyzed under physiological conditions, e.g., within the brain, the blood-brain barrier, or within the bloodstream. In some cases, the structure

includes at least one atom that connects structure X and structure Y (e.g., the structure

may include two atoms bridging between X and Y, three atoms bridging between X and Y, four atoms bridging between X and Y, five atoms bridging between X and Y, etc.). Suitable hydrolyzable structures interconnecting X and Y include, for example, alkoxide moieties, ester moieties, or ether moieties, e.g., as previously described. Other suitable hydrolyzable structures will be known to those of ordinary skill in the art. In some cases, the hydrolyzable structures may be chosen to control the degradation rate of the compound within the brain (for example, if the release of Y activates X in the above structure). For example, a compound having a Si—F bond may hydrolyze at a relatively slow rate, while a compound having a Si—Cl or Si—Br bond may hydrolyze at a relatively faster rate. Slow rates of degradation may be desirable in some cases, for example, when slow or controlled release of the compound is desired. Different compounds having different halogens may also be administered together to provide short and long term activity in certain cases.

As an example, in one embodiment, Y is a targeting moiety able to target a component of the blood-brain barrier to facilitate transport, such as via an endogenous transport pathway, for example, by mimicking proteins or other substrates naturally transported by the targeted endogenous transport protein. For example, the composition may be selected to mimic a substrate for a hexose transporter, a monocarboxylate transporter, an amino acid transporter, a glucose transporter, a peptide transporter (for example, transporters for enkephalins, vasopressin, apamins, etc.), a protein transporter (e.g., transferrin), or the like. For example, a compound of the invention targeted towards transport across the blood-brain barrier using a carbohydrate transporter may have a structure such as:

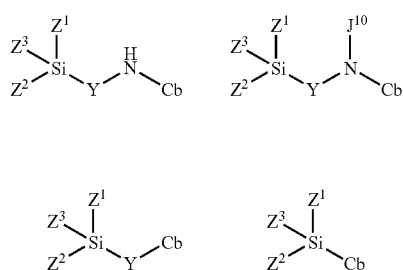

In these structures, each of $Z^1$, $Z^2$, and $Z^3$ independently is one of H, X, R, OH, $OR^1$, or $NJ^1J^2$, with R comprising at least one carbon atom, X being a halogen or a pseudohalogen, and $R^1$ comprising at least one carbon atom. Each J independently is H or comprises at least one of a carbon atom, a nitrogen atom, an oxygen atom, or a sulfur atom, Y is an interconnecting moiety (for example, an alkyl moiety, an aryl moiety, a cyclic moiety, etc.), and Cb comprises a carbohydrate moiety (or a portion thereof). In some cases, Cb is an entity that substantially derives from a carbohydrate or a portion thereof. For example, a reaction of a carbohydrate with an aminosilicon composition or an amidated silicon compound may be used to produce a composition of the compound. In some cases, the carbohydrate may be an aldehyde sugar ("aldocarbose") (e.g., aldohexose or aldopentose) or a ketone sugar ("ketocarbose") (e.g., ketohexose or ketopentose), or a moiety derived from an aldocarbose or a ketocarbose. For example, the carbohydrate may be amidated, aminated, esterified, etc. Other carbohydrate derivitization reactions will be known to those of ordinary skill in the art. In some cases, at least a portion of the carbohydrate may be an aldehyde sugar or a ketone sugar.

As another example, the composition may have a structure such as:

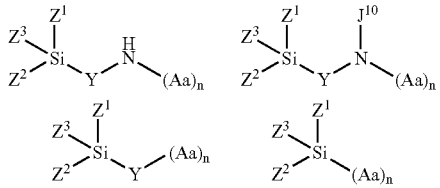

In these structures, each of $Z^1$, $Z^2$, and $Z^3$ independently is one of a H, X, R, OH, $OR^1$, or $NJ^1J^2$, with R comprising at least one carbon atom, X being a halogen or a pseudohalogen, and $R^1$ comprising at least one carbon atom. Also, each J independently is H or comprises at least one of a carbon atom, a nitrogen atom, an oxygen atom, or a sulfur atom, Y is an interconnecting moiety (for example, an alkyl moiety, an aryl moiety, a cyclic moiety, etc.), and Aa comprises one or more amino acids (i.e., n may be 1, 2, 3, a peptide, a protein, etc.) and/or one or more amino acid derivatives. In some cases, n may be a positive integer less than about 50, less than about 20, or less than about 10.

Such compounds may be prepared, for example, by reacting a suitable aminosilicon compound with a carbohydrate, an amino acid, a peptide, a protein, a hormone, a neurotransmitter, etc. using coupling reactions known to those to ordinary skill in the art.

In another set of embodiments, a compound of the invention may be packaged or included in a virus, for example, a virus that is targeted towards the brain or other organ. For example, a virus may be loaded with a silanol, a silandiol, or a silantriol, and/or a compound able to form a silanol, a silandiol, or a silantriol upon hydrolysis and/or release from the virus. In some cases, the viruses may be prepared by assembling the viral envelope of the virus in the presence of one or more compounds of the invention, thus facilitating internal loading of the virus with the compounds of the invention.

In yet another aspect, the compound may have a detectable moiety, i.e., a moiety that facilitates external detection, e.g., in vivo or in vitro. For example, a portion of the compound may be radioactively and/or fluorescently labeled. Such compounds can be prepared using coupling reactions known to those of ordinary skill in the art. As an example, a compound having a structure:

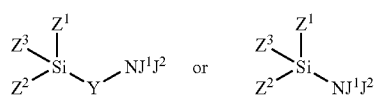

may be reacted with an acyl, isocyanate, or an isothiocyanate moiety on, or attached to, a fluorescent moiety, thereby producing a detectable compound. As another example, a compound having a structure:

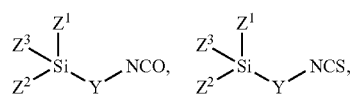

-continued

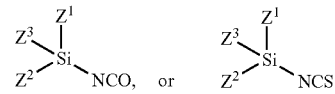

may be reacted with an $NH_2$, a SH, or an OH moiety on, or attached to, a fluorescent moiety to produce a detectable compound. In the above structures, each Z is independently one of H, X, R, OH, $OR^1$, or $NJ^1J^2$, with R comprising at least one carbon atom, X being a halogen or a pseudohalogen, $R^1$ comprising at least one carbon atom, and $J^1$ and $J^2$ each independently being H, or comprising at least one of a carbon atom, a nitrogen atom, an oxygen atom, or a sulfur atom. Y is a moiety interconnecting Si and N (for example, an alkyl moiety, an aryl moiety, a cyclic moiety, etc.). Those of ordinary skill in the art will know of suitable fluorescent labels for use in the above structures. As one particular example, the fluorescent label may be FITC or a FITC derivative, fluorescein, GFP, etc.

The detectable moiety, in another set of embodiments, includes a radioactive atom, for example, $^3H$, $^{14}C$, $^{33}P$, $^{32}P$, $^{125}I$, $^{131}I$, $^{35}S$, etc. Those of ordinary skill in the art will know of suitable ways to incorporate a radioactive label into a compound of the invention. As one particular example, if the detectable moiety is tritium (3H or T), tritium can be incorporated into the compound using a reducing reaction. For example, a tritiated lithium aluminum hydride (e.g., $LiAlT_4$, $LiAlHT_3$, $LiAlH_2T_2$, and/or $LiAlH_3T$) may be reacted with a functional moiety, resulting in reduction of the functional moiety and incorporation of a tritium label into the compound. Non-limiting examples of useful reducing reactions include:

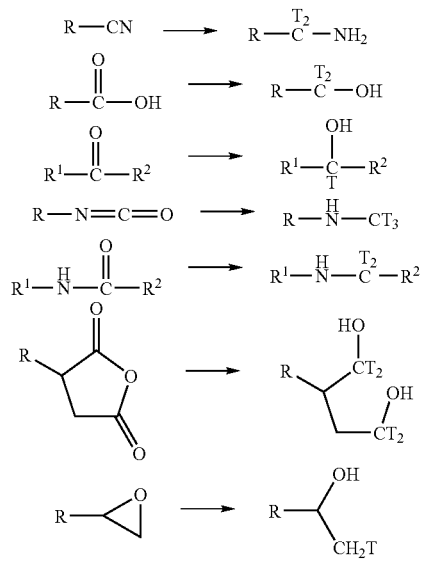

In the above structures, each R (or, for structures with $R^1$ and $R^2$, at least one of $R^1$ and $R^2$) comprises at least one silicon atom. It should be understood that, for any T in the above structure, the actual reaction products will include a mixture of labeled (tritiated) and unlabeled hydrogen atoms.

In one aspect of the invention, the compositions of the invention may be assayed for transport across subject cells. In one set of embodiments, the cells are cells that can be used to model the blood-brain barrier, for example, Caco-2 cells or bMVEC cells ("bovine microvascular epithelial cells"). For example, transport of a composition of the invention across a monolayer of the cells may be used to determine or predict the transport or uptake rate of the composition (or a portion thereof) across the blood-brain barrier. Transport of the composition may be determined, for example, using CD or similar techniques, such as atomic absorption, spectroscopy, mass spectroscopy, radioactive tracer measurements, or the like. In some cases, a composition of the invention may be determined by its transport behavior across a monolayer of cells, i.e., a composition of the invention may be transported across the cell monolayer at a substantial rate. Thus, a composition "able to cross" the blood-brain barrier (or other membrane) may be determined, in some cases, by the compound's ability to cross a monolayer of cells, such as Caco-2 cells or bMVEC cells. Other examples of suitable cell models are described in Lohmann, et al., "Predicting Blood-Brain Barrier Permeability of Drugs: Evaluation of Different *In Vitro Assays*," *J. Drug Targeting,* 10 (4): 263-276, 2002.

In another set of embodiments, the toxicity of a test compound against cells such as human cells is determined. A step of selecting test compounds that are substantially non-toxic to subject cells is provided. "Substantially non-toxic," as used herein means that the test compound can be administered to a subject with an acceptable amount of damage (preferably, no detectable damage) to the subject cells. The damage to the cells may be indicated by altered cell metabolism, cell morphology, cell mitosis, necrosis, apoptosis, etc. An acceptable amount of damage can be determined by one of skill in the art with no more than routine experimentation. Acceptable amounts of damage may depend on route of administration, risk of side effects versus benefit of administration, etc.

In another aspect, the compositions and methods of the invention may be used in diagnostic or assay techniques. For example, a composition of the invention may be used in an assay such as an aluminum detection assay or a metal ion detection assay. A sample having a known or unknown concentration of aluminum, copper, iron or other metal ion may be added to a solution containing a composition of the invention, and the amount or degree of binding of the composition (or a portion thereof) to the metal ion may be determined, using techniques known by those of ordinary skill in the art, for example, using circular dichroism or mass spectroscopy. As another example, the invention may be used in a cell culture system, for example, in a cell culture that includes neural and/or other types of cells, such as a cell able to produce A-beta$_{1-42}$ (A$\beta_{1-42}$) peptide and/or a tau protein. In one set of embodiments, a composition of the invention is added to a cell culture, optionally with a known or unknown concentration of metal ion, and the net effect on cell function of the combination of the metal ion and the organosilicon composition of the invention is determined using techniques known to those of ordinary skill in the art. In another set of embodiments, a cell culture is used to detect and/or determine the concentration of metal ion in a sample using the methods and compositions of the invention, which may be a sample of biological origin in some cases. In one embodiment, a cell culture, a diagnostic, or an assay may be used to determine proper dosing to achieve a certain specified result (e.g., a certain concentration of free metal ions) when the composition is applied to a subject.

Another aspect of the invention provides a method of administering a composition of the invention to a subject. When administered, the compositions of the invention are applied in a therapeutically effective, pharmaceutically acceptable amount as a pharmaceutically acceptable formulation. As used herein, the term "pharmaceutically acceptable" is given its ordinary meaning as used in the art. Pharmaceutically acceptable compounds are generally compatible with other materials of the formulation and are not generally deleterious to the subject. A composition of the invention (or prodrug form of the composition) may be administered to the subject in any therapeutically effective dose or treatment. A "therapeutically effective" dose or amount is capable of at least partially preventing or reversing symptoms related to the adverse effects of metal ions as previously discussed, for example, neurofibrillary tangles or senile plaque formation in the brain. A therapeutically effective amount may be determined by those of ordinary skill in the art, for instance, employing factors such as those further described below and using no more than routine experimentation.

In administering the compositions of the invention to a subject, dosing amounts, dosing schedules, routes of administration, and the like may be selected so as to affect known activities of the compositions of the invention. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day. In some cases, parenteral administration of the composition may be from one to several orders of magnitude lower dose per day, as compared to oral doses. In the event that the response of a particular subject is insufficient at such doses, even higher doses (or effectively higher doses by a different, more localized delivery route) may be employed to the extent that subject tolerance permits. Multiple doses per day are also contemplated, in certain cases, to achieve appropriate levels of the composition within the subject or within the active site of the subject, such as within the brain.

The dose of the composition to the subject may be such that a therapeutically effective amount of the composition (or a portion thereof, such as an organosilicon compound) reaches or enters the brain or other active site. The dosage may be given in some cases at the maximum amount while avoiding or minimizing any potentially detrimental side effects to the subject. For example, the dose of the organosilicon composition may be about 0.1 mcmol/kg ("micromoles"/kg) to about 50 mcmol/kg, or about 0.5 mcmol/kg to about 5.0 mcmol/kg. The dosage of the composition that is actually administered is dependent upon factors such as the final concentration desired at the active site, the method of administration to the subject, the efficacy of the composition, the longevity (i.e., half-life) within the subject of the composition, the timing of administration relative to the formation of the tangles and/or plaques the frequency of treatment, the effect of concurrent treatments, etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition (or portion thereof) at the active site. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

The specific dosage(s) given to the subject can thus be determined by those of ordinary skill in the art, using no more than routine experimentation.

Administration of the compositions of the invention may be accomplished by any medically acceptable method which allows the composition (or portion thereof) to reach its target. The particular mode selected will depend, of course, upon factors such as the particular composition, the severity of the state of the subject being treated, or the dosage required for therapeutic efficacy. As used herein, a "medically acceptable" mode of treatment is a mode able to produce effective levels of the composition (or portion thereof) within the subject, without causing clinically unacceptable adverse effects. A "target" or "active site" is the location where a composition (or portion thereof) of the invention is able to bind to a metal ion and/or inhibit interaction between the metal ion and components of the body adversely affected by the presence of the metal ion, such as with A-beta$_{1-42}$ peptide or tau proteins. The inhibition of the metal ion may occur before or after the metal ion complexes or otherwise inactivates such components adversely affected. Non-limiting examples of such targets include the bloodstream or the brain.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally through parenteral injection or implantation, via surgical administration, or any other method of administration where access to the target by the composition of the invention is achieved. As another example, any of the compositions described herein may be injected directly into the brain, spinal cord, or other organ, or the composition may be injected in a region such that it will be transported into the brain, spinal cord, or other organ, for example, injected into the cerebrospinal fluid. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. In one embodiment, the implantable delivery system is a subdural article containing the organosilicon composition, placed in direct contact with the brain, for example, through surgery. The article may have any suitable form for implantation within the brain, for example, a sponge, a film, a blanket, a pad, a wafer, a disc, etc. In certain cases, the article may be removed (and optionally replaced with a new article) after a suitable period of time has passed, for example, after a fixed time, such as a day, a week, or a month. In certain instances, the article may be removed when a certain condition is reached, for example, once a certain amount or percentage of the composition has diffused out of the article and/or when a certain amount of metal has been bound to the article. In other cases, the article may be allowed to remain within the subject indefinitely. For example, a sponge may include one or more compositions of the invention, which may be released from the sponge upon implantation, or which may remain mobilized within the sponge.

Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the active compound of the composition. Other oral compositions suitable for use with the invention include solutions or suspensions in aqueous or non-aqueous liquids such as a syrup, an elixir, or an emulsion. In another set of embodiments, the composition may be used to fortify a food or a beverage.

In certain embodiments of the invention, the administration of the composition of the invention may be designed so as to result in sequential exposures to the composition over a certain time period, for example, hours, days, weeks, months or years. This may be accomplished by repeated administrations of the composition by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases, for example, to allow for scavenging of metal ions such as aluminum, copper or iron throughout the body, and promoting excretion of the metal ions via the kidney and bowel, or to allow for reaction with components of the body adversely affected by the metal ions, such as neurofibrillary tangles or senile plaque. However, avoidance of short-term elevated levels of compositions within the body may be desired in some cases, for instance, to minimize the precipitation of silicate kidney stones in the presence of non-physiological levels of silicon and silicon-containing compounds.

Other delivery systems suitable for use with the present invention (e.g., where alteration and/or control of the release kinetics is desired) include time-release, delayed release, sustained release, or controlled release delivery systems. Such systems may avoid repeated administrations of the composition in many cases, increasing convenience to the subject. Many types of release delivery systems are available and known to those of ordinary skill in the art. They include, for example, polymer-based systems such as polylactic and/or polyglycolic acids, polyanhydrides, polycaprolactones and/or combinations of these; nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, and 5,736,152), or diffusional systems in which an active component controls the release rate (for example, as described in U.S. Pat. Nos. 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In certain embodiments of the invention, the composition of the invention is administered to subjects who have a family history of Alzheimer's disease or other disease that is characterized by an excess of metal ions, or to subjects who have a genetic predisposition for the disease. In other embodiments, the composition is administered to subjects who have reached a particular age, or to subjects more likely to get the disease. In yet other embodiments, the composition may be administered to subjects who exhibit symptoms of the disease (e.g., early or advanced). In still other embodiments, the composition may be administered to subjects as a preventive measure. In some embodiments, the composition is administered to subjects based on demographics or epidemiological studies, for example, to persons living in a certain geographic area, such as areas where a high concentration of metal ions are present in the groundwater; or to persons in a particular field, for example, workers in the aluminum, copper, iron or lead industry, or workers who use aluminum, copper or iron compounds or materials.

Alzheimer's disease may be characterized in a subject by those of ordinary skill in the art prior to treatment with the compositions of the invention. For example, a biological sample for the subject such as a blood test, a urine test, a biopsy, a spinal tap, etc., may be analyzed using an appropriate analytical technique and a concentration of ions (e.g. metal ions such as aluminum, copper or iron) may be determined and compared to normal values. For example, an ion concentration may be determined by NMR, mass spectrometry, ICP, emission spectroscopy, fluorescence spectrometry, ELISA, a chemical stain or indicator, etc. As another example, a subject may be directly tested to determine if a disease exists or may exist (i.e., the subject is susceptible to the disease), for example, using MRI, CAT scans, X-rays, etc. In another set of embodiments, a subject may be diagnosed as having or being at risk for Alzheimer's disease by a medical professional using routine practice. Alzheimer's disease may be diagnosed, for example, by considering the medical history, including such information as the person's general health, past medical problems, and/or any difficulties the subject has in performing carrying out daily activities; medical tests such as tests of blood, urine, or spinal fluid; neuropsychological tests such as memory, problem solving, attention, counting, and language tests; and/or brain scans, for example, using electroencephalograms, MRI, CAT, or PET scans; and behavioral indicators such as memory loss, personality change, dementia, speech problems, cognitive or reasoning problems, eating problems, incontinence, motor control problems, etc. Research studies have also indicated a general decrease in cerebrospinal fluid (CSF) A-beta$_{1-42}$ levels with an increase in tau protein may be indicative of a subject having or at risk for disease.[1] An improvement or arresting of at least some of the above indications may be related to the effectiveness of the inventive compositions. Of course, effectiveness may be measured by any of the techniques known to those skilled in the art, including, but not limited to, those listed above.

[1] Harrison's Principles of Internal Medicine, 15$^{th}$ Edition, CD-ROM, McGraw-Hill, 2001

Administration of the compositions of the invention (or prodrug form of the composition) can be alone, or in combination with other therapeutic agents and/or compositions (e.g., other agents or compositions that can be used to treat Alzheimer's disease or other disease that is characterized by an excess of metal ions). In certain embodiments, the compositions of the invention can be combined with a suitable pharmaceutically acceptable carrier, for example, as incorporated into a liposome, incorporated into a polymer release system, or suspended in a liquid, e.g., in a dissolved form or a colloidal form. The carrier may be either soluble or insoluble, depending on the application. Compositions of the invention that may be pharmaceutically acceptable include not only the active compound, but also formulation ingredients such as salts, carriers, buffering agents, emulsifiers, diluents, excipients, chelating agents, drying agents, antioxidants, antimicrobials, preservatives, binding agents, bulking agents, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or alginic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation. In some cases, the pharmaceutically acceptable carrier(s) may be formulated such that the pH of the carrier(s) is at a desired value, e.g., through the use of buffering agents as described above. For example, the pH may be selected to prevent hydrolysis of a composition of the invention, or the conversion of a halogen group, alkyl group, etc., to a hydroxy group. In some embodiments of the invention, generally high pH values are desired, e.g., a pH of at least about 9, at least about 10, at least about 11, at least about 12, or at least about 13. In other embodiments, however, generally low pH values may be desired, e.g., a pH of less than about 5, less than about 4, less than about 3, less than about 2, or less than about 1. A neutral pH may also be desired in some cases, e.g., a pH of between about 5 and 9, or a pH of between about 6 and 8.

In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. The term "carrier" denotes an organic or inorganic ingredient, which may be natural or synthetic, with which one or more active compounds of the invention are combined to facilitate the application of the composition. The carrier may be co-mingled or otherwise mixed with one or more active compounds of the present invention, and with each other, in a manner such that there is no interaction which would substantially impair the desired pharmaceutical efficacy. Pharmaceutically acceptable carriers include, for example, diluents, emulsifiers, fillers, salts, buffers, excipients, drying agents, antioxidants, preservatives, binding agents, bulking agents, chelating agents, stabilizers, solubilizers, silicas, and other materials well-known in the art.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, peanut oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and/or other additives may also be present such as, for example, antimicrobials, antioxidants, chelating agents and inert gases and the like. Those of skill in the art can readily determine the various parameters for preparing and formulating the compositions of the invention without resort to undue experimentation.

In some embodiments, the present invention includes a step of bringing a composition or compound of the invention into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, a compound of the present invention may be present as a pharmaceutically acceptable salt. The term "pharmaceutically acceptable salts" includes salts of the compound, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

In one aspect of the invention, the composition comprises homologs, analogs, derivatives, enantiomers and/or functionally equivalent compositions thereof of the compounds of the invention, such as any of the above-described compounds. Such homologs, analogs, derivatives, enantiomers and functionally equivalent compositions thereof of the compounds may be used in any of the assays, methods, or compositions described above that are able to detect or treat Alzheimer's disease or other diseases characterized by the presence of metal ions. "Functionally equivalent" generally refers to a composition capable of treatment of a subject that exhibits symptoms of Alzheimer's disease or other diseases characterized by the presence of metal ions, a subject susceptible to or otherwise at increased risk for such diseases, or a subject not exhibiting symptoms of such diseases, but for whom it is desired to decrease the risk of such diseases (e.g., a vaccination or a prophylactic treatment). It will be understood one of ordinary skill in the art will be able to manipulate the conditions in a manner to prepare such homologs, analogs, derivatives, enantiomers and functionally equivalent compositions. Thus, homologs, analogs, derivatives, enantiomers and/or functionally equivalent compositions which are about as effective or more effective than the parent compound are also intended for use in the methods of the invention. Synthesis of such compositions may be accomplished through typical chemical modification methods such as those routinely practiced in the art.

Another aspect of the present invention involves a method comprising providing any of the compositions of the present invention (or portions thereof), and performing a combinatorial synthesis on the composition, preferably to obtain homologs, analogs, derivatives, enantiomers and functionally equivalent compositions thereof of the composition. An assay may be performed with the homolog, analog, derivative, enantiomer or functionally equivalent composition to determine its effectiveness in treating, preventing, or inhibiting Alzheimer's disease or other diseases characterized by the presence of metal ions. The combinatorial synthesis can involve subjecting a plurality of the compositions described herein to combinatorial synthesis, using techniques known to those of ordinary skill in the art.

The present invention also provides any of the above-mentioned compositions useful for the treatment of Alzheimer's disease or other diseases characterized by the presence of metal ions packaged in kits, optionally including instructions for use of the composition for the treatment of such diseases. That is, the kit can include a description of use of the composition for participation in any biological or chemical mechanism disclosed herein associated with Alzheimer's disease or other diseases characterized by the presence of metal ions. The kit can include a description of use of the compositions as discussed herein. The kit also can include instructions for use of a combination of two or more compositions of the invention. Instructions also may be provided for administering the drug by any suitable technique, as described above.

The invention also involves, in some embodiments, the promotion of the treatment of Alzheimer's disease or other diseases characterized by the presence of metal ions according to any of the techniques and compositions described herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, replacing, or the like that can be associated with the methods and compositions of the invention, e.g., as discussed herein. Promoting may also include, in some cases, seeking approval from a government agency to sell a composition of the invention for medicinal purposes. Methods of promotion can be performed by any party including, but not limited to, businesses (public or private), contractual or subcontractual agencies, educational institutions such as colleges and universities, research institutions, hospitals or other clinical institutions, governmental agencies, etc. Promotional activities may include instructions or communications of any form (e.g., written, oral, and/or electronic communications, such as, but not limited to, e-mail, telephonic, facsimile, Internet, Web-based, etc.) that are clearly associated with the invention. As used herein, "instructions" can define a component of instructional utility (e.g., directions, guides, warnings, labels, notes, FAQs ("frequently asked questions"), etc., and typically involve written instructions on or associated with the composition and/or with the packaging of the composition, for example, use or administration of the composition, e.g., in the treatment or prevention of Alzheimer's disease or other diseases characterized by the presence of metal ions. Instructions can also include instructional communications in any form (e.g., oral, electronic, digital, optical, visual, etc.), provided in any manner such that a user will clearly recognize that the instructions are to be associated with the composition, e.g., as discussed herein.

A "kit," as used herein, defines a package including any one or a combination of the compositions of the invention, and/or homologs, analogs, derivatives, enantiomers and functionally equivalent compositions thereof, and the instructions, but can also include the composition of the invention and instructions of any form that are provided in connection with the composition in a manner such that a clinical professional will clearly recognize that the instructions are to be associated with the specific composition, for example, as described above. The kits described herein may also contain, in some cases, one or more containers, which can contain compositions such as those described above. The kits also may contain instructions for mixing, diluting, and/or administrating the composition. The kits also can include other containers with one or more solvents, surfactants, preservative and/or diluents (e.g., normal saline (0.9% NaCl), or 5% dextrose) as well as containers for mixing, diluting or administering the composition to the subject.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the formulation of the composition and the mode of use or administration. Suitable solvents for drug compositions are well known and are available in the literature.

The kit, in one set of embodiments, may comprise a carrier that is compartmentalized to receive in close confinement one or more container means such as vials, tubes, and the like, each of the compartments comprising one of the separate elements to be used in the method. For example, one of the compartments may comprise a positive control for an assay. Additionally, the kit may include containers for other components of the compositions, for example, buffers useful in the assay.

The function and advantage of these and other embodiments of the present invention will be more fully understood from the examples below. The following examples are intended to illustrate the benefits of the present invention, but do not exemplify the full scope of the invention.

EXAMPLE 1

In this example, circular dichroism (CD) was used to monitor changes in conformation of model peptides from human A-beta$_{1-42}$ peptide (SEQ ID NO: 1) (FIG. 1) when exposed to certain compounds of the present invention. These compounds included certain hydroxy derivatives of organosilanes, as well as the monols, diols and triols of certain organosilicon compounds. These compounds were tested for their ability to restore the CD spectrum of NF-M17 to its original shape.

The experiments were performed as follows. Peptides containing a seventeen amino acid region of the human neurofilament mid-sized subunit protein, NF-M17 were synthesized at greater than 95% purity. For the CD titration, the peptides were dissolved in 2,2,2-trifluoroethanol (TFE) to a concentration of 0.4 mg/ml (0.2 mM). The aluminum solution (20 mM) was also prepared in TFE. Sodium metasilicate and the orthosilicate were dissolved in water. The sodium metasilicate solution was acidified to pH 6.0. The initial CD spectra collected contained primarily only information about the peptide. Incremental additions of aluminum ion were made until 8 equivalents (addition of 8 microliters) of the metal ion were added to the solution containing the peptide. The maximum conformational change at 8 equivalents of aluminum was then titrated with $SiO_4^{4-}$. Additions to the solution were made as increments of peptide molar equivalents and did not exceed 32 equivalents. After each addition, the CD spectrum was collected and analyzed.

The following silantriols or their precursors were tested: 3-aminopropylsilantriol (APST), 3-(trihydroxysilyl)propyl-methylphosphonate sodium salt (TSPMP), n-octyltrichlorosilane (OTCS) after hydrolysis in water, and 3-cyanopropyltrichlorosilane (CPTCS), after hydrolysis in water. The following silandiols or their precursors were also tested in this example: diphenylsilandiol (DPSD), hexylmethyldichlorosilane (HMDS), methylphenyldichlorosilane (MPDS), dichlorodiethylsilane (DCDES), dichlorodiisopropylsilane (DCDIPS), and (dichloro)methylsilylbutyronitrile (DCMSBN). The following silanols or their precursors were also tested: potassium trimethylsilanolate (PTMS), tert-butyldimethylsilanol (TBDMS), triethylsilanol (TES), and benzyldiethylsilanol (BDS). APST, DPSD, and APTES were obtained from Gelest, Inc. (Tullytown, Pa.). TFE, TSPMP, PTMS, TBDMS, TES, TPS, DCDIPS, DCDES, DCMSBN, and BDS were obtained from Sigma-Aldrich (St. Louis, Mo.). OCS and CPTCS were obtained from Lancaster Synthesis (Windham, N.H.). These structures are shown in FIG. 2.

APST (FIG. 2A), TSPMP (FIG. 2B), PTMS (FIG. 2K), TBDMS (FIG. 2L), TES (FIG. 2M), and BDS (FIG. 2N) were each dissolved to a final concentration of 20 mM in TFE. The addition of 2 microliters to 100 microliters of peptide solution represented 2 equivalents.

OTCS (FIG. 2C), CPTCS (FIG. 2D), HMDS (FIG. 2F), DCDES (FIG. 2H), DCDIPS (FIG. 2I), and DCMSBN (FIG. 2J) were each hydrolyzed in water and diluted to a final concentration of 20 mM. MPDS was first dissolved in 50% TFE in water and then made up to a final concentration of 20 mM. MPDS (FIG. 2G) was first dissolved in 50% TFE in water and diluted to final concentration of 20 mM. DPSD (FIG. 2E) was first dissolved in dimethyl sulfoxide (DMSO) and then made up to a final concentration of 20 mM in TFE. DMSO blanks (containing no peptide) were collected for each dilution (0.04% to 1%).

Figure 3A:
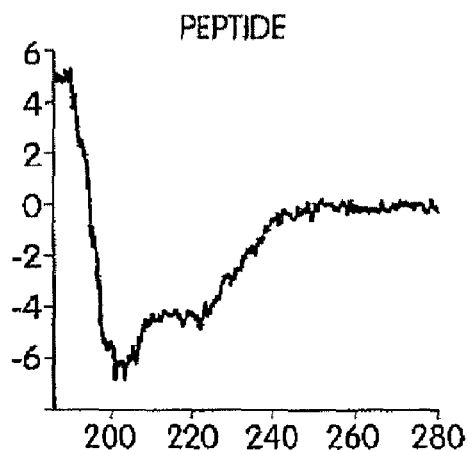
FIGS. 3A-3D illustrate the effect of sodium metasilicate hydrate on the neurofilament of FIG. 1, as indicated by circular dichroism (CD) data plotted as ellipticity vs. wavelength.
Figure 3B:
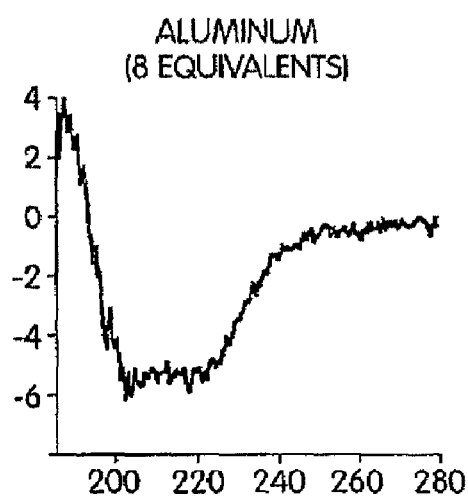
Figure 3C:
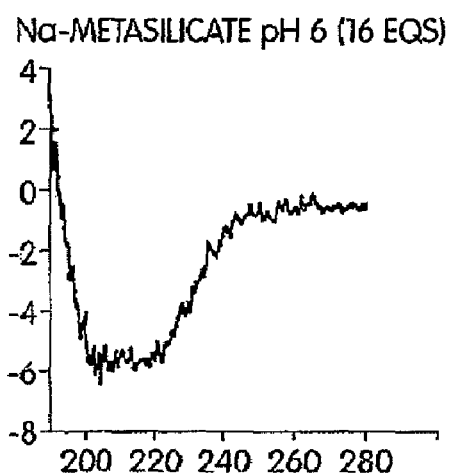
Figure 3D:
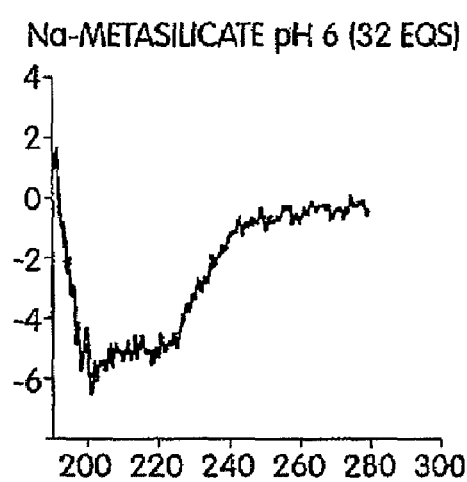
Figure 4A:
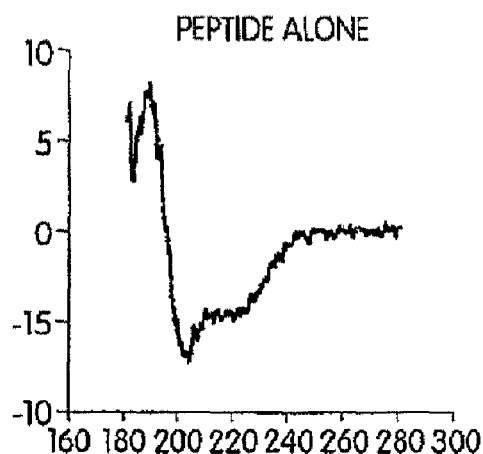
FIGS. 4A-4E illustrate the effect of sodium orthosilicate on the peptide of FIG. 1, as indicated by CD data.
Figure 4B:
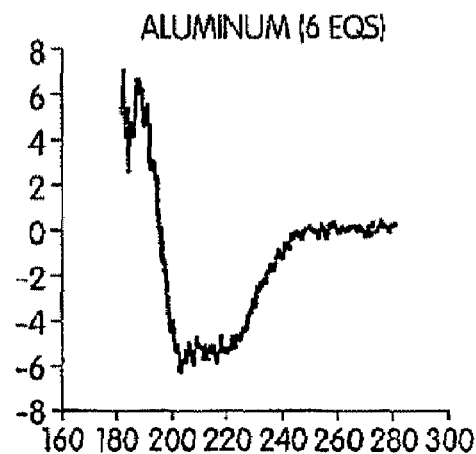
Figure 4C:
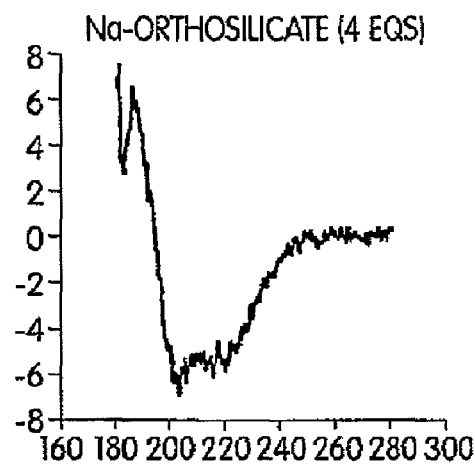
Figure 4D:
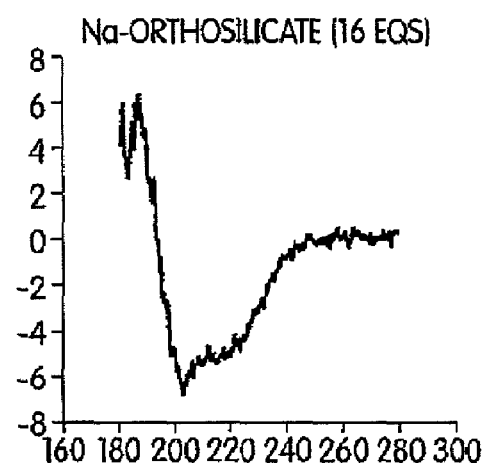
Figure 4E:
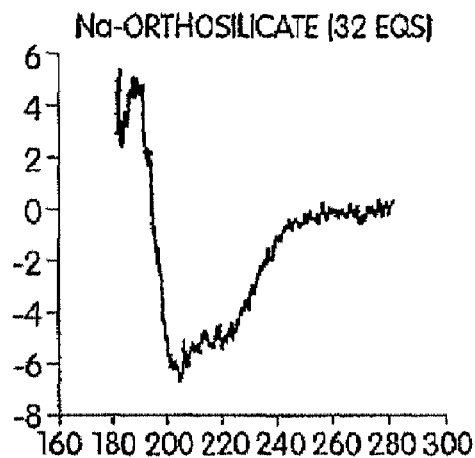
Figure 5A:
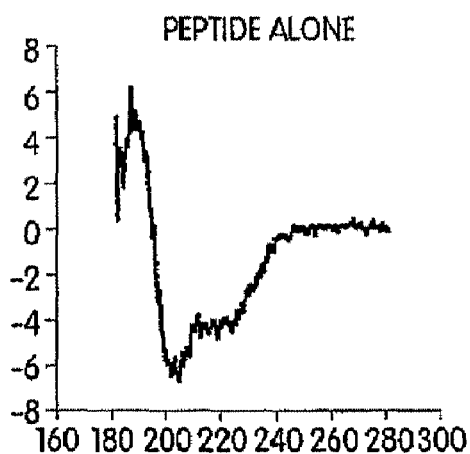
FIGS. 5A-5F illustrate the effect of 3-aminopropylsilantriol on the peptide of FIG. 1, as indicated by CD data.
Figure 5B:
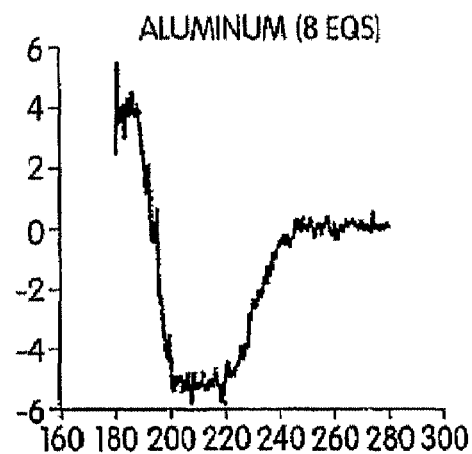
Figure 5C:
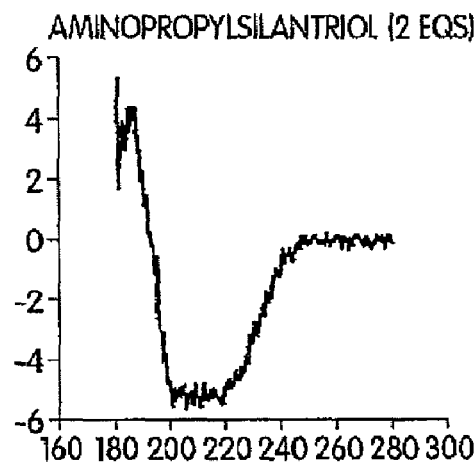
Figure 5D:
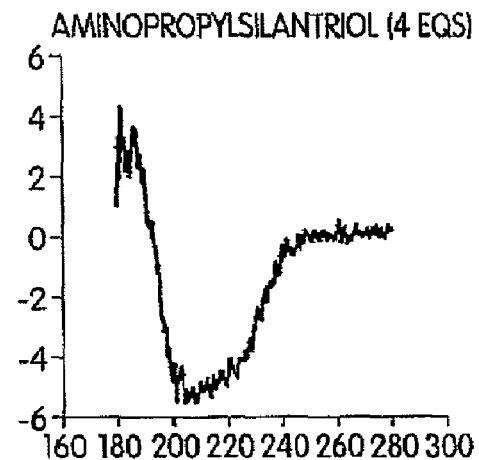
Figure 5E:
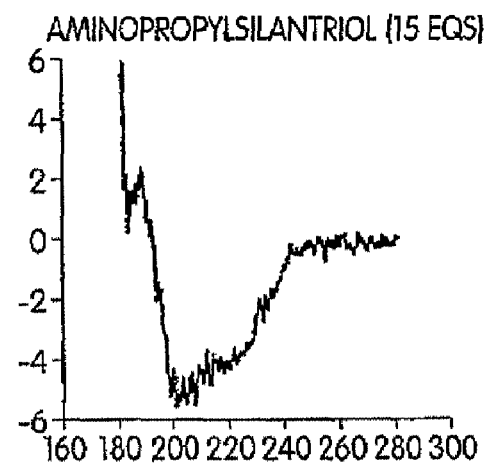
Figure 5F:
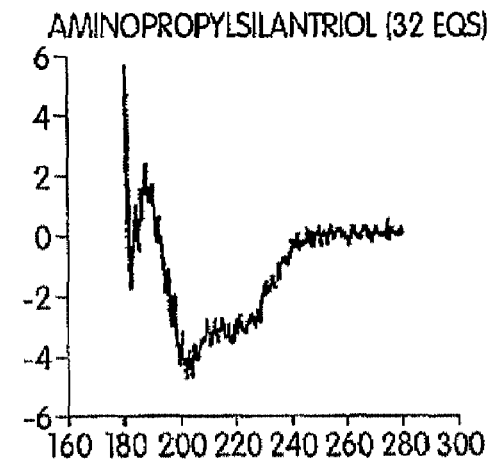
Figure 6A:
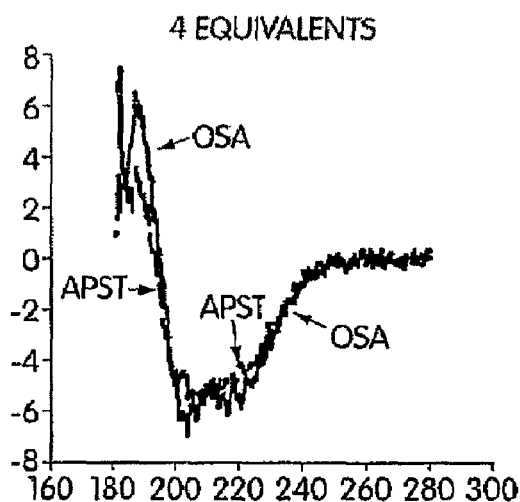
FIGS. 6A-6D illustrate comparative CD data for sodium orthosilicate versus 3-aminopropylsilantriol.
Figure 6B:
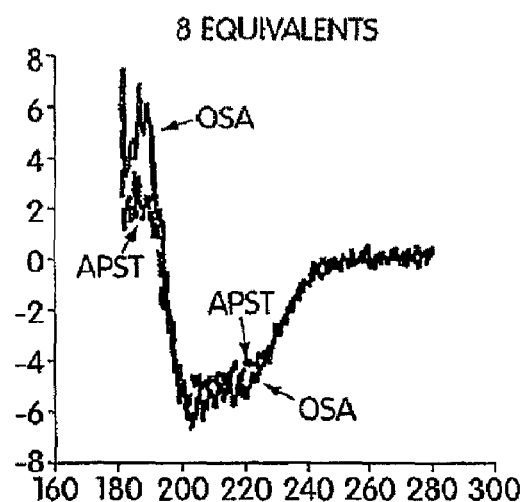
Figure 6C:
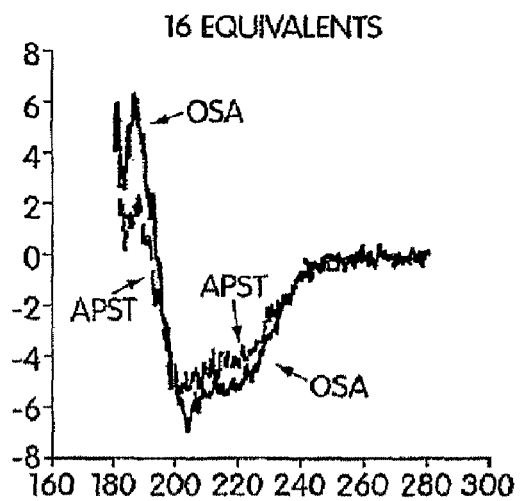
Figure 6D:
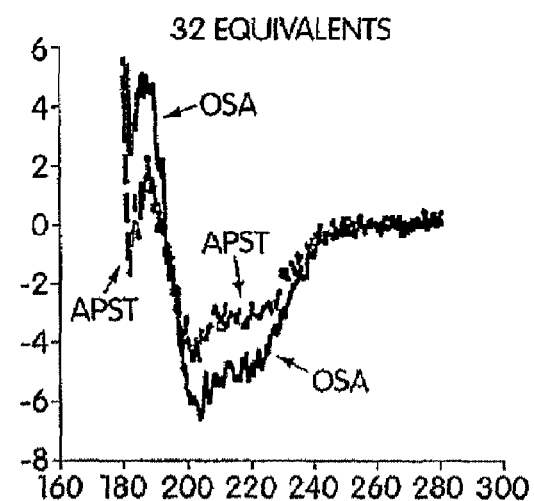
Figure 7A:
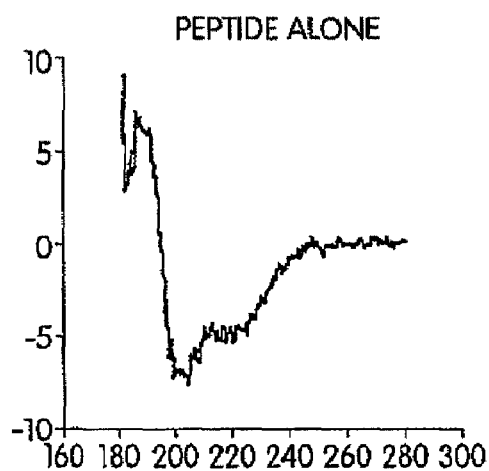
FIGS. 7A-7D illustrate the effect of 3-cyanopropyltrichlorosilane on the peptide of FIG. 1, as indicated by CD data.
Figure 7B:
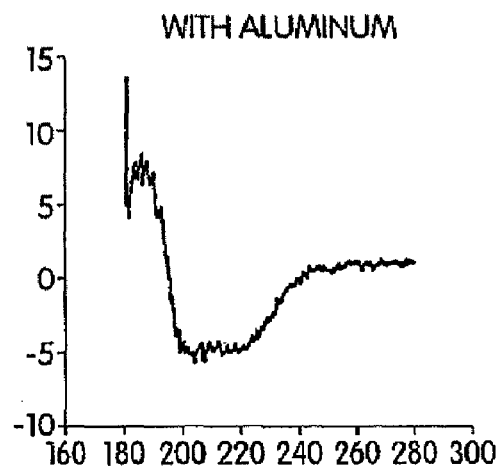
Figure 7C:
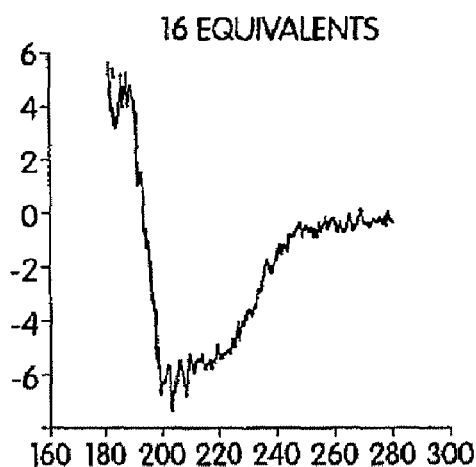
Figure 7D:
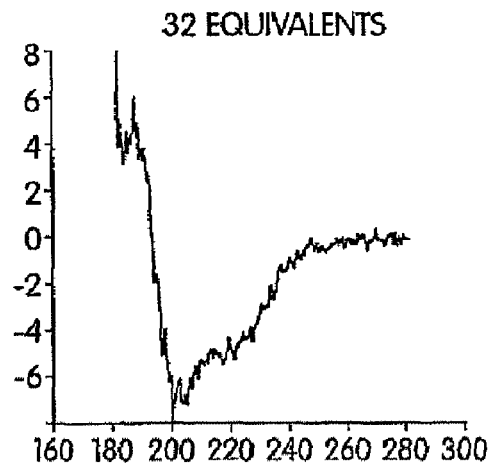
Figure 8A:
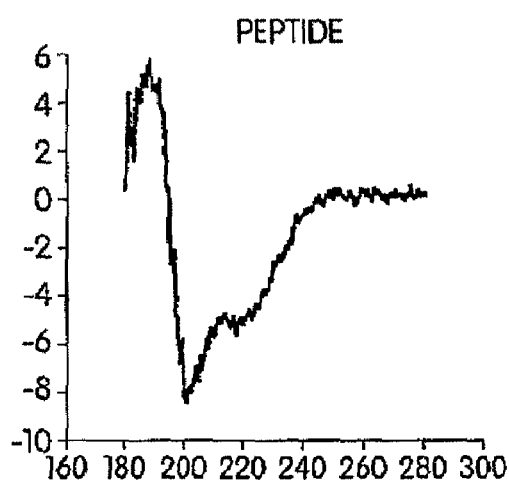
FIGS. 8A-8D illustrate the effect of hexylmethyldichlorosilane on the peptide of FIG. 1, as indicated by CD data.
Figure 8B:
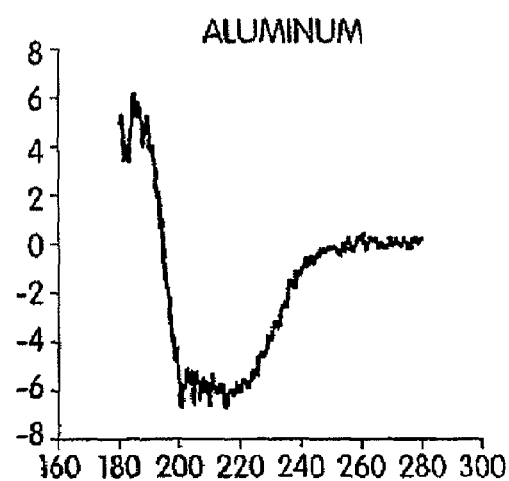
Figure 8C:
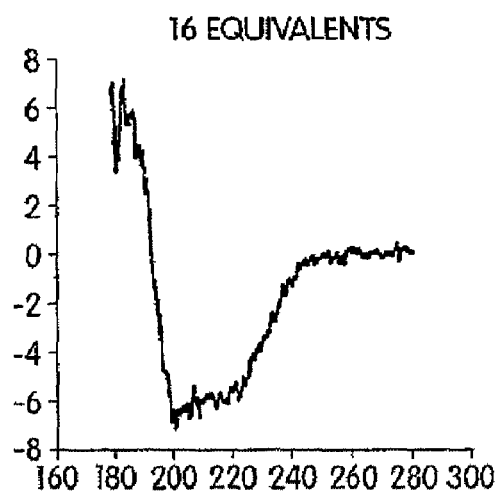
Figure 8D:
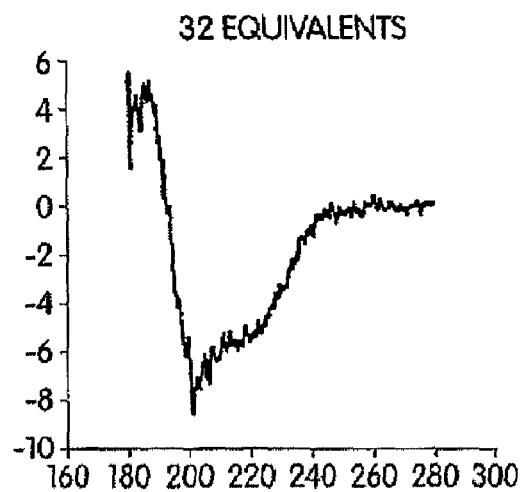
Figure 9A:
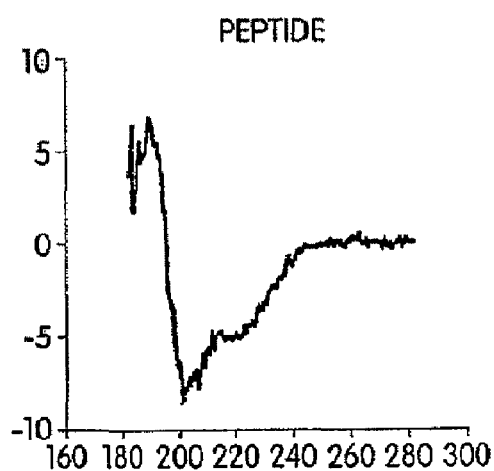
FIGS. 9A-9D illustrate the effect of methylphenyldichlorosilane on the peptide of FIG. 1, as indicated by CD data.
Figure 9B:
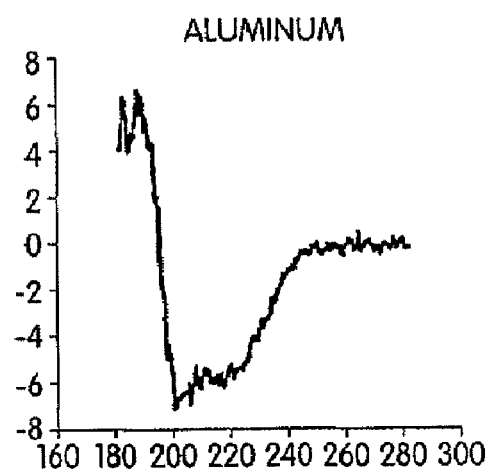
Figure 9C:
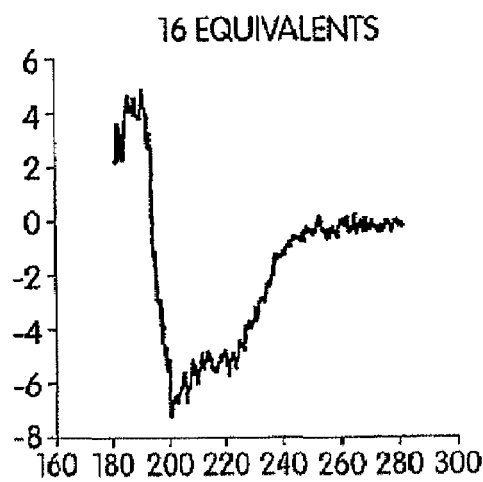
Figure 9D:
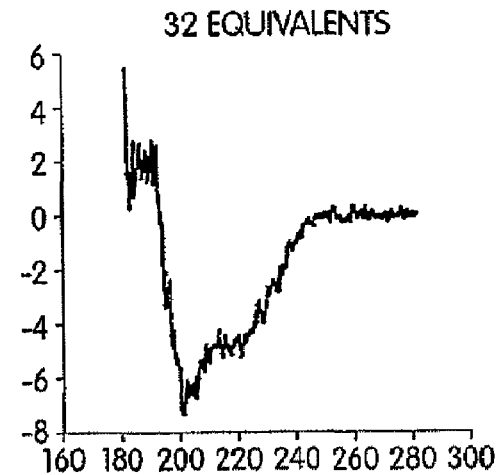
Figure 10A:
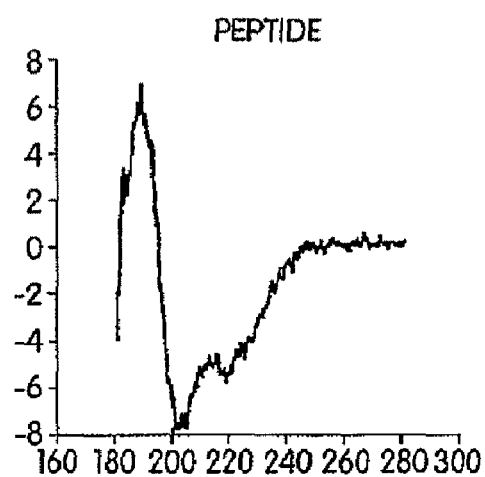
FIGS. 10A-10D illustrate the effect of dichlorodiethylsilane on the peptide of FIG. 1, as indicated by CD data.
Figure 10B:
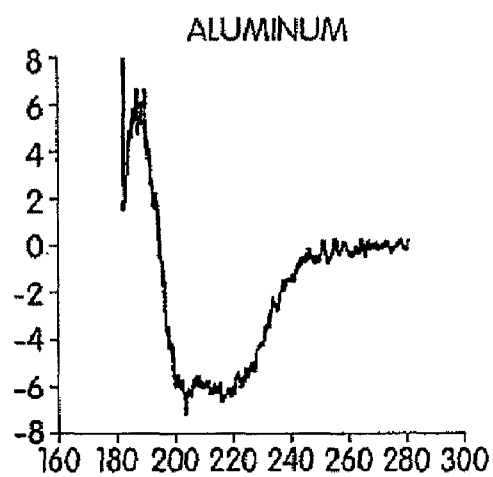
Figure 10C:
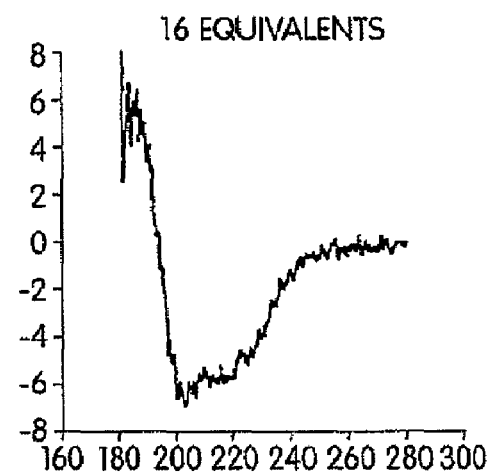
Figure 10D:
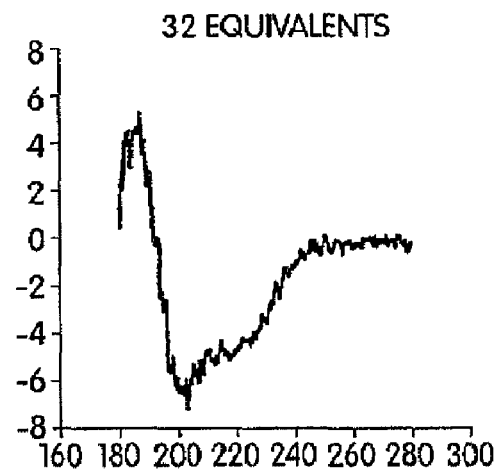
Figure 11A:
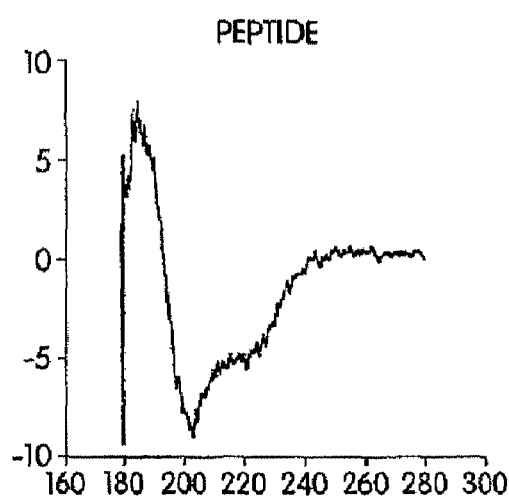
FIGS. 11A-11E illustrate the effect of dichlorodiisopropylsilane on the peptide of FIG. 1, as indicated by CD data.
Figure 11B:
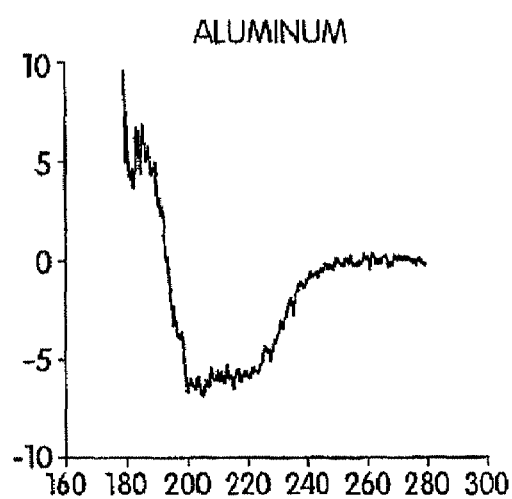
Figure 11C:
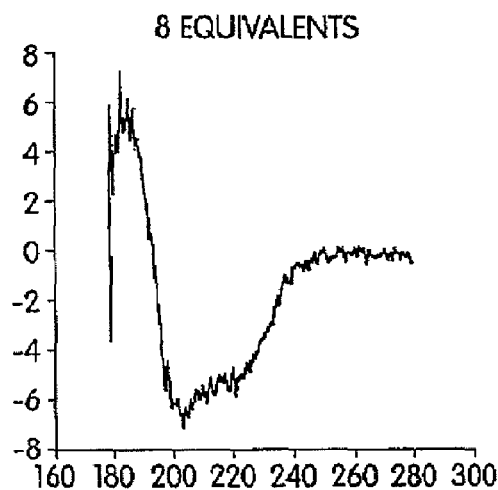
Figure 11D:
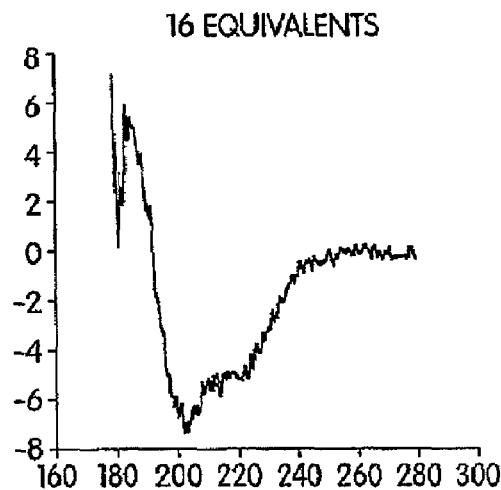
Figure 11E:
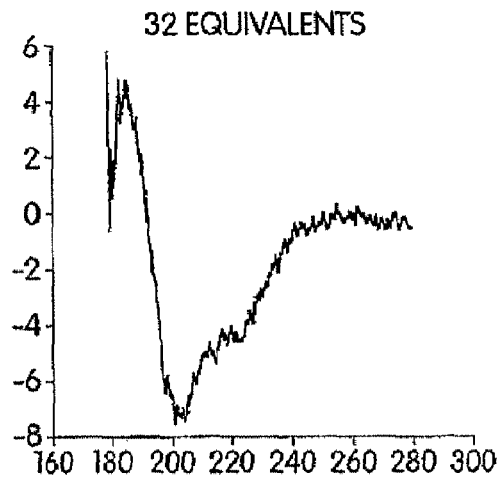
Figure 12A:
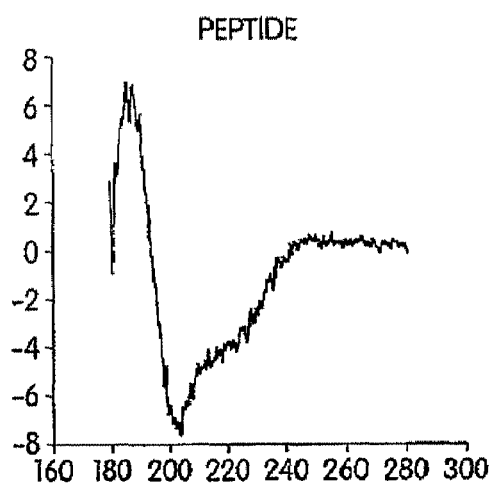
FIGS. 12A-12E illustrate the effect of (dichloro)methylsilylbutyronitrile on the peptide of FIG. 1, as indicated by CD data.
Figure 12B:
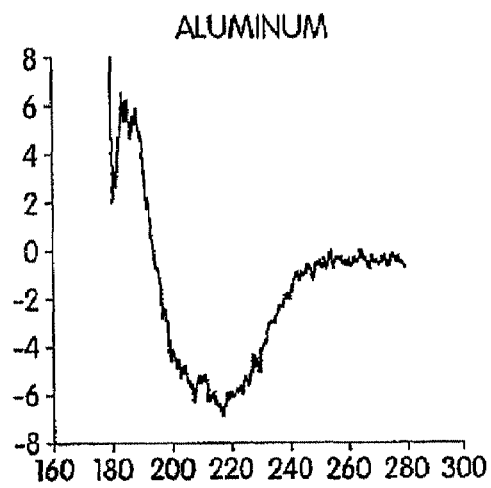
Figure 12C:
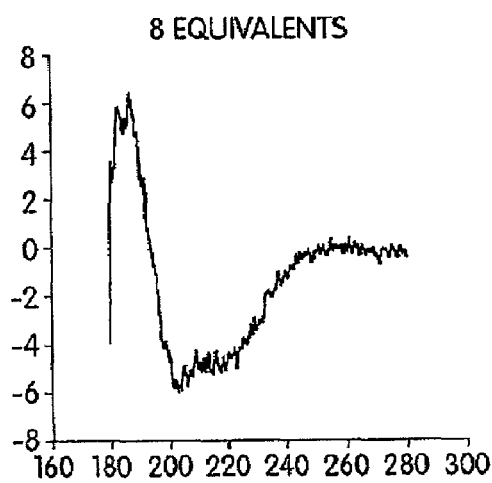
Figure 12D:
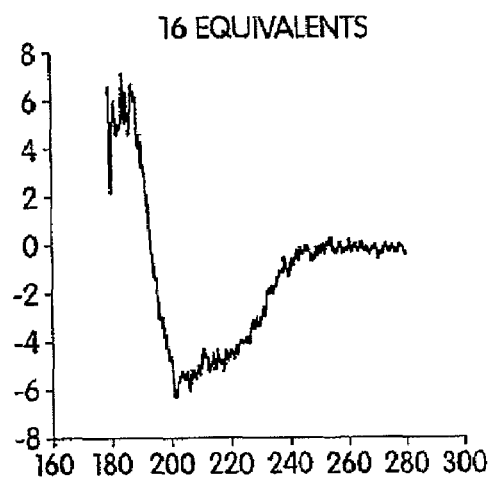
Figure 12E:
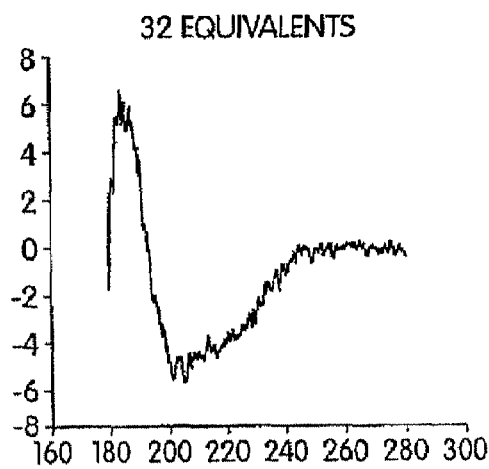

The results of these experiments are summarized in Table 1. FIGS. 3 and 4 show control experiments using sodium metasilicate nonahydrate and sodium orthosilicate, respectively, as a source of the silicate ion. With sodium metasilicate, the CD curve showed some return to its original shape at about 32 equivalents (FIG. 3D). Sodium orthosilicate, however, showed a return to the original shape beginning at 4 equivalents (FIG. 4C). At around 16 equivalents the CD spectrum with sodium orthosilicate is similar in shape to the original NF-M17 spectra (FIG. 4D).

TABLE 1

Figure 2U:
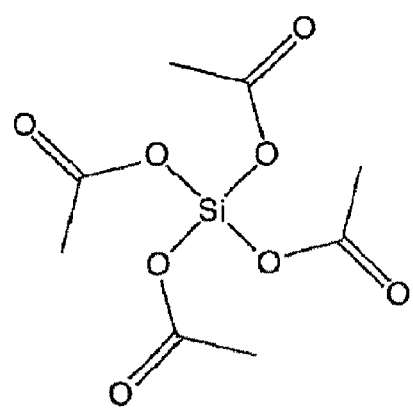

| Organosilanol | Restore original spectra? |
|---|---|
| Triol | |
| APST | Yes |
| TSPMP | (precipitation of peptide) |
| OTCS | (gelation of OTCS) |
| CPTCS | Yes |
| Diol | |
| DPSD | (DMSO interfered with spectra) |
| HMDS | Yes |
| MPDS | Yes |
| DCDES | Yes |
| DCDIPS | Yes |
| DCMSBN | Yes |
| Monol | |
| PTMS | No |
| TBDMS | No |
| TES | No |
| BDS | No |

The APST solution used was a 22-25% by weight solution in water. The APST solution was able to restore the CD spectrum of NF-M17/aluminum to its original shape, with better recovery at higher equivalents (FIG. 5). The APST solution also showed improved chelation of aluminum compared to sodium orthosilicate (FIG. 6).

The TSPMP solution used was a 42% by weight solution in water. This triol did not successfully restore the original spectra of NF-M17. The incremental addition of TSPMP solution precipitated the peptide out of solution (data not shown). The OTCS solution used was a 100% solution. With the addition of water, the organochlorosilane solution underwent gelation and did not restore the original spectra of the NF-M17 peptide (data not shown).

The CPTCS solution used was as a 100% solution. The CPTCS solution did not gel on addition of water, and the solution restored the CD spectrum of NF-M17/aluminum to its original shape at around 32 equivalents (FIG. 7).

DPSD did not restore the original spectra of NF-M17. The incremental addition of DPSD solution precipitated the peptide out of solution (data not shown). In contrast, solutions of HMDS (FIG. 8), MPDS (FIG. 9), DCDES (FIG. 10), DCDIPS (FIG. 11), and DCMSBN (FIG. 12) each restored the original CD spectrum of NF-M17/aluminum to its original shape at around 32 equivalents.

Solutions of PTMS, TBDMS, TES, and BDS (data not shown) each did not restore the original spectra of the NF-M17 peptide.

In conclusion, the organosilanes, the diols and triols, restored the original CD spectra of NF-M17, thus indicating the restoration of the original conformation of NF-M17. The diols and triols may form polyvalent crosslinked entities that may favorably bind and strip aluminum from NF-M.

EXAMPLE 2

This prophetic example illustrates a method for treating Alzheimer's disease in a human subject with a composition of the invention comprising an organosilicon compound that inhibits interaction between aluminum and A-beta$_{1-42}$ peptide.

The subject is given the composition orally, in the form of a pill, once a day. The dose concentration per day is 4.0 mcmol/kg. Administration is carried out for a period of about six months. This treatment interferes with further development of neurofibrillary tangles and senile plaques.

EXAMPLE 3

A-beta$_{1-42}$ peptide in TFE is believed to have a large degree of alpha-helical structure that is changed to a beta-sheet structure by the presence of aluminum ions. That transformation can be seen in a CD spectrum as a flattening of the signal. Reagents that partially or fully restore the initial A-beta$_{1-42}$ signal can thus be interpreted as the binding of aluminum to the reagent, allowing the peptide to regain its native alpha-helix character.

Beta-amyloid peptide (human amyloid beta-peptide 1-42, $A\beta_{1-42}$ or A-beta$_{1-42}$, SynPep) (FIG. 1) was dissolved in a solution of 80% trifluoroethanol ("TFE")/20% water at 10 mg/ml to make a stock solution, stored at 4° C. The stock solution was diluted to 0.45 nm/ml to 0.50 nm/ml in TFE for use in these experiments. The molecular weight of the peptide was 4315 Da; thus, 0.45 mg/ml is equivalent to 100 micromolar. Aluminum perchlorate was dissolved in TFE at a concentration of 10 mg/ml. The silicate test reagents were typically dissolved and hydrolyzed in water at 60 mM.

The CD spectrum was determined for each sample as follows. The sample was placed in a JASCO J-810 spectropolarimeter, in a cuvette having a volume of 100 ml, and a path length of 500 mm. The sensitivity of the instrument was approximately 100 millidegrees. Each spectrum was scanned with a wavelength range of between about 180 nm to about 260 nm, or between about 180 nm to about 280 nm. The data pitch was about 0.2 nm. The scan settings were performed under continuous scanning, at about 50 nm/min, with a response of 1 second. The data presented are data from two accumulations.

Initially, TFE alone was scanned as a control to confirm the standard spectrum. Next, A-beta$_{1-42}$ peptide alone was scanned at the start of each reagent test. Then, 2 to 4 microliter aliquots of 10 mM aluminum perchlorate were added by a 2-20 microliter micropipettor and new scans were recorded. Mixing within the cuvette done with a 100 microliter pipettor. Other experiments (not shown) have revealed a large flattening of the peptide spectrum with the addition of 8 to 12 microliters of aluminum (equaling about 8 to 12 molar equivalents). Aliquots of a test compound were added to the peptide and aluminum in the cuvette, 2 to 4 microliters at a time, mixing well and assaying the spectrum between each addition. This procedure was repeated for each compound. The cuvette was well rinsed 3 to 5 times with about 100 microliters of TFE between assays.

The compounds tested in this example were: 3-cyanopropyltrichlorosilane (CPTCS) (FIG. 2D), dichlorodiethylsilane (DCDES) (FIG. 2H), dichlorodiisopropylsilane (DCDIPS) (FIG. 2I), (dichloro)ethylmethylsilane (DCEMS) (FIG. 2O), hexylmethyldichlorosilane (HMDS) (FIG. 2F), (dichloro)m- ethylsilylbutyronitrile (DCMSBN) (FIG. 2J), dichlorosilacyclobutane (DCSCB) (FIG. 2P), 1,7-dioxa-6-sila-spiro[5.5]undecane (SDSU) (FIG. 2Q), sodium orthosilicate, triethoxysilylbutyronitrile (TESB) (FIG. 2R), triethoxysilylpropionitrile (TESP) (FIG. 2S), trihydroxysilylpropylmethyl phosphonate (TSPM) (FIG. 2B), triethylsilanol (TES) (FIG. 2M), tetrakis(dimethylamino)silane ("tetrakis") (FIG. 2T), and tetraacetooxysilane (TAS) (FIG. 2U). These compounds were obtained from Gelest (Morrisville, Pa.), Sigma-Aldrich (St. Louis, Mo.), Lancaster Synthesis (Windham, N.H.), Fluka (St. Louis, Mo.), and Alpha Aesar (Ward Hill, Mass.).

Figure 13:
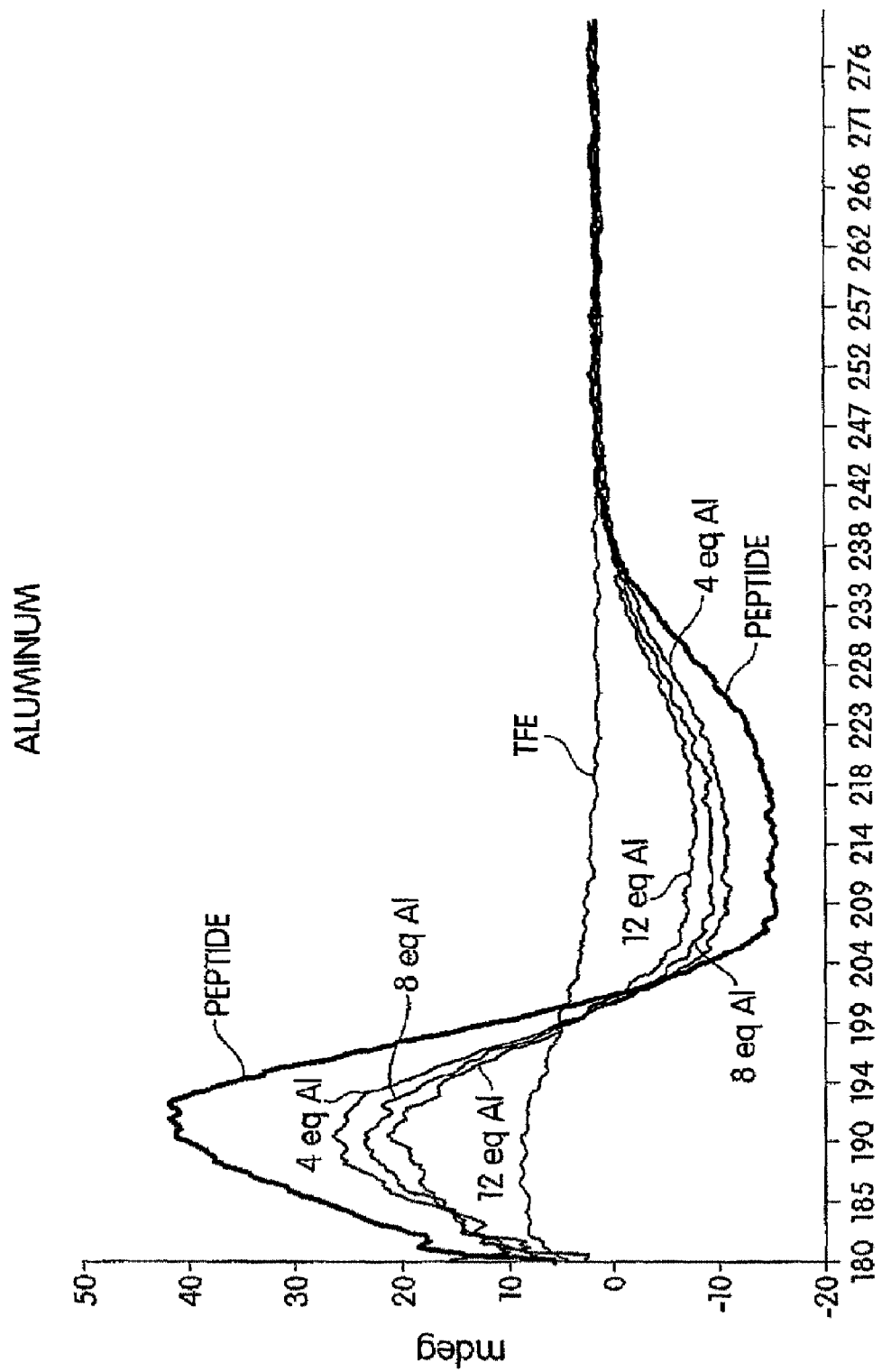
FIG. 13 illustrates the effect of aluminum on human A-beta$_{1-42}$, as illustrated by CD data.

FIG. 13 illustrates the effect of aluminum on the A-beta$_{1-42}$ peptide. In FIG. 13, the CD spectrum of the A-beta$_{1-42}$ peptide decreases with higher concentrations of aluminum.

Figure 14:
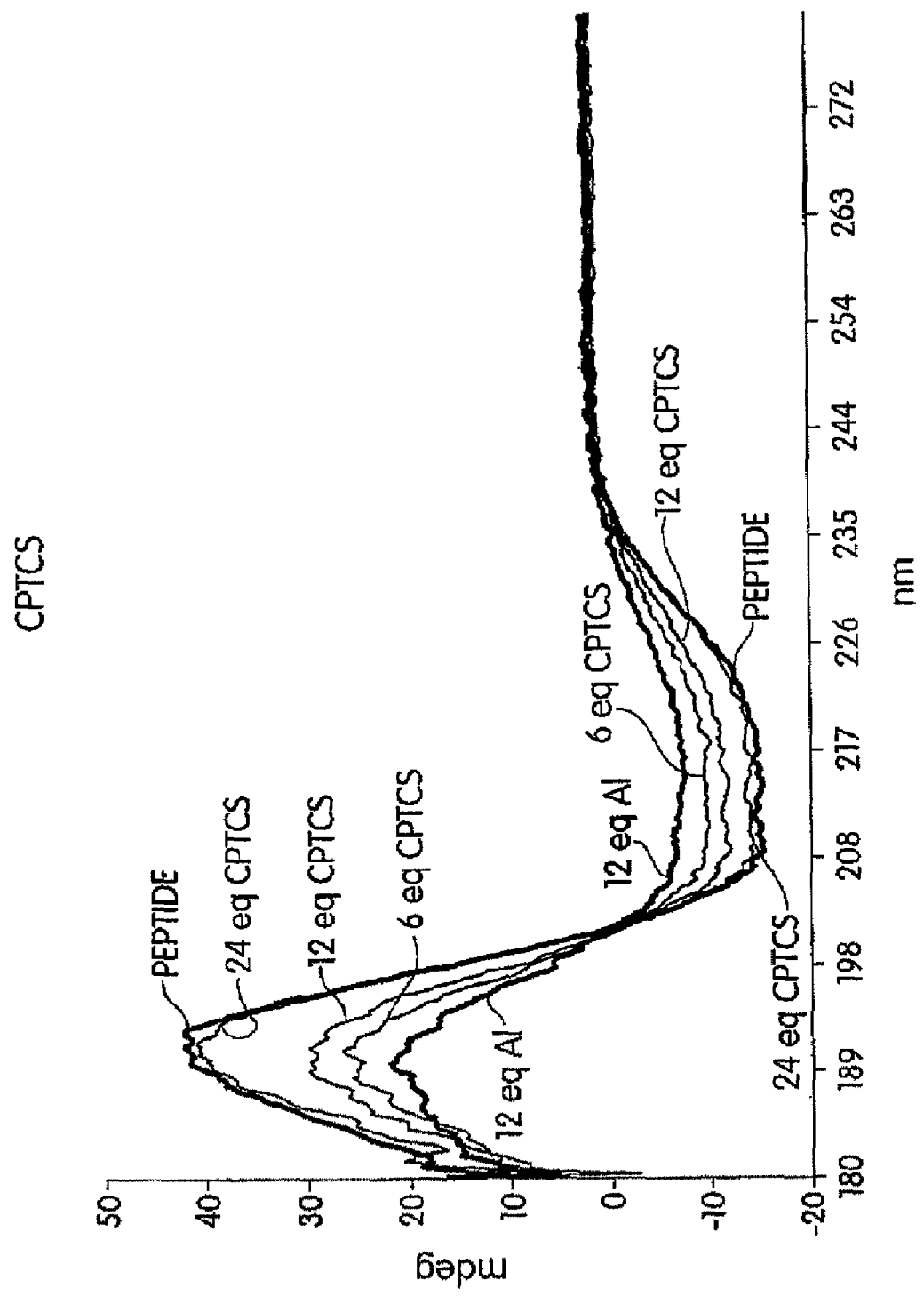
FIG. 14 illustrates the effect of 3-cyanopropyltrichlorosilane on A-beta$_{1-42}$, as illustrated by CD data.

FIG. 14 illustrates the effect of CPTCS on the aluminum-amyloid peptide system. In FIG. 14, the addition of 12 equivalents of aluminum to the solution containing the A-beta$_{1-42}$ peptide causes a major reduction in the CD spectrum. However, the further addition of CPTCS is able to restore the CD spectrum of the peptide. Moderate reversal was seen at 6 equivalents and 12 equivalents, while almost full reversal of the effects of aluminum on the peptide was seen with the addition of 24 equivalents of CTPCS.

Figure 15:
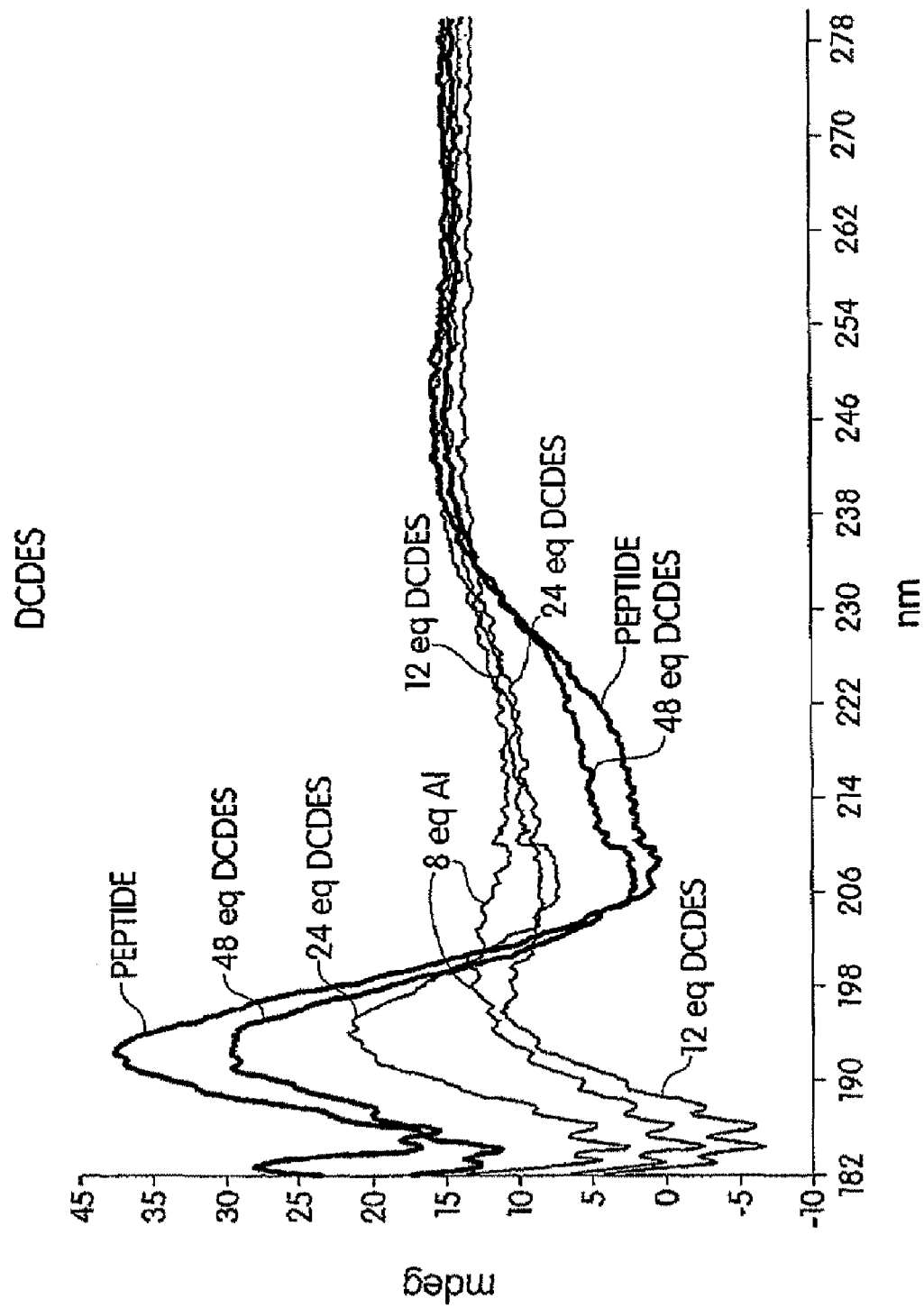
FIG. 15 illustrates the effect of dichlorodiethylsilane on A-beta$_{1-42}$, as illustrated by CD data.
Figure 16:
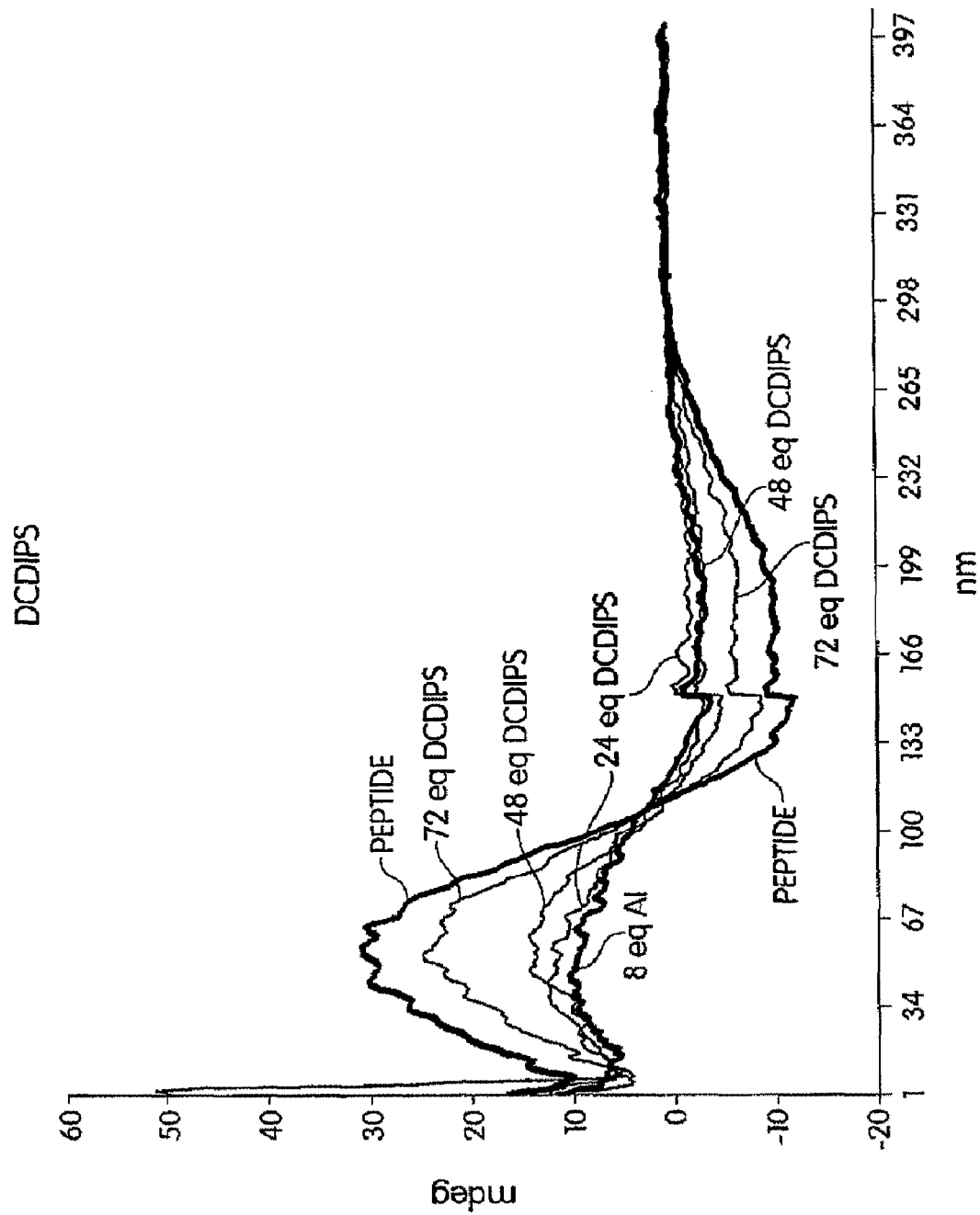
FIG. 16 illustrates the effect of dichlorodiisopropylsilane on A-beta$_{1-42}$, as illustrated by CD data.
Figure 17:
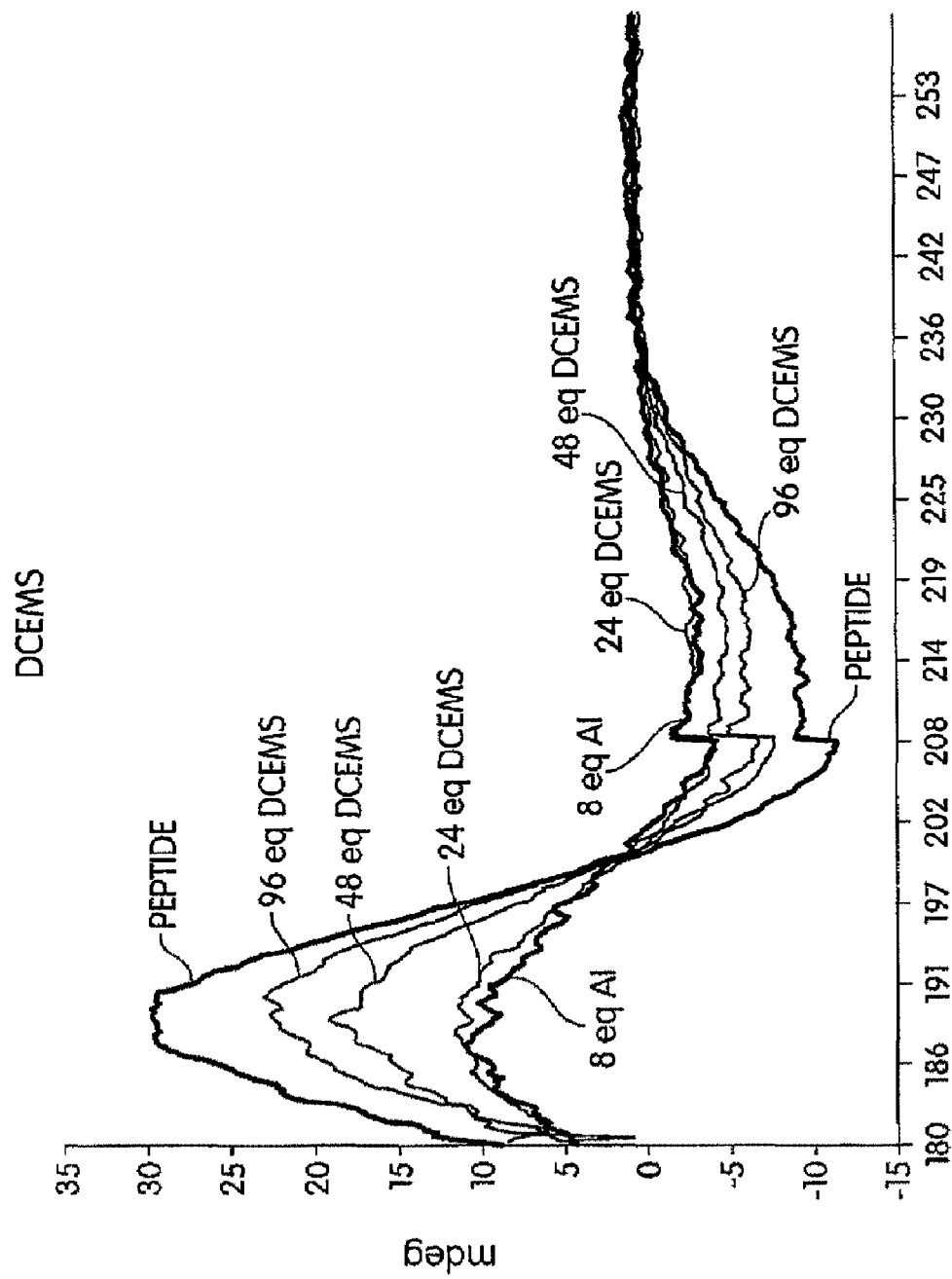
FIG. 17 illustrates the effect of (dichloro)ethylmethylsilane on A-beta$_{1-42}$, as illustrated by CD data.
Figure 18:
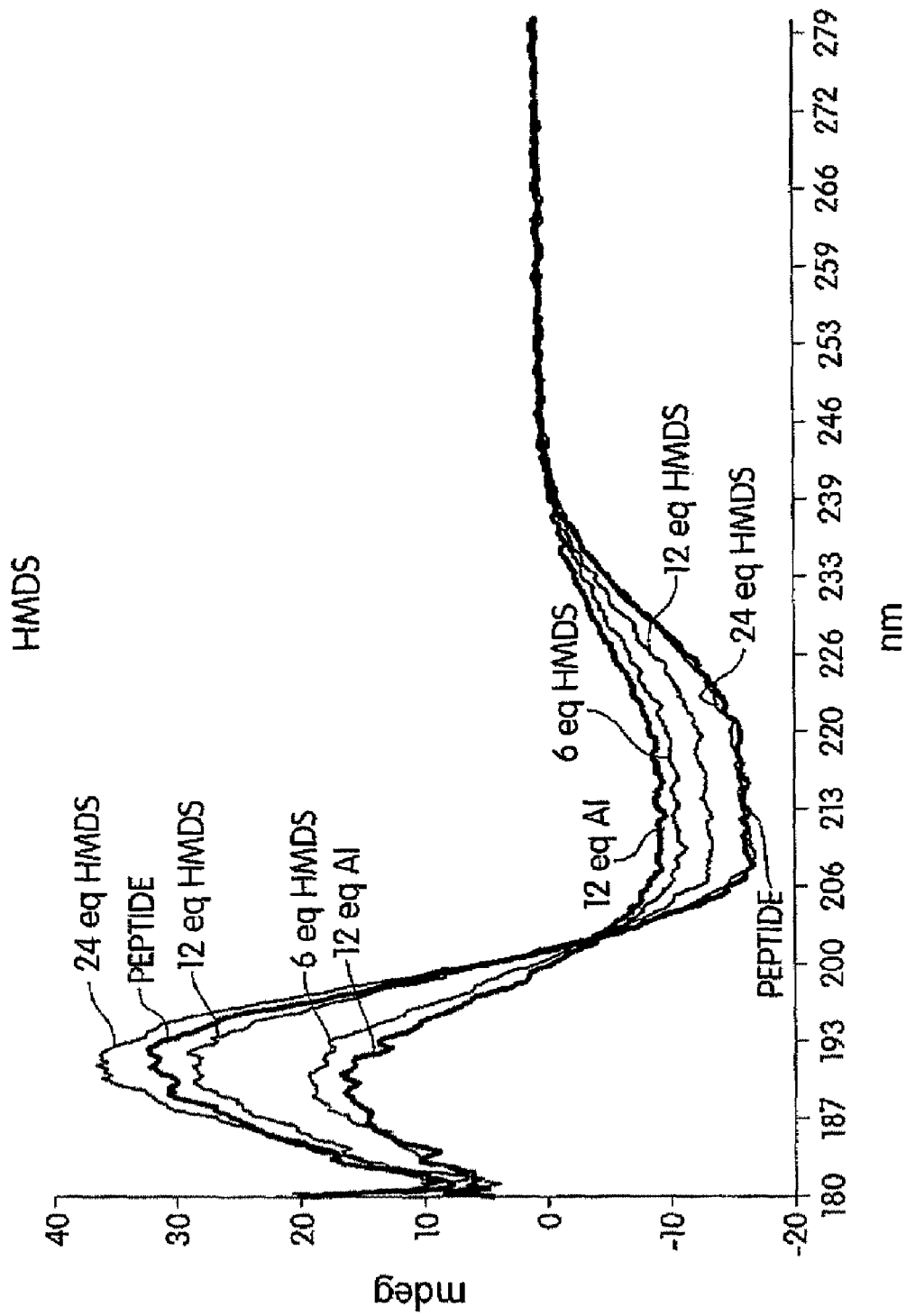
FIG. 18 illustrates the effect of hexylmethyldichlorosilane on A-beta$_{1-42}$, as illustrated by CD data.
Figure 19:
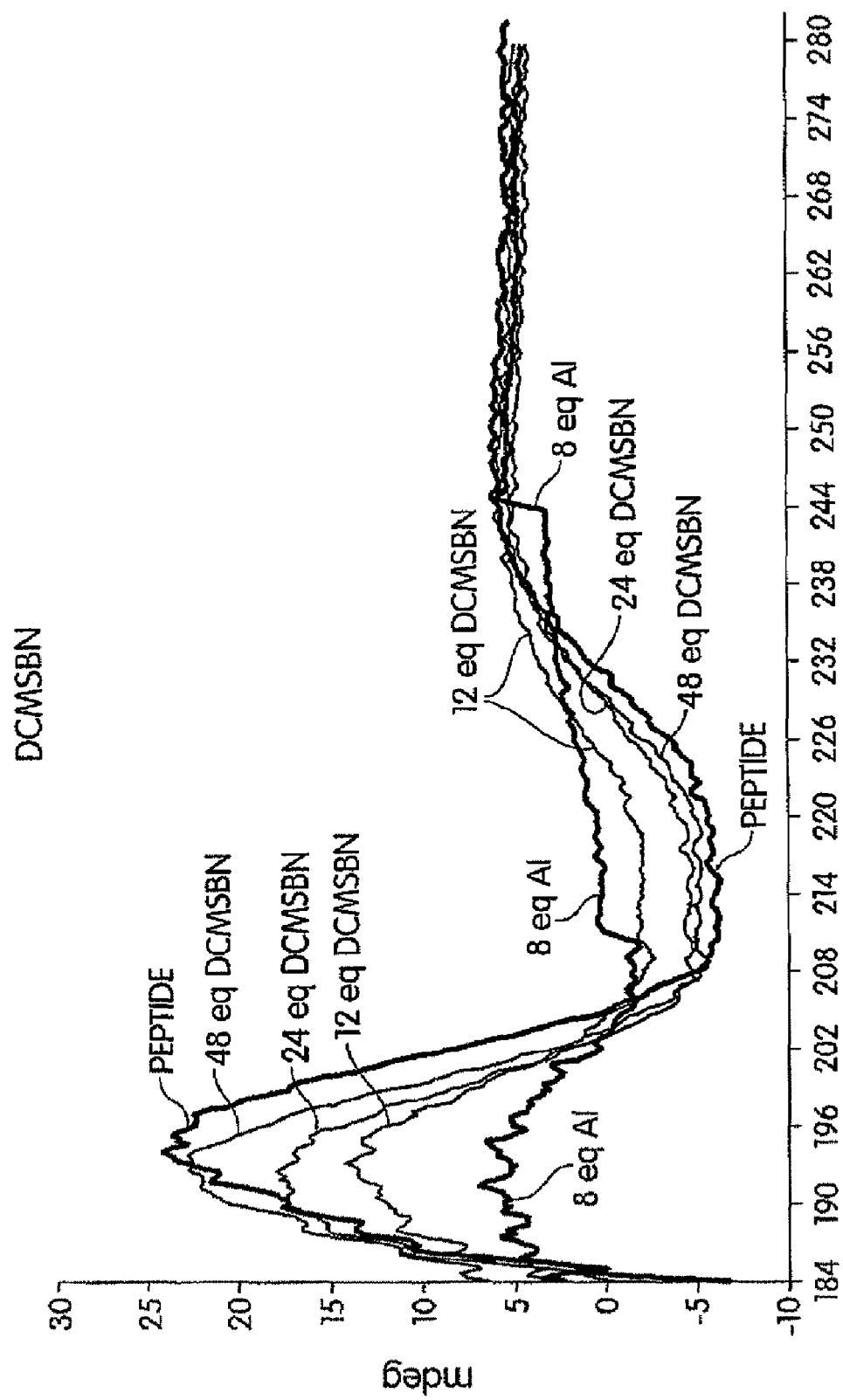
FIG. 19 illustrates the effect of (dichloro)methylsilylbutyronitrile on A-beta$_{1-42}$, as illustrated by CD data.
Figure 20:
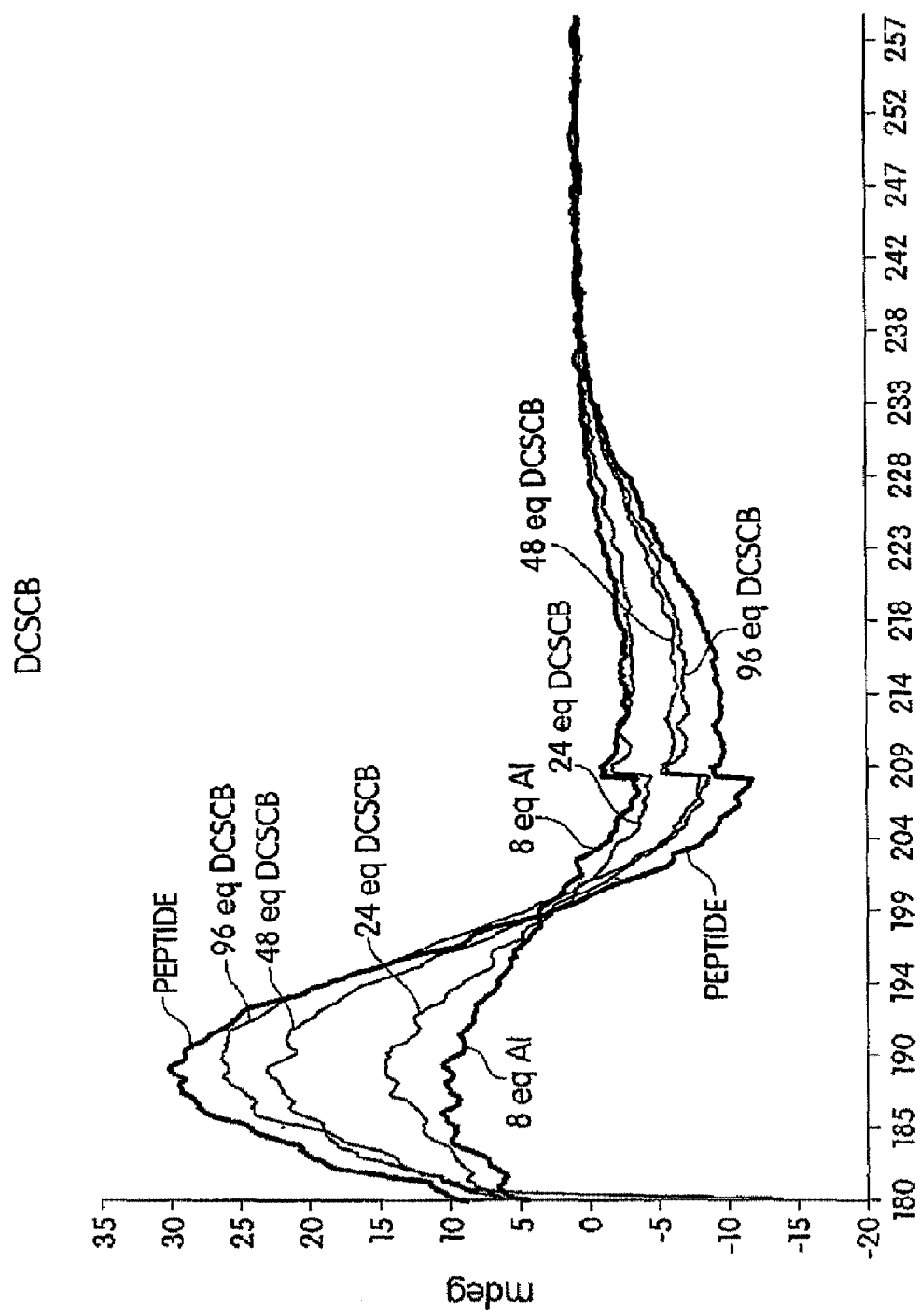
FIG. 20 illustrates the effect of dichlorosilacyclobutane on A-beta$_{1-42}$, as illustrated by CD data.
Figure 21:
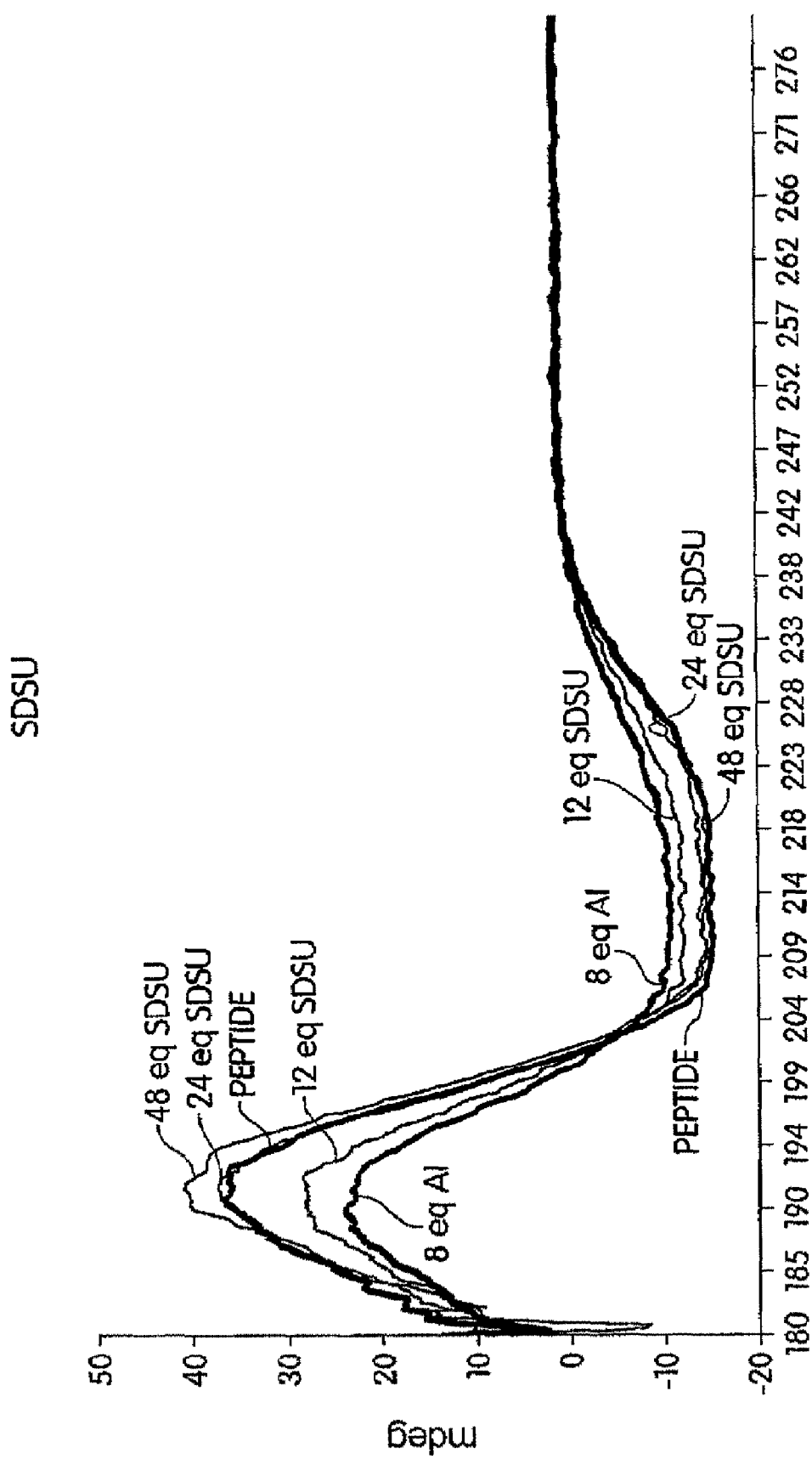
FIG. 21 illustrates the effect of 1,7-dioxa-6-sila-spiro[5.5]undecane on A-beta$_{1-42}$, as illustrated by CD data.
Figure 23:
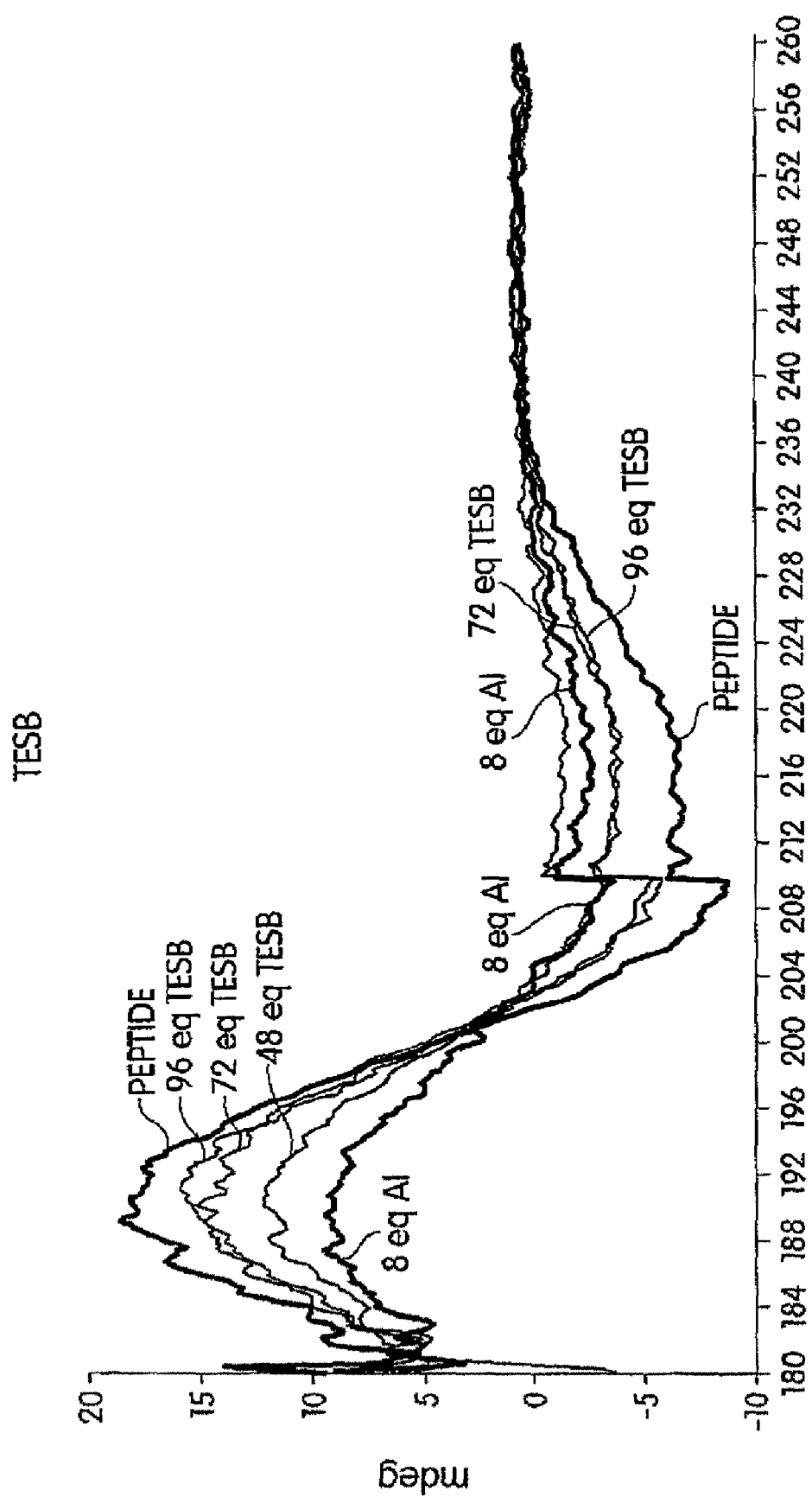
FIG. 23 illustrates the effect of triethoxysilylbutyronitrile on A-beta$_{1-42}$, as illustrated by CD data.
Figure 24:
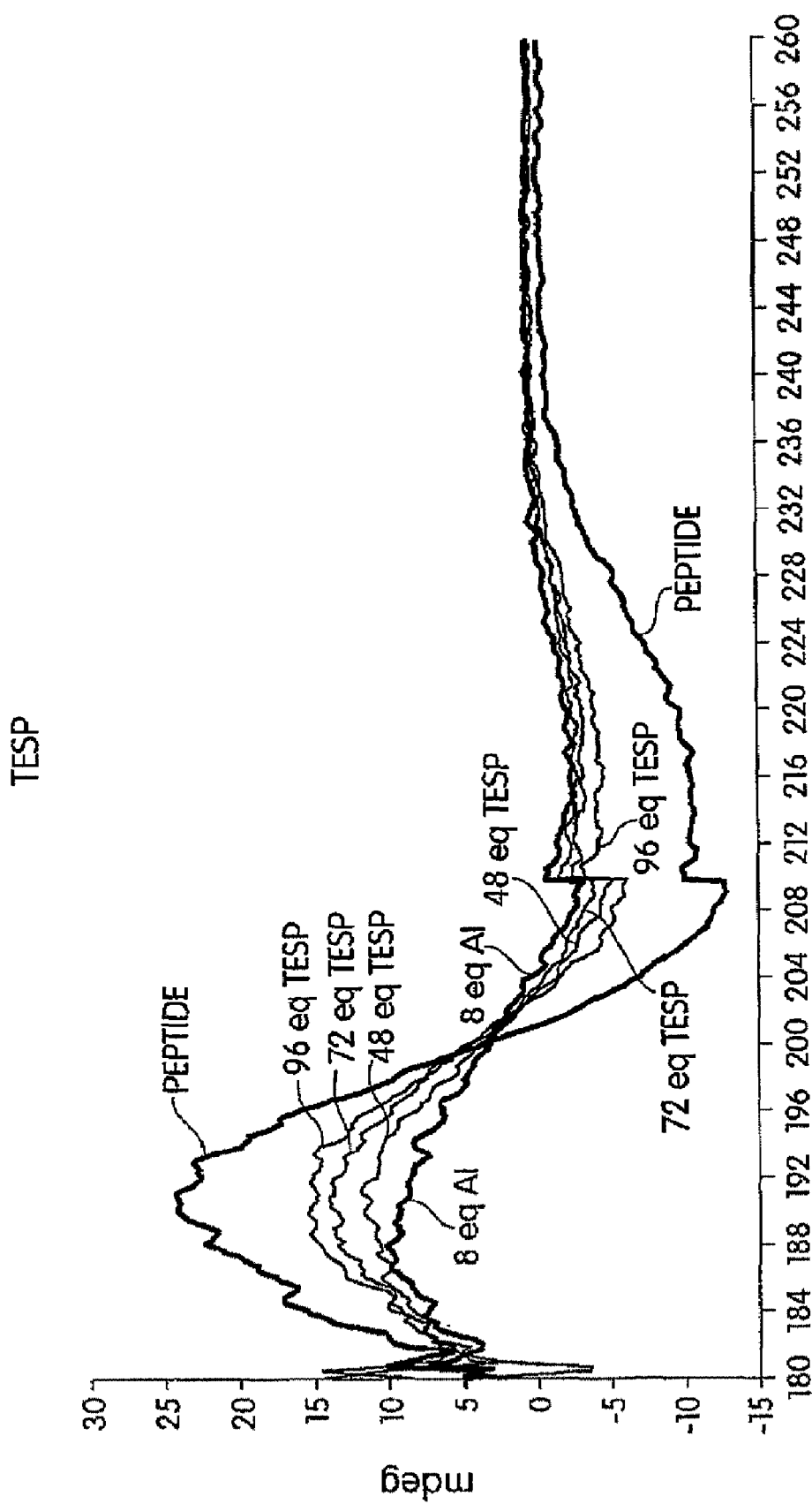
FIG. 24 illustrates the effect of triethoxysilylpropionitrile on A-beta$_{1-42}$, as illustrated by CD data.
Figure 25:
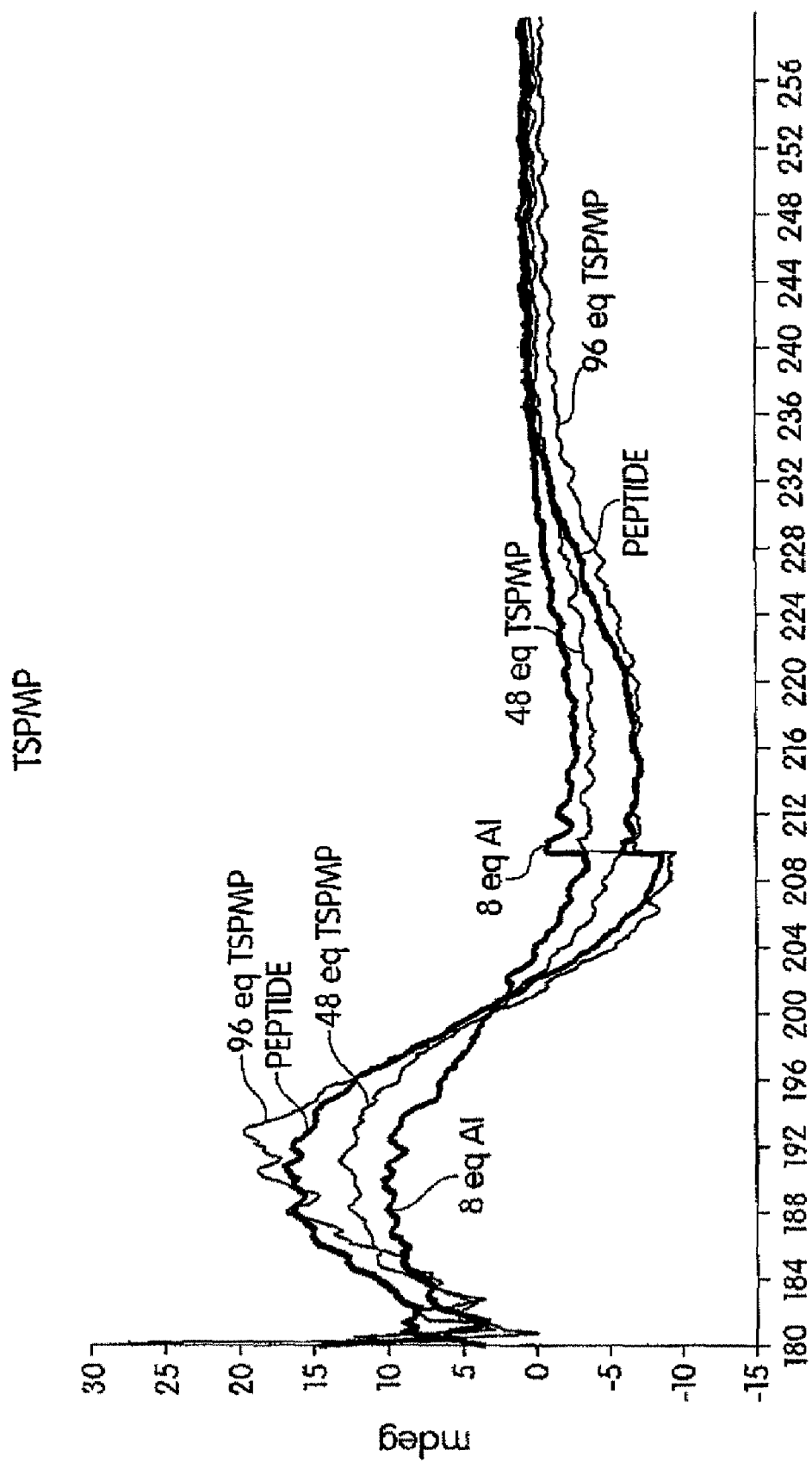
FIG. 25 illustrates the effect of trihydroxysilylpropylmethyl phosphonate on A-beta$_{1-42}$, as illustrated by CD data.
Figure 26:
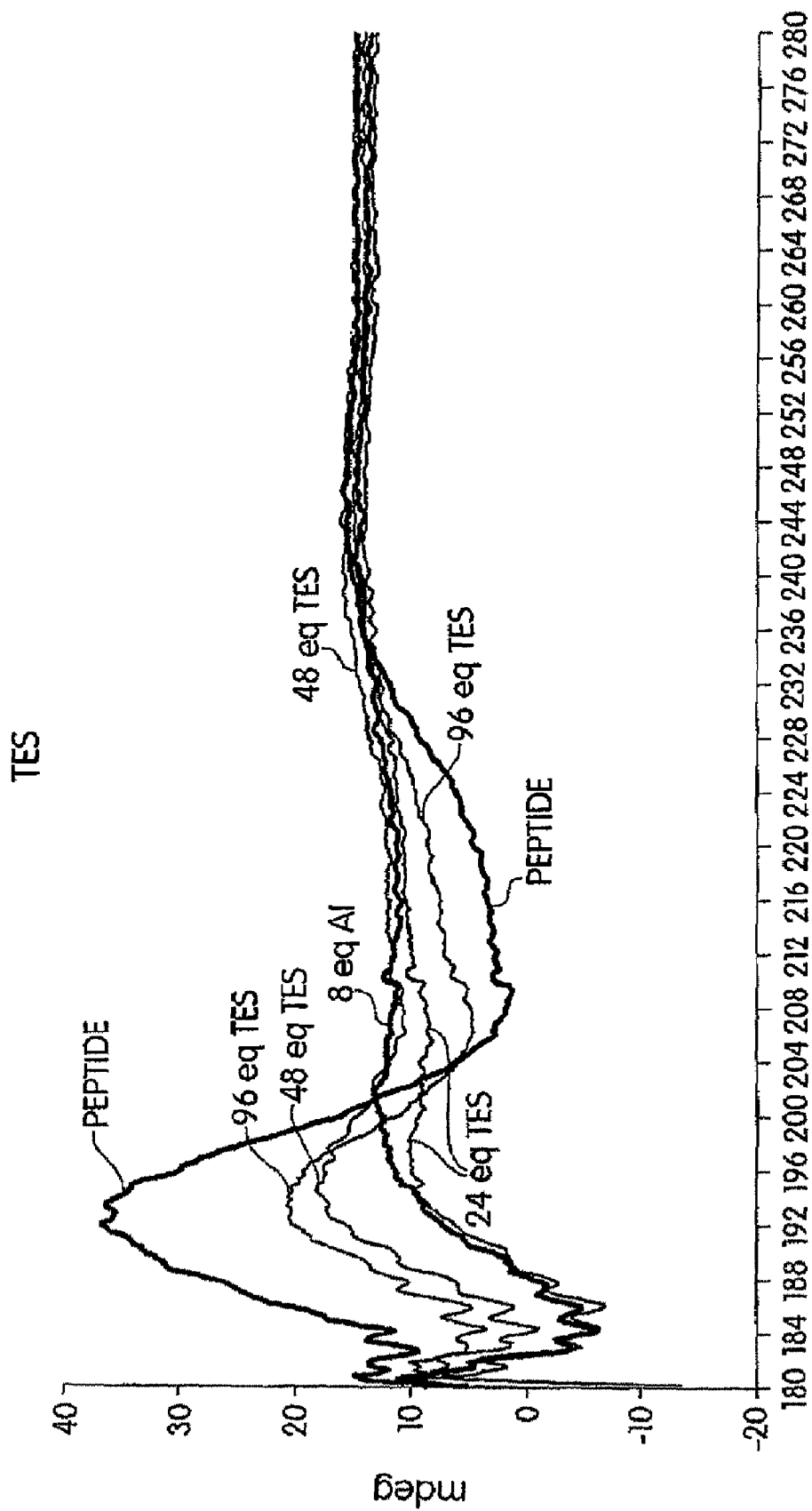
FIG. 26 illustrates the effect of triethylsilanol on A-beta$_{1-42}$, as illustrated by CD data.
Figure 27:
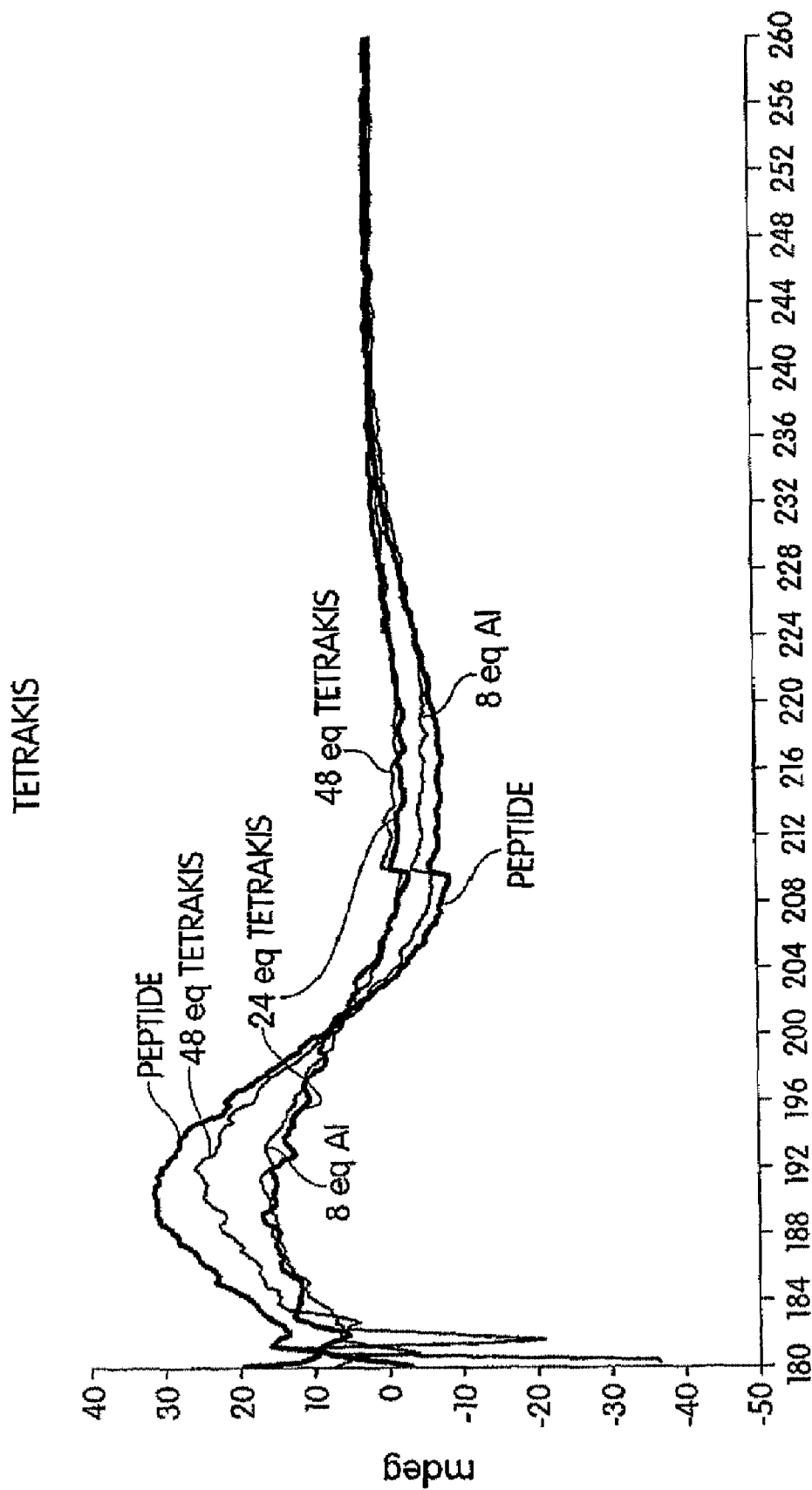
FIG. 27 illustrates the effect of tetrakis(dimethylamino) silane on A-beta$_{1-42}$, as illustrated by CD data.
Figure 28:
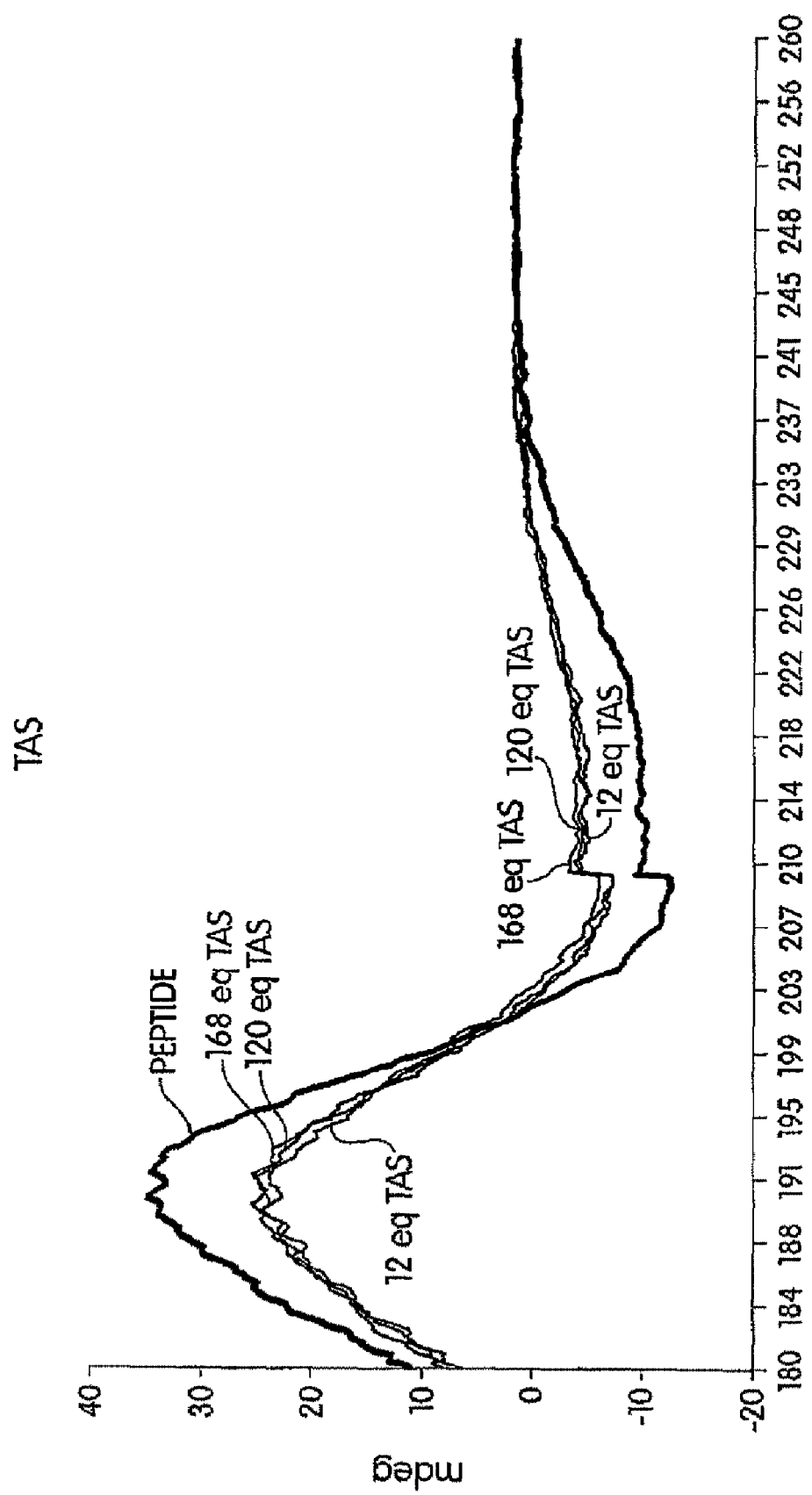
FIG. 28 illustrates the effect of tetraacetooxysilane on A-beta$_{1-42}$, as illustrated by CD data.

Similar results were seen with DCDES. In FIG. 15, the addition of 8 equivalents of aluminum caused a major reduction in the CD spectrum of the A-beta$_{1-42}$ peptide, while the addition of DCDES to the system at least partially restored the CD spectrum with greater amounts of restoration with higher equivalencies of DCDES. Similarly, DCDIPS (FIG. 16), DCEMS (FIG. 17), HMDS (FIG. 18), DCMSBN (FIG. 19), DCSCB (FIG. 20), SDSU (FIG. 21), sodium orthosilicate (FIG. 22), TESB (FIG. 23), TESP (FIG. 24), TSPMP (FIG. 25), TES (FIG. 26), tetrakis (FIG. 27), and TAS (FIG. 28) each at least partially restored the original CD spectrum of the peptide, after the peptide had been exposed to aluminum.

EXAMPLE 4

In this example, the transport of various organosilicon compounds of the invention across cell monolayers that mimic the blood-brain barrier was demonstrated. Two different cell lines were used as model blood-brain barrier systems: Caco-2 cells and bMVEC cells. Detection of the organosilicon compounds was performed using inductively coupled plasma spectrometry (ICP), per EPA method 200.7, using an ultrasonic nebulizer.

Caco-2 is a cell line derived from human intestinal epithelium, commonly used for studies of molecular transport across epithelia with tight junctions. The Caco-2 cells used in these experiments were from the laboratory of Dr. Neil Simister at Brandeis University, originating from the ATCC (American Type Culture Collection). The cells were grown in Dulbecco's Modified Eagle's Medium (DMEM), with 5% fetal bovine serum, 50 microgram/ml gentamicin at 5% $CO_2$, 37° C. Cells grown in Isgrove's medium and RPMI-1640 instead of DMEM showed similar times to reach confluence and similar morphology (data not shown). The Caco-2 cells formed electrically tight junctions, as assayed by measuring the electrical resistance with a World Precision Instruments EVOM-G.

The cells were grown in tissue culture flasks, and split (passaged) when confluence reached about 4:1. Cells were seeded for experiments onto Corning Costar Transwell inserts, polyester or polycarbonate, with 0.4 micrometer pores. Cells on transparent polyester membranes could be directly observed using phase contrast microscopy. The cells were fed fresh medium at intervals of every 2 to 4 days. The cells were used for assays when the electrical resistance of the cell monolayer was at least 400 ohms/cm$^2$.

Bovine microvascular epithelial cells are primary cells from bovine brain, purchased frozen from Cambrex Bio Science. These cells were grown on collagen-coated membrane inserts, overcoated with fibronectin. The medium used was Endothelial Basal Medium 2 (Clonetics) supplemented with bECGF, ascorbic acid, platelet poor horse serum, penicillin, streptomycin and fungizone (provided as a kit by Cambrex). One aliquot of cells was diluted and split to seed 48 6.5 mm membranes (coming Costar polyester, 0.4 micrometer pores). The cells were fed fresh medium every 2-3 days, and used when visually confluent.

Figure 29A:
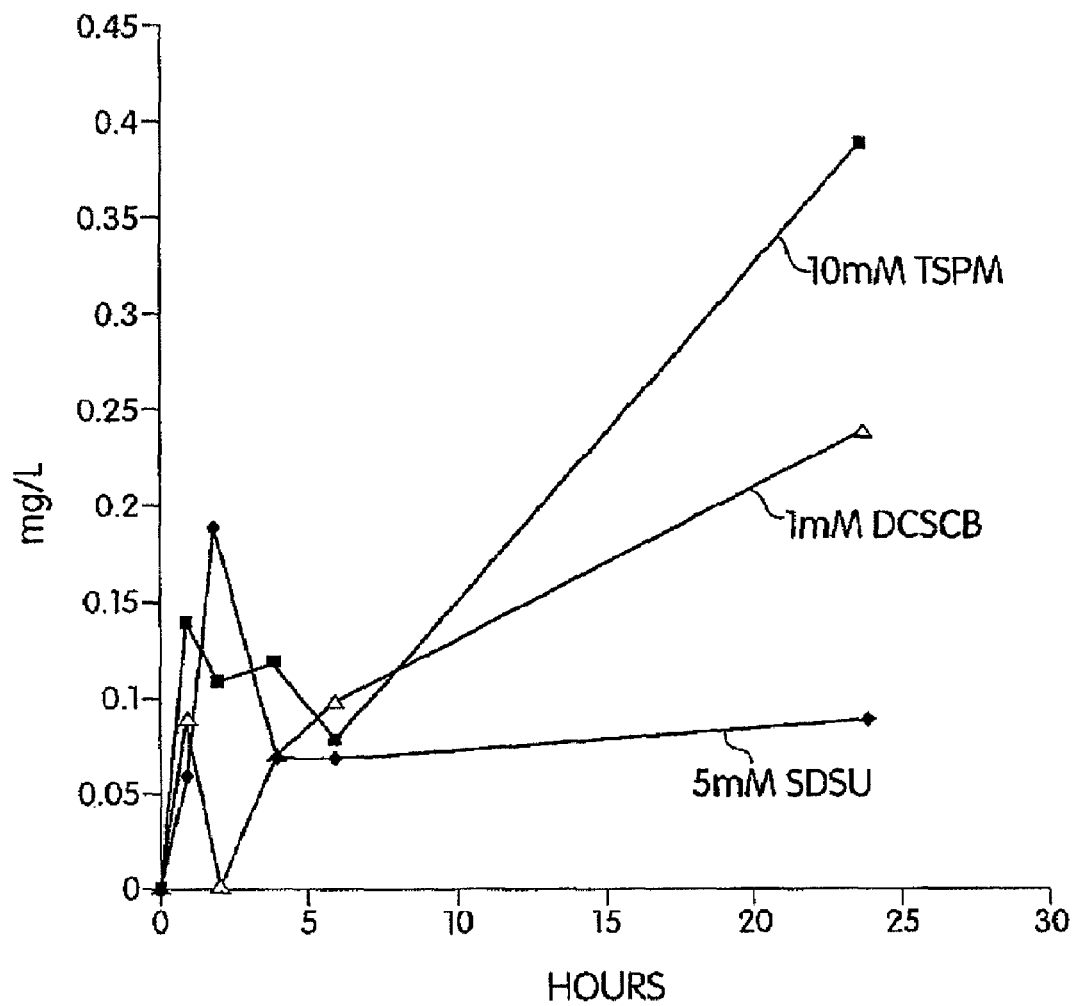
FIGS. 29A-29B illustrate transport of certain organosilicon compounds of the invention across Caco-2 cells.
Figure 29B:
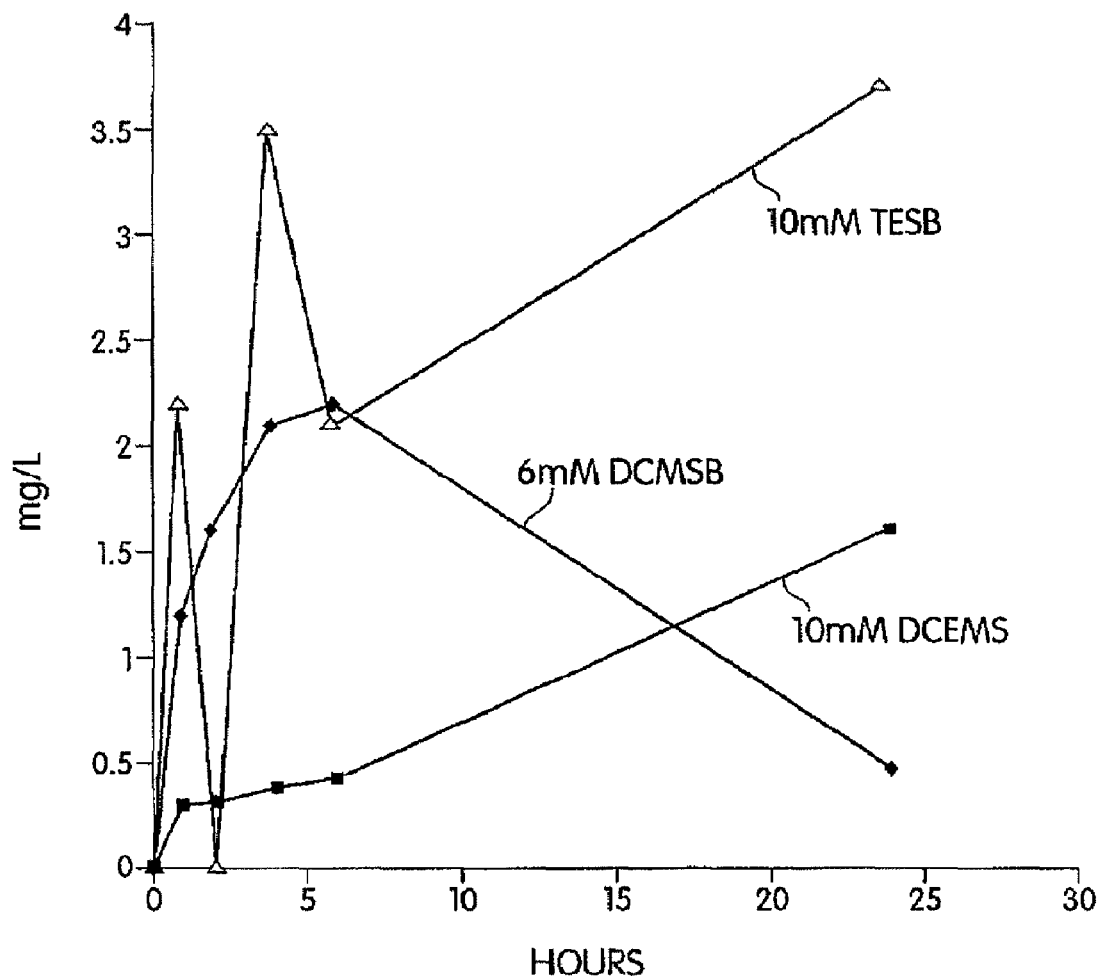

Six compounds were tested for transport across the two cell lines in this example: SDSU, DCSCB, TSPM, TESB, DCMSBN, and DCEMS. Data from these experiments can be seen in FIGS. 29A and 29B (Caco-2 cells) and FIG. 30 (bMVEC). In FIGS. 29A and 29B, the transport of these organosilicon compounds are plotted as a function of time and hours. The starting concentrations on the apical side for each compound range between 1 mM and 10 mM. In all cases, a significant amount of transport was observed, across the Caco-2 cells, with more transport being observed for TESB, DCMSBN, and DCEMS (FIG. 29B) than TSPM, DCSCB, and SDSU (FIG. 29A).

Figure 30:
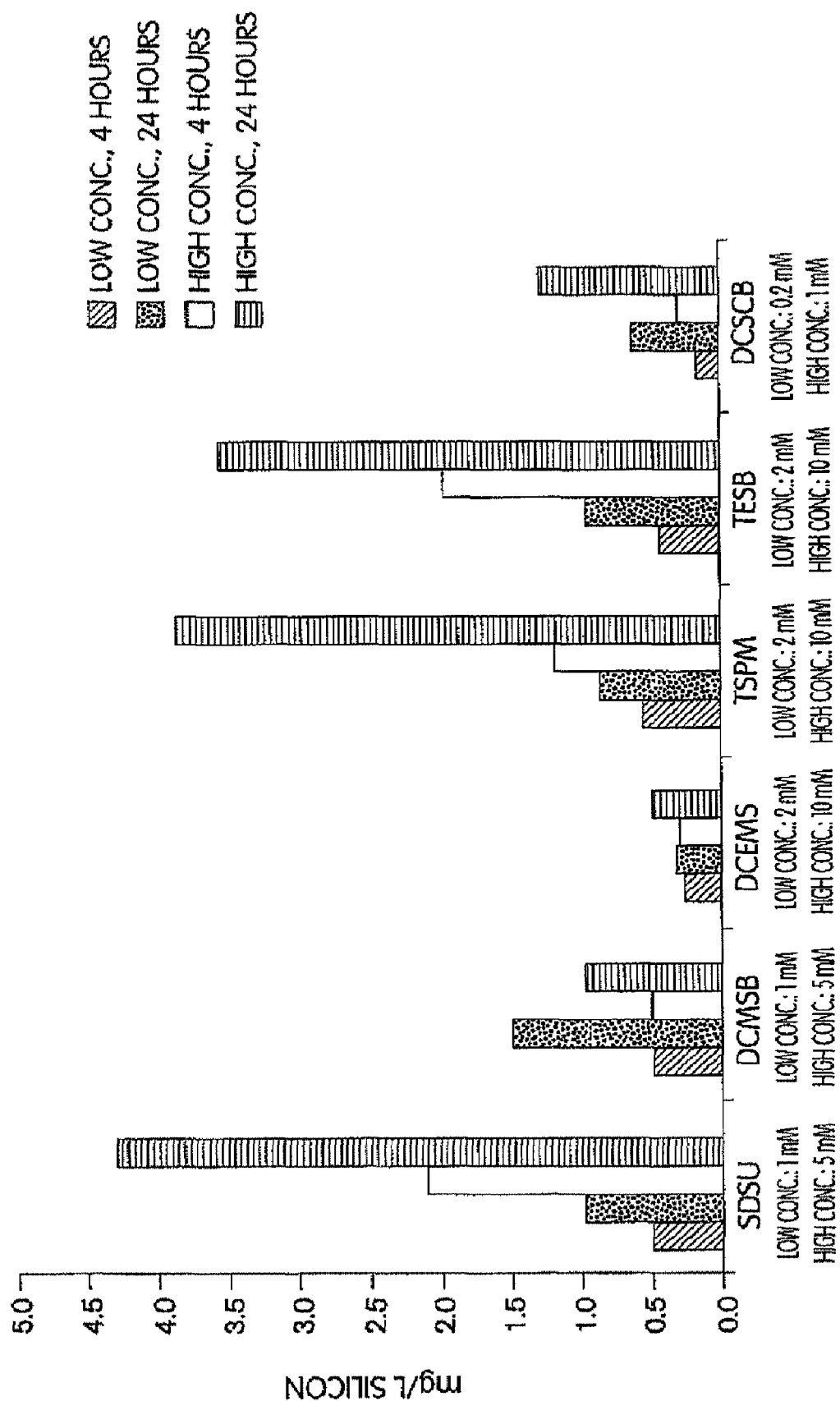
FIG. 30 illustrates molecular transport of certain organosilicon compounds of the invention across bMVEC cells.

FIG. 30 illustrates transport of these compounds across the bMVEC cells. In FIG. 30, data are plotted for transport after 4 h and after 24 h, for two different donor concentrations. In all cases, a significant amount of transport was observed, with more transport occurring for higher concentration apicals.

Thus, this example illustrates that various compounds of the invention can successfully be transported across a cell culture model of the blood-brain barrier.

EXAMPLE 5

This example illustrates a method of making 1,7-dioxa-6-sila-spiro[5.5]undecane (FIG. 2Q) in one embodiment of the invention.

A 2 liter 4-neck flask equipped with a dry-ice condenser, overhead stirring, a pot thermometer, and a funnel was charged with 54.29 g of SiC$_4$. 4-chloro-1-butanol was added through the funnel at a pot temperature below 40° C. over a period of about 30 min. The mixture was stirred at room temperature for about 4 hours. 250 ml of ether was then added, followed by 4.86 g of magnesium turnings. After stirring at room temperature for 14 h, 125 ml of tetrahydrofuran ("THF") was added in 5 portions over a time period of 1 h. After all of the magnesium turnings were consumed, another 4.86 g of magnesium was added, followed by another 125 ml of tetrahydrofuran, added dropwise. The mixture was stirred at room temperature for 6 hours, then allowed to settle overnight. The superliquid was transferred into another flask, and the salts were washed with 125 ml of ether. The solutions were combined, then distilled using a short column. 5.32 g (12.4% yield) of the desired product was obtained upon heating at a head temperature of 55° C. at 8 mmHg.

Schematically, this reaction can be represented as follows:

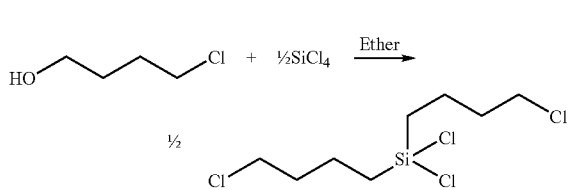

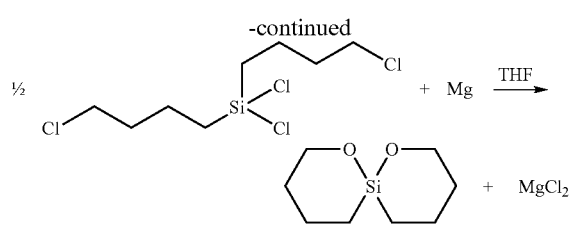

Physical data for this reaction is as follows:

TABLE 2

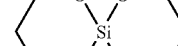

| Component | 4-chloro-1-butanol | SiCl₄ | Mg | Ether | THF | [silicon bicyclic] | MgCl₂ |
|---|---|---|---|---|---|---|---|
| Molecular weight | 108.57 | 169.90 | 24.31 | 74.12 | 72.11 | 172.03 | 95.22 |
| Boiling point (° C.) | 50-52 | 57.6 | | 35-36 | 65-67 | 55-58 | |
| Specific gravity | 1.09 | 1.483 | | 0.706 | 0.889 | | 2.320 |
| Moles | 0.50 | 0.25 | 0.40 | | | 0.25 | |
| Weight (g) | 54.29 | 42.48 | 9.72 | | | 43.01 | |
| Volume (ml) | 49.80 | 28.64 | | 375 | 250 | | |

EXAMPLE 6

In this example, it is shown that the circular dichroism spectrum of A-beta$_{1-42}$ is strongly affected by aluminum, copper, and iron (III), and not by zinc or iron (II). The structure of A-beta$_{1-42}$ peptide is shown in FIG. 1.

The circular dichroic (CD) spectrum of A-beta$_{1-42}$ peptide was measured with a Jasco J-810 Spectropolarimeter. The quartz cuvette has 100 microliter volume and 500 micrometer path length. The settings were a: wavelength range 180-260 nm, sensitivity 100 mdeg, data pitch 0.2 nm, continuous scanning, 50 nm/min, response 1 sec, 2 accumulations. The software was Spectra Manager for Windows, Ver. 1.53.00. The results were saved as TXT files, which are shown graphically in Excel, plotted as degrees of ellipticity vs. wavelength in nm. See FIGS. 31-33.

Beta-amyloid peptide (human amyloid beta-protein 1-42, Aβ$_{1-42}$ or A-beta$_{1-42}$, SynPep) was dissolved in 80% trifluoroethanol (TFE)/20% water at 10 mg/ml to make a stock solution, stored at 4° C. It was diluted to 0.45 mg/ml in TFE for use in the assays. The molecular weight of the peptide was 4513, so 0.45 mg/ml was the equivalent of 100 micromolar. Aluminum, copper, zinc, iron (II), and iron (III) perchlorate (Alfa Aesar) were dissolved at 10 mg/ml in TFE.

Assay conditions: A-beta$_{1-42}$ peptide alone was scanned at the start of each reagent test, then 2-4 microliters aliquots of 10 mM metal perchlorate are added by a 1-10 microliter micropipetter to 100 microliter in the cuvette. Each microliter of metal perchlorate has a molar equivalent of metal to protein. Mixing was believed to be important, and was done with a 100 microliter pipetter. The cuvette was rinsed 3-5 times with 300 microliters of TFE between assays. A-beta$_{1-42}$ peptide in TFE has a large degree of alpha-helix structure, and disruption of this is seen in the CD spectrum as a flattening of the line. Aluminum is the standard of comparison for the metal effects, based on project history. The other metals have been assayed for comparison.

Results: The spectra of A-beta$_{1-42}$ peptide with varying concentrations of metals are shown in FIGS. 31-33. The figure legends indicate the molar equivalents of metals to peptide.

Figure 31A:
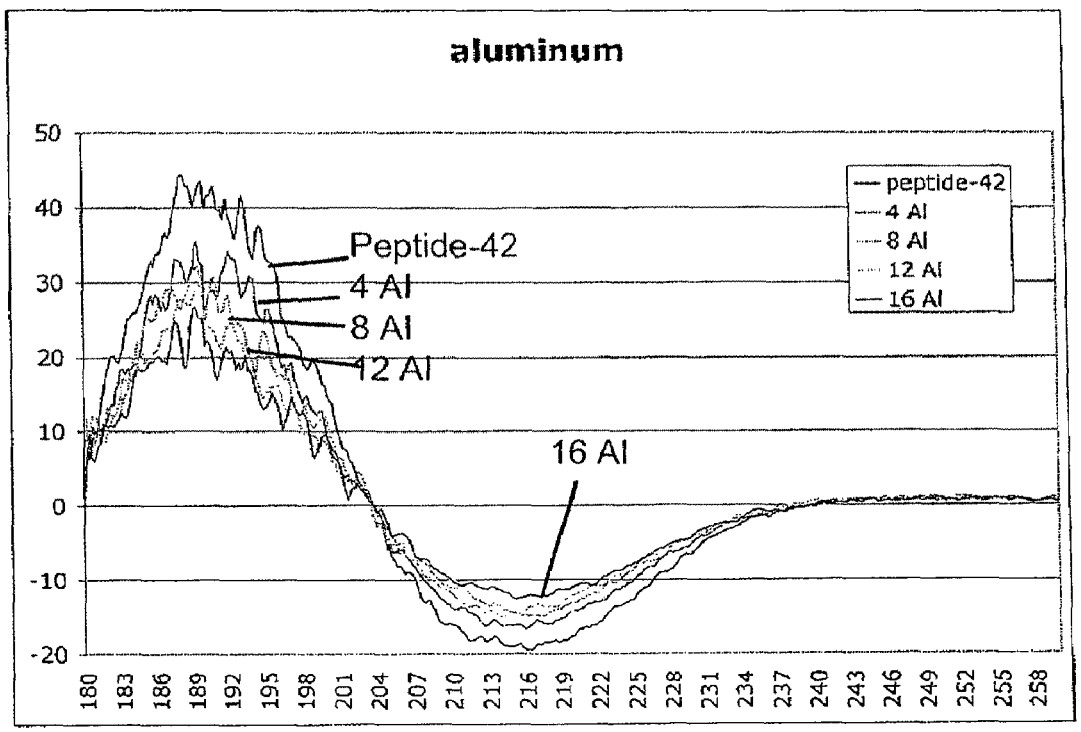
FIGS. 31A-31B graphically provide the CD data illustrating the effect of aluminum and copper on the A-beta$_{1-42}$ structure.
Figure 31B:
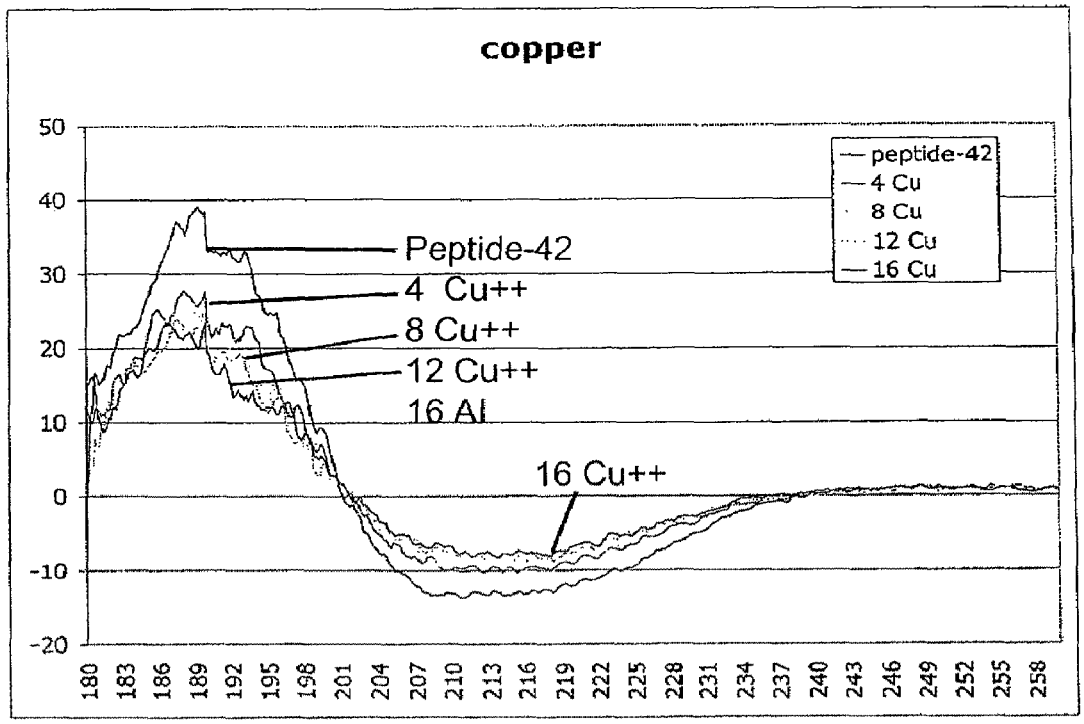

FIGS. 31A and 31B. Aluminum and copper and have similar strong effects on the A-beta$_{1-42}$ spectrum, disrupting the alpha helix.

Figure 32A:
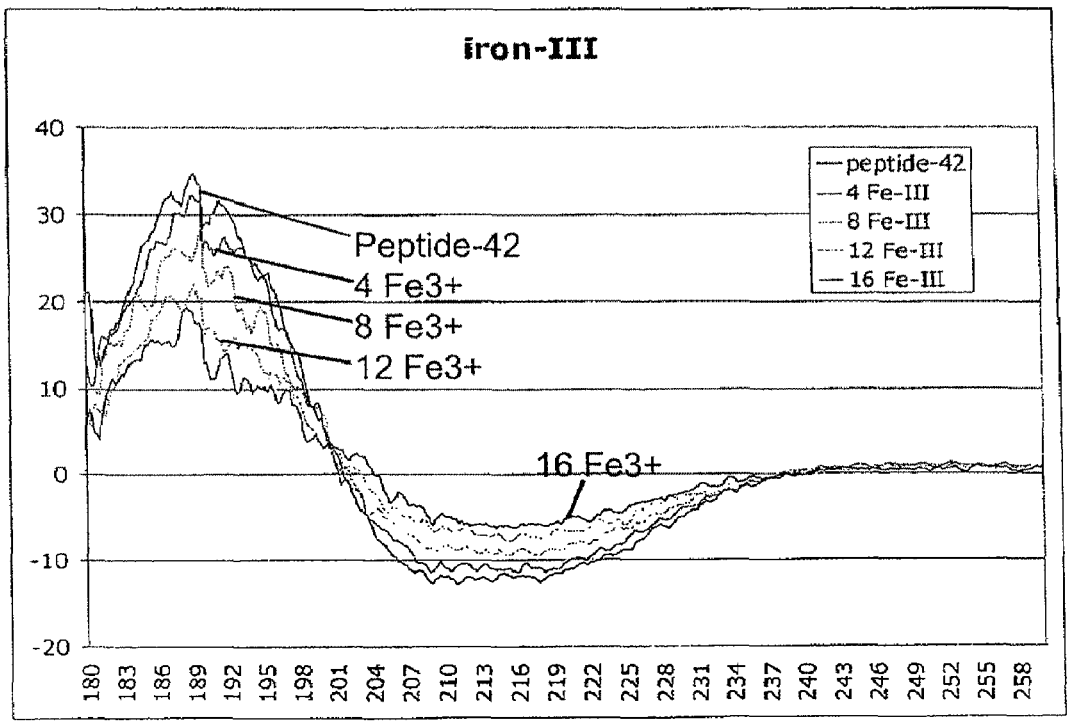
FIGS. 32A-32B graphically provide the CD data illustrating the effect of ferric ion and aluminum ion on the A-beta$_{1-42}$ structure.
Figure 32B:
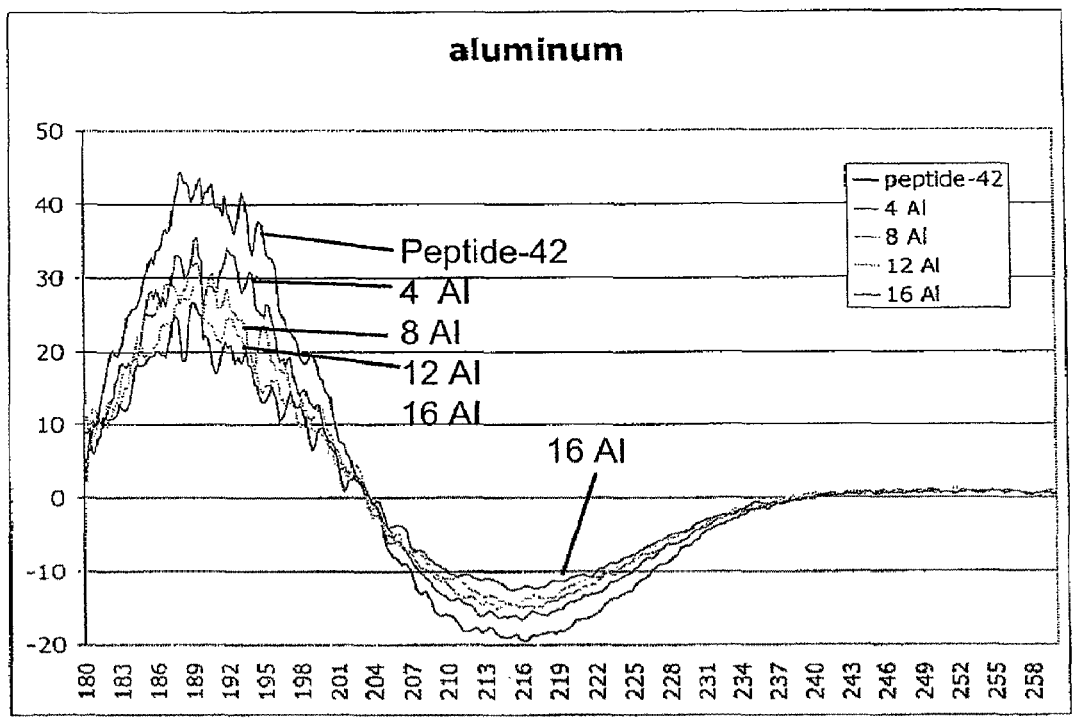

FIGS. 32A and 32B. Aluminum and iron (III) have similar strong effects on the A-beta$_{1-42}$ spectrum, disrupting the alpha helix.

Figure 33A:
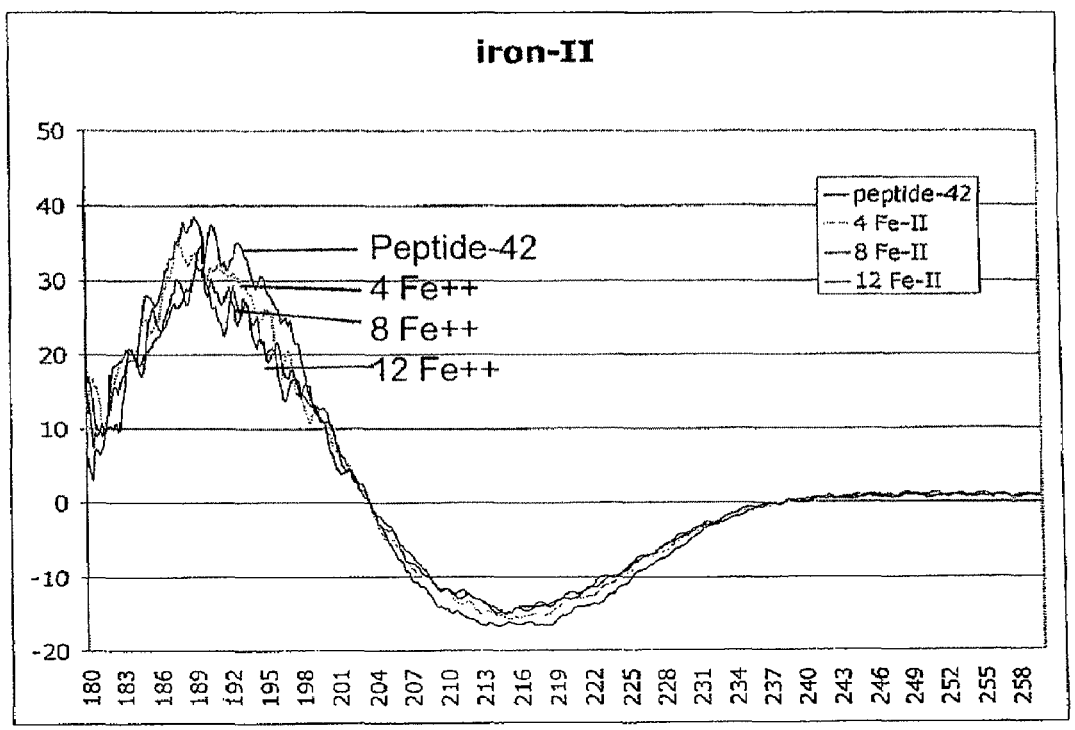
FIGS. 33A-33B graphically provide the CD data illustrating the effect of ferrous ion and zinc ion on the A-beta$_{1-42}$ structure.
Figure 33B:
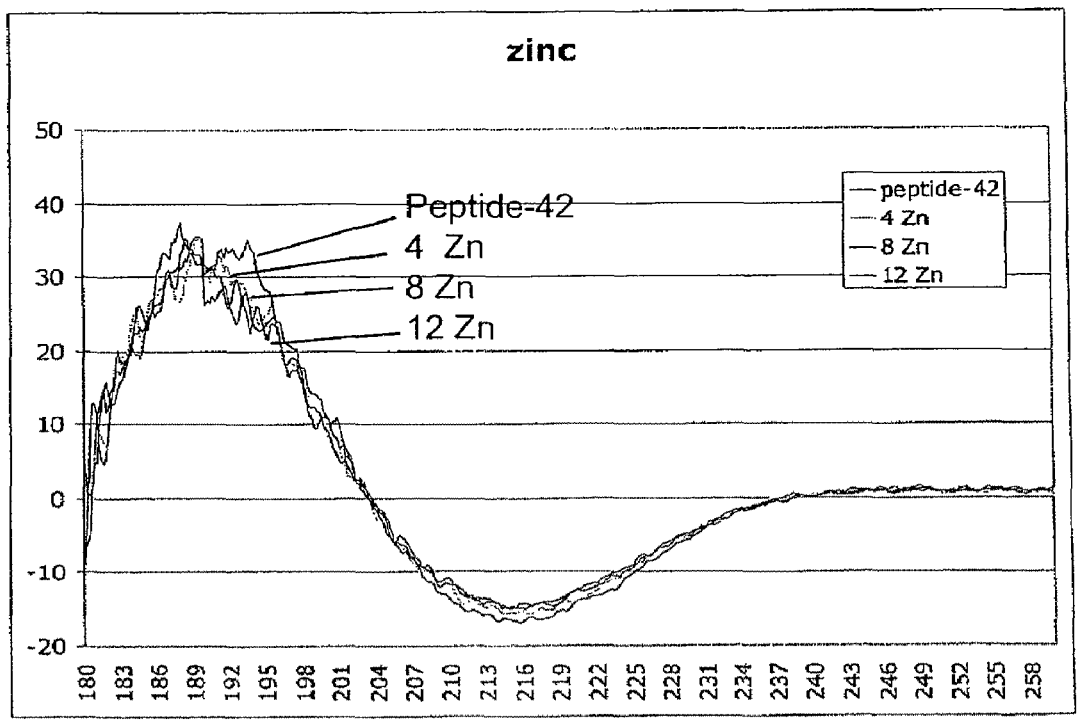

FIGS. 33A and 33B. Zinc and iron (II) have minor or no effects on the spectrum.

Thus, it is believed that compounds of the invention that can chelate or otherwise associate with aluminum, copper, ferrous, or ferric ions are useful in preventing, reducing or reversing the disruption of the protein structure that is a result of the presence of these ions. Specifically, the disruption of A-beta$_{1-42}$ caused by the presence of these ions can be reduced, prevented, or reversed by administering a silicon compound of the invention.

EXAMPLE 7

This example illustrates the permeation of certain silicates of the invention through cultured cell monolayers.

Caco-2 cells are derived from a human colonic adenocarcinoma. This line is often used for epithelial transport studies, including studies modeling transport across the blood-brain barrier. In the present example, the permeation of various silicates of the invention across Caco-2 cell monolayers is illustrated. The silicates 1,2-(methyldichlorosilyl)ethane ("1042"), 2-cyanoethylmethyldichlorosilane ("CEMS"), 2-cyanopropylmethyldichlorosilane ("CPMS" or "DCMSB"), 2-cyanobutylmethyldichlorosilane ("CBMS"), and triethoxysilylbutyronitrile ("TESB") were chosen for this example because they may reverse aluminum-induced denaturation of A-beta$_{1-42}$ (FIG. 1) in circular dichroism assays.

Cell culture. Caco-2 cells were obtained from ATCC and grown in Dulbecco's Modified Eagle's Medium (DMEM), supplemented with 50 microgram/ml gentamicin, and 5% fetal bovine serum. Cells were maintained at 37° C. with 5% CO$_2$.

Caco-2 cells were seeded for experiments onto Transwell inserts (1 cm diameter, polyester, with 0.4 micrometer pores, Corning Costar) in 12-well plates. The medium was changed every 2-4 days. Cells were used for assays when the electrical resistance was over 400 ohm cm$^2$ (Ω cm$^2$).

Sugar permeation. $^3$H-mannitol (NEN) was diluted in medium to a concentration of 2-4.5 microcuries/ml. The medium containing the radiolabeled sugar was added to the apical compartment of each Transwell tested, replacing the culture medium. The plates were incubated at 37° C. After 20, 40 and 60 minutes, the Transwells were moved to new wells containing medium. After 60 minutes, the radioactivity in the apical medium and in the basal medium in each well was measured by scintillation counting.

Silicate permeation. Silicates were dissolved at 10-100 mM in 100 mM HEPES buffer, and brought to approximately neutral pH with NaOH. Then, the silicates were diluted to 20 mM in medium and added to the apical compartment of the Transwell inserts, replacing the culture medium. The plates were incubated as above, and again basal media were sampled at every 20 minutes for a 60 minute interval. The apical medium was also sampled at 60 minutes. The media were analyzed for silicon by Inductively Coupled Plasma Spectrometry (EPA Method 200.7) using an ultrasonic nebulizer, by Industrial Analytical Services, Inc., of Leominster Mass.

Permeation rates. Permeation rates were calculated by the methods of Lohmann et al. (*J. Drug Targeting*, 2002, 10:263-276). The amounts of sugar or silicate accumulated during the three 20 minute intervals were averaged.

The molar fraction cleared was determined as the basal concentration of sugar or silicate divided by the apical concentration, $M_{cleared}=M_{basal}/M_{apical}$; and the volume cleared was determined as the molar fraction cleared times the apical (donor) volume, $V_{cl}=M_{cleared} \times vol$. The permeation surface rate was determined as the volume cleared divided by the time, $PS=V_{cl}/time$; and the permeation coefficient was determined as the permeation surface rate divided by surface area, $P=PS/area$. To subtract out the effects of the filter membranes alone, the calculation used $1/P_{cell}=1/P_{total}-1/P_{filter}$, where $P_{cell}$ is the permeation coefficient through the cells, $P_{total}$ is the measured permeation coefficient, and $P_{filter}$ is the permeation coefficient of the filter membrane (without cells). The results with the silicates demonstrated total permeation. The final units of the permeation coefficient were in distance per time, expressed in cm/sec.

The permeation coefficients are presented in Table 3. It was found that 1,2-(methyldichlorosilyl)ethane and triethoxysilylbutyronitrile permeated Caco-2 cells at rates that were at least four times greater than the permeation of mannitol. Trihydroxysilylmethyl phosphonate has a slower permeation than mannitol. The other compounds appeared to permeate better than mannitol.

TABLE 3

| Compound | Abbreviation(s) | Permeation Coefficient (cm/sec) Mean ± SD, where applicable |
|---|---|---|
| 1,2-(methyldichlorosilyl)ethane | 1042 | $2.5 \times 10^{-5}$ (n = 2) |
| 2-cyanoethylmethyl-dichlorosilane | CEMS | $4.6 \times 10^{-6}$ (n = 2) |
| 2-cyanopropylmethyl-dichlorosilane | CPMS, DCMSB | $6.1 \pm 1.7 \times 10^{-6}$ (n = 4) |
| 2-cyanobutylmethyl-dichlorosilane | CBMS | $6.5 \times 10^{-6}$ (n = 2) |
| triethoxysilylbutyronitrile | TESB | $3.0 \times 10^{-5}$ (n = 2) |
| trihydroxysilylmethyl phosphonate | TSMP | $1.9 \pm 1.5 \times 10^{-7}$ (n = 3) |
| mannitol | | $1.9 \pm 1.9 \times 10^{-6}$ (n = 7) |

It can be concluded that in the Caco-2 model, 1,2-(methyldichlorosilyl)ethane and triethoxysilylbutyronitrile crossed the epithelial barrier efficiently, whereas trihydroxysilylmethyl phosphonate permeated less efficiently. It has been reported the permeation of many compounds across Caco-2 monolayers correlates well with transport across a model of the blood-brain barrier using brain capillary endothelial cells (Lohmann et al., *J. Drug Targeting*, 2002, 10:263-276). These results therefore show that 1,2-(methyldichlorosilyl)ethane and triethoxysilylbutyronitrile may cross the blood-brain barrier. Because it has demonstrated that triethoxysilylbutyronitrile reverses aluminum-induced denaturation of A-beta$_{1-42}$ (see Example 3) this and other silanes may be useful for prevention or treatment of diseases characterized by amyloidosis within the brain, including Alzheimer's disease.

EXAMPLE 8

This example illustrates a western blot assay to quantify A-beta (Aβ) antigen in control and disease brain tissue. Such assays show that certain compositions of the invention are effective in extracting or removing A-beta antigen from the tissue of persons with Alzheimer's disease.

$0.5 \times 2$ cm$^2$ blocks of frozen human hippocampal brain tissue were obtained from the McLean Hospital, Belmont, Mass., including samples of moderate (Braak stage III), moderately severe (Braak stage V), and severe (Braak stage VI) Alzheimer's disease. The blocks were stored at –70° C.

1042 (bis(chlorodimethylsilyl) ethane), CPMS (2-cyanopropylmethyldichlorosilane), CEMS (2-cyanoethylmethyldichlorosilane), and CBMS (2-cyanobutylmethyldichlorosilane) were obtained from Gelest (Morrisville, Pa.). Solutions were made up at 50 or 100 mM in 100 mM MOPS pH 7.0. Control solutions were buffer (100 mM MOPS pH 7.0), EDTA (140 mM NaCl/10 mM EDTA pH 7.0), and acid (140 NaCl/10 mM HCl and 50 mM NaCl/100 mM HCl).

Synthetic Aβ43 peptide was obtained from Biopeptide (San Diego, Calif.) and reconstituted as a 100 nM stock solution in PBS. The stock solution was serially diluted three-fold to a final concentration of 2 nM.

The frozen blocks of brain tissue were serially sectioned on a cryostat. Each 10 micrometer-thick section was collected onto a glass microscope slide. Every tenth slide was fixed in formalin and stained with Congo Red/hematoxyline-eosin. Slides of diseased or non-diseased tissues were stored frozen at –70° C. for further processing.

Prior to treatment, the sections were fixed in absolute ethanol at –20° C. for 7 minutes and rehydrated in phosphate-buffered saline (PBS). The sections on a pair of slides were exposed to experimental solutions by inverting the microscope slide onto glass spacers (fragments of microscope slides) placed on a flat sheet of Parafilm. Control and experimental solutions (0.4 ml) were pipetted between the slide and Parafilm to fill the gap immediately beneath the section and left to incubate at room temperature for 1 h. Care was taken not to allow liquid to touch the glass spacers. The incubation was terminated by recovering the liquid. The combined extract (0.7 ml) was clarified by centrifugation for 3 min in a microfuge and 0.35 ml of the supernatant was diluted 3-fold with 8M urea. The extracted tissue was scraped from the slide with a razor blade into 8M urea and sheared by repeated passages through a narrow gauge (#20) needle. The urea extract was recovered from the supernatant after centrifuging the insoluble material and diluted twenty-fold with 8M urea.

The slot blot assays were performed on the tissue extracts and urea-solubilized tissues. Approximately 300 microliter aliquots from the various dilutions of the experimental, urea extracts or synthetic Aβ$_{1-42}$ or A-beta$_{1-42}$ (FIG. 1) control peptide solution were applied by suction to the well of a slot blot apparatus (BioRad) and adsorbed onto PVDF membrane (0.4 micrometer, Pall Biotrace). On a relative amount basis, a maximum of 1.5% of the urea-extracted tissues and 50% of the supernatants were loaded into the wells. The membrane was blocked for 1 h in 20% Blotto (Pierce) in PBS-Tween (BPT) at 37° C., washed for 5-10 min by agitation in PBS-Tween, incubated with a 1:100 dilution of MAB5206, a mouse monoclonal antibody to $A\beta_{1-42}$ or A-beta$_{1-42}$ (Chemicon) for 1 h at room temperature, washed in BPT, and then incubated with a goat-anti-mouse-HRP (BioRad) at 1:10,000 for 1 h at 37° C. The membrane was washed in PBS and incubated in the LumiGLO chemiluminesence substrate (Upstate) and exposed to film.

Compared with the synthetic peptide calibration curve, all experimental compounds caused antigen to be extracted from Alzheimers tissue. Dilutions of the synthetic peptide showed a log linear relationship between amount loaded in the well and intensity exposed to the film over a range from 0-80 fmol of peptide. The control and experimentally-treated tissues contained similar levels of antigen and the total amount was calculated to be 100 fmol (Table 4).

Figure 34:
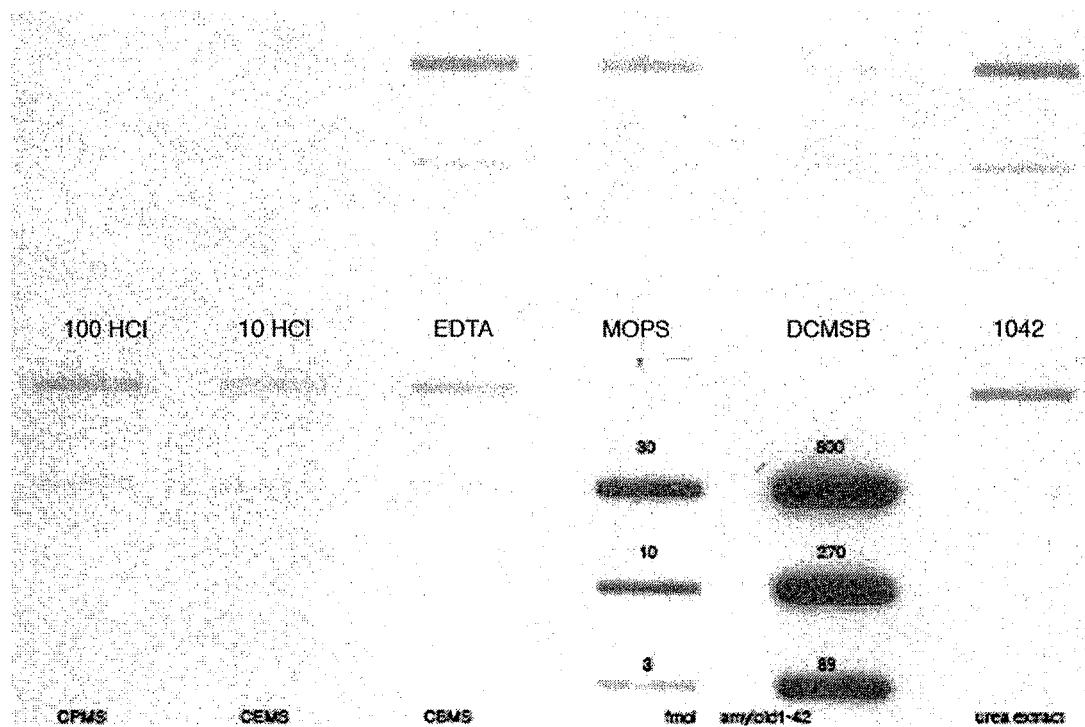
FIG. 34 illustrates a blot of extracts of antigen from tissues treated with various control and experimental solutions of the invention.

On the blots of extracts from the Braak V tissue (FIG. 34), the experimental compounds extracted various amounts of antigen (Table 4). FIG. 34 is a blot of extracted from tissues treated with various control and experimental solutions. Each column represents a dilution series of extracts from the specified solution. Approximately 50% of the diluent was applied to a slot. The lane containing the urea solubilized material (lower right) was loaded with 1.5% of the total volume.

11.2-14.0 fmol of antigen was extracted with the experimental compound 1042 (bis(chlorodimethylsilyl)ethane), EDTA and MOPS. 1.4-6.0 fmol of antigen was detected in extracts from CPMS, CEMS and CBMS. Extracts with HCl or DCMSB contained no detectable antigen. Based on the intensity from urea-solubilized tissues, approximately 12% of the total is released to the extract by exposure to 1042. Treatment with other silicon compounds or control solutions (EDTA or MOPS) released less amount of antigen. The loss of signal from HCl-exposed samples was unexplained.

TABLE 4

| Treatment | Total Extracted (fmol)[1] |
|---|---|
| CPMS | 6.0 |
| CEMS | 1.4 |
| CBMS | 5.2 |
| 1042 | 14.0 |
| EDTA | 11.2 |
| MOPS | 8.2 |
| urea | 112 |

[1]Corrected for volume dilution

EXAMPLE 9

This example illustrates circular dichroism measurements of helix-coil transitions, in accordance with certain embodiments of the invention. Such measurements may be used to demonstrate the ability of certain compositions to prevent and/or reverse loss of the native helical structure of A-beta$_{1-42}$ peptide when exposed to certain metal ions such as aluminum.

Figure 35A:
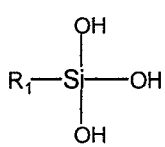
FIGS. 35A-35D illustrate certain compounds of the invention and corresponding CD data.
Figure 35A:
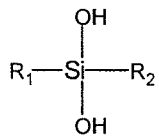
Figure 35A:
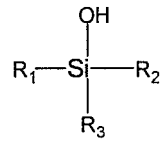
Figure 35B:
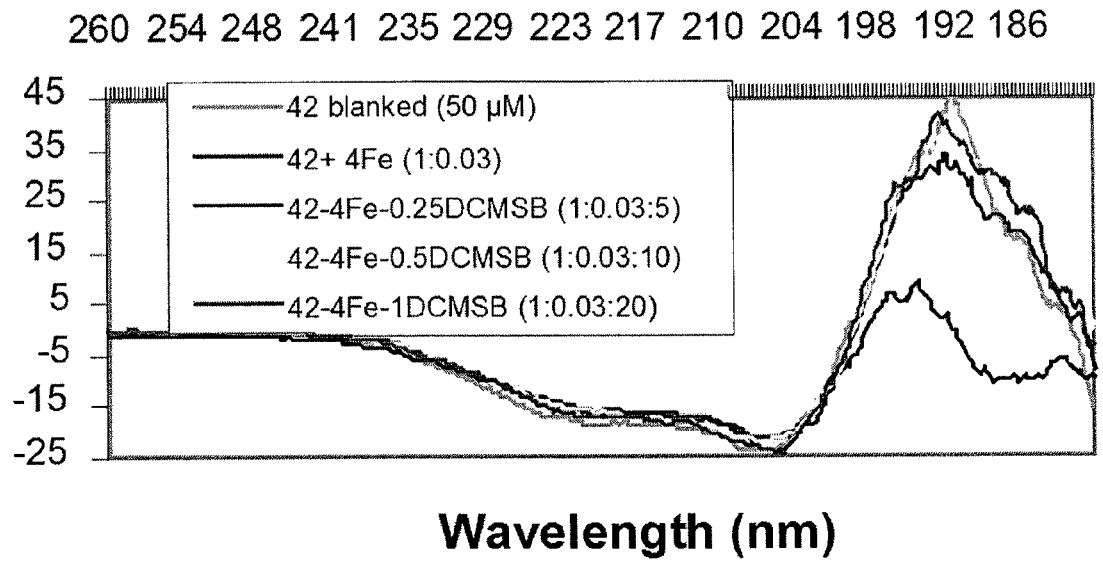
Figure 35C:
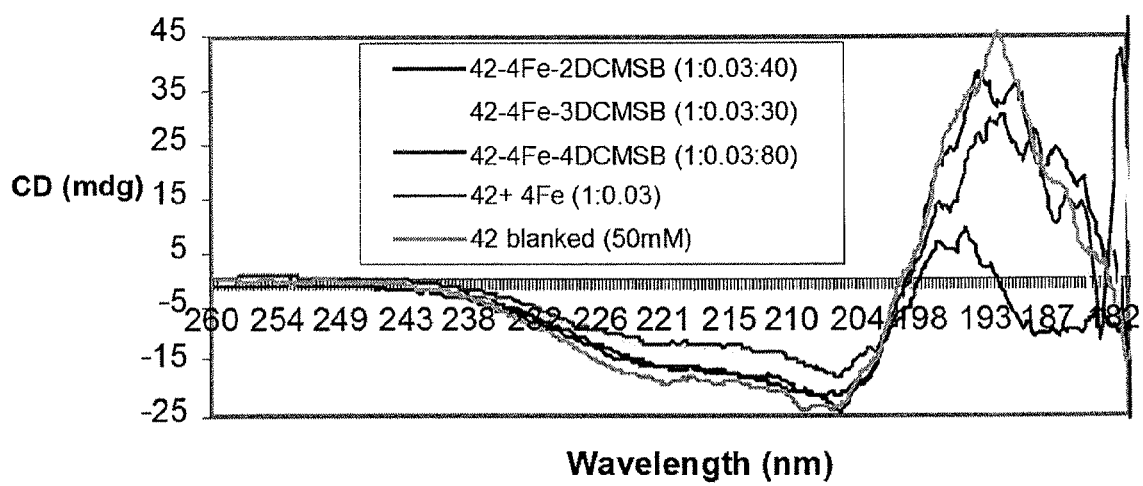
Figure 35D:
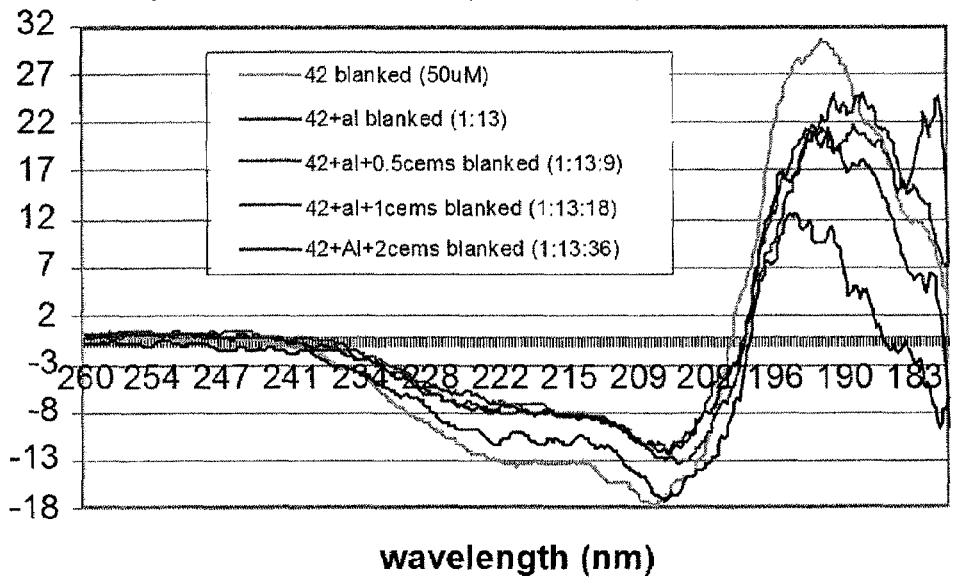

The 42-residue peptide 1 is the C-terminal fragment of human neurofilament, NF-MI7 $A\beta_{1-42}$ or A-beta$_{1-42}$ peptide ($NH_3^+$-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-COO$^-$) (SEQ ID NO. 1) (FIG. 1). This peptide forms alpha-helical structure as measured by circular dichroism (CD) in 2,2,2-trifluoroethanol (TFE) solutions, and the structure of the peptide in TFE has been determined by NMR methods (Sticht, H. et. al., *Eur. J. Biochem.* (1995) 233, 293-298; Crescenzi O. et. al., *Eur. J. Biochem.* (2002) 269, 5642-5648). The addition of a variety of metal salts apparently disrupts the helical structure, resulting in a flattening of the CD curve. The effectiveness of a variety of compounds of type 2-4 at returning the peptide to helical form was determined by the return of the CD curve characteristic of alpha-helical structure (see FIG. 35A for structures).

The following silanetriols 2 or their precursors were tested for solubility and stability of their aqueous solutions: 3-aminopropylsilantriol 2a, 3-(trihydroxysilyl)propylmethylphosphonate sodium salt 2b, n-octyltrihydroxysilane 2c after hydrolysis of the precursor trichlorosilane in water, and 3-cyanopropyltrihydroxysilane 2d, after hydrolysis of the precursor trichlorosilane in water. The following silanediols 3 were tested: diphenylsilanediol 3a, hexylmethyldihydroxysilane 3b, methylphenyldihydroxysilane 3c, dihydroxydiethylsilane 3d, dihydroxydiisopropylsilane 3e, and (dihydroxy)methyl(3-cyanopropyl)silane 3f, all after hydrolysis of their corresponding dichlorosilanes in water. The following monosilanols 4 were also tested: potassium trimethylsilanolate 4a, tert-butyldimethylsilanol 4b, triethylsilanol 4c, and benzyldiethylsilanol 4d. 2a, 3a and 4c were obtained from Gelest, Inc. TFE, 2b, 3e, 3d, 3f, 4b, 4c and 4d were obtained from Sigma-Aldrich (St. Louis, Mo.). 2c and 2d were obtained from Lancaster Synthesis (Windham, N.J.). Compounds obtained as their chlorosilane precursor were hydrolyzed in water and diluted to a final concentration of 20 mM. The precursor for 3d was first dissolved in 50% TFE in water and then made up to a final concentration of 20 mM. Precursor for 3c was first dissolved in 15-50% TFE in water and diluted to final concentration of 20 mM. 3a was first dissolved in dimethyl sulfoxide (DMSO) and then made up to a final concentration of 20 mM in TFE. DMSO blanks (containing no peptide) were collected for each dilution (0.04% to 1%).

The CD titration experiments were performed as follows. Peptide 1 was obtained at greater than 95% purity (Synpep Corp. and Biopeptide Co.). Peptide 1 was dissolved in 2,2,2-trifluoroethanol (TFE) to a concentration of 0.4 mg/ml (0.2 mM). Aluminum perchlorate was prepared as a 20 mM solution in TFE. The sodium metasilicate solution was acidified to pH 6.0. Solutions of organosilanes were prepared by solution in the appropriate buffer, and the pH adjusted appropriately. The solutions were inspected for precipitation and clarity prior to CD analysis.

Circular dichroism spectra were obtained on a Jasco MODEL J-810 CD spectrophotometer from 260-180 m with a 100 millidegree sensitivity. Two accumulations were typically obtained per spectrum. A typical CD titration is described as follows. After temperature equilibration, a background CD spectrum was obtained using 100 microliters of 80% TFE/20% $H_2O$. The reference spectrum was then obtained from 100 microliter of the solution containing peptide 1 (0.23 mg/ml (55 micromolar) of 1 in 80% TFE/20% $H_2O$). The peptide solution was then mixed in a test tube with 8 microliters of 20 mM Fe($ClO_4$)$_3$ solution, mixed thoroughly and transferred back into the CD cell. Aliquots of a 50 mM solution of silane 3f in 100 mM MOPS buffer, pH 7.1 were added in order to reach known molar ratios of peptide, iron, and silane. CD scans were obtained after each additional aliquot of silane was added, until a maximum of 20 equivalents of silane had been added relative to peptide.

The sensitivity of the CD experiment to the helix-coil transition in polypeptides is well-known. The addition of metal ions to peptide 1 results in a significant loss of helicity as detected by the change in the CD spectrum, and may mimic the formation of extended structures typical of amyloid plaques observed as lesions in Alzheimer's disease. Thus, the return of helical structure as measured by CD may reflect a reversal of the processes involved in metal ion-mediated plaque formation. It should be noted that Cl—Si and RO—Si bonds are typically unstable to aqueous environments, hydrolyzing to the HO—Si species. This hydrolysis may be expected to be rapid in the case of halosilanes and somewhat slower and with a greater pH dependence for silyl ethers. It should also be noted that in preparing solutions of these silanes, trisubstituted silanes that hydrolyze to type 2 silanols showed a strong tendency to polymerize and hence may be less well suited for the CD-based assay. The solutions formed by disubstituted silanes (yielding the dihydroxysilanols 3) were in general more stable and less prone to polymerization than the type 2 compounds. Type 4 precursors, while unable to polymerize, were also by and large more hydrophobic and less soluble than type 3.

The results of the titration of the iron-complexed peptide 1 with compound cyanopropylmethyldihydroxysilane 3f are shown in FIG. 35. FIG. 35 shows the CD titration of peptide 1 doped with 4 molar equivalents of $Fe(ClO_4)_3$ with hydroxysilane 3f and 3g The dosage effect is evident, but non-linear, with the first titration point (0.25 eq. of 3f) showing the greatest degree of recovery, and much smaller changes for higher dosages. Similar effects were seen for compound 3g.

Compound 4f showed an efficient combination of stability, solubility, and effectiveness in reversing and/or preventing the effect of metal ion on helix formation. The origin of the significant non-linearity of the effect may be the result of cooperativity in the formation of helical structure.

The mechanism by which this reversal of the helix-coil transition takes place may be due to the presence of metal ions, which may act as a site of nucleation for multidentate ligation by side chains of the peptide, including His, $Glu^-$, $Asp^-$ and Tyr. This metal complex formation may be energetically more stable than helix formation and may result in regions of extended structure possibly involving multiple peptides. One possible mode of action of the silane is to provide (in the case of 4f) a bidentate ligand that is energetically preferred to the complex formed with peptide ligands. Other methods of reversing the metal-induced transition include titration with acid, which presumably protonates the basic side chain functionality involved in metal ligation, making them unable to ligate the metal. Care was taken in any case to control pH during testing, as hydrochloric acid, the product of the hydrolysis of chlorosilanes, is itself effective for reversing the helix-coil transition.

EXAMPLE 10

This example illustrates the protection of endogenous A-beta$_{1-42}$ peptide by pretreatment of the peptide with certain compounds of the invention, prior to exposure to aluminum (III) ions. FIG. 1 illustrates the structure of A-beta$_{1-42}$.

Figure 36A:
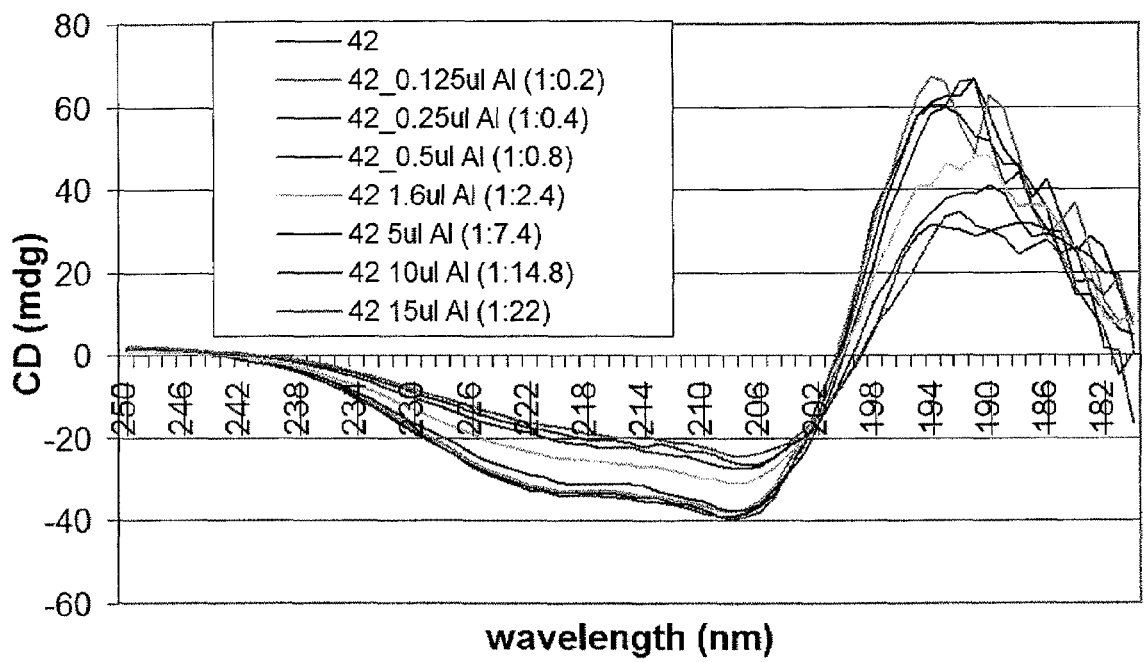
FIGS. 36A-36C illustrate certain CD spectra showing protection against transition metal ion associated loss of native helical conformation using cyanoethylmethyldichlorosilane, in accordance with yet another embodiment of the invention.
Figure 36B:
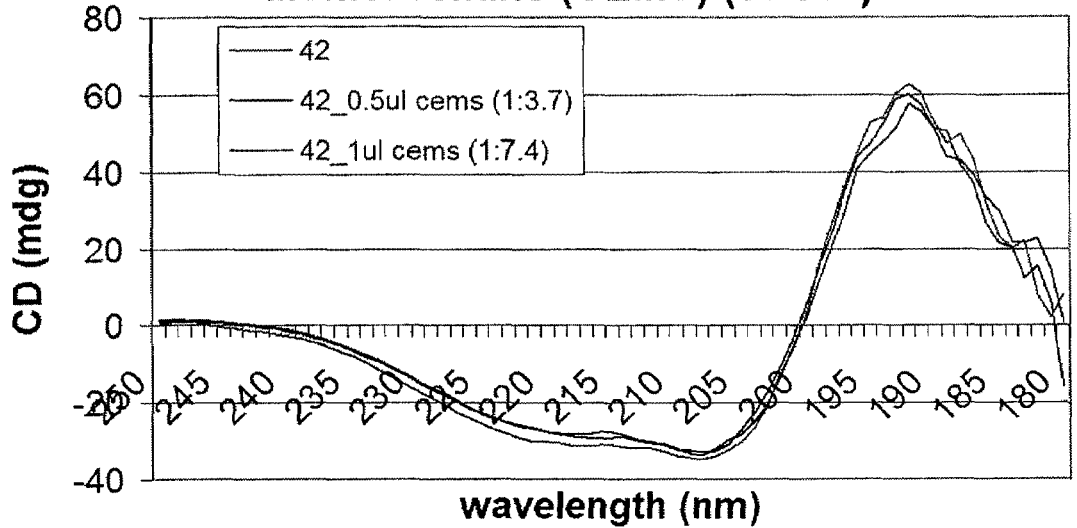
Figure 36C:
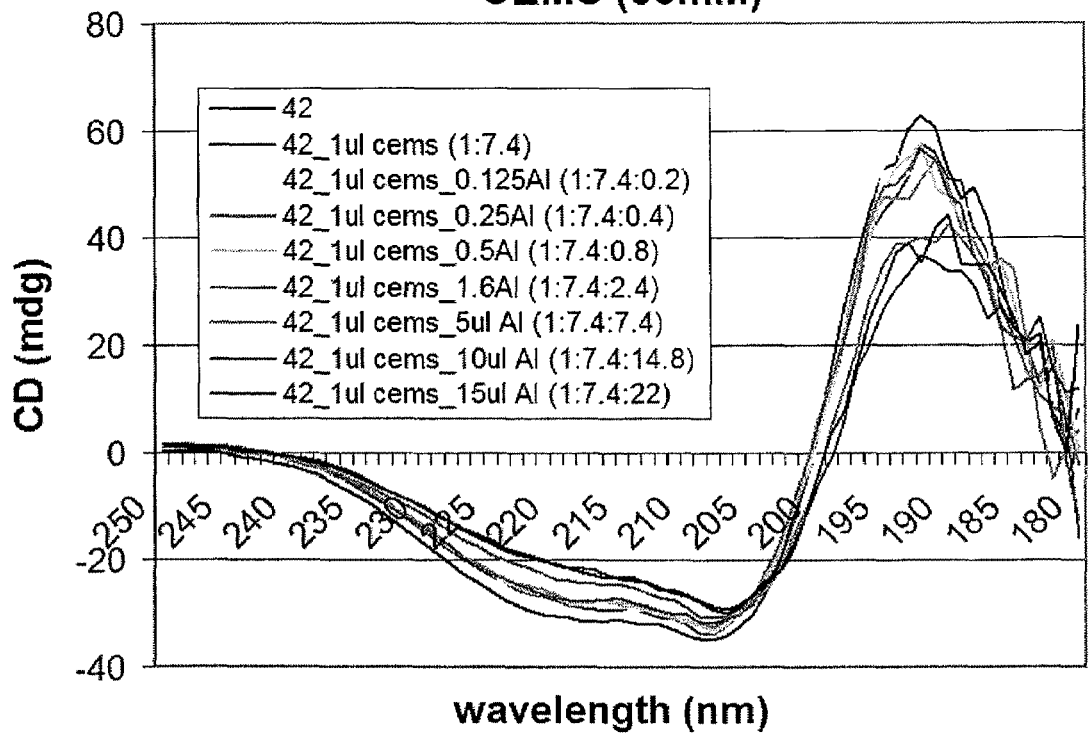

FIGS. 36A-36C are CD spectra that show protection of the helical structure of A-beta$_{1-42}$ peptide by pretreatment with hydrolyzed cyanoethylmethyldichlorosilane against amyloid formation by aluminum (III). Hydrolysis was performed as described in Example 9, and silane was added and buffered as described previously.

FIG. 36A shows decreasing helical structure of A-beta$_{1-42}$ peptide in TFE with increasing amounts of aluminum (III) perchlorate (original concentrations shown on top, molar ratios shown on legend). A relatively smooth decrease in helicity was observed as more aluminum is added.

FIG. 36B shows the pretreatment of A-beta$_{1-42}$ peptide with the hydrolyzed silane, to the point where addition began to perturb the helicity.

Figure 22:
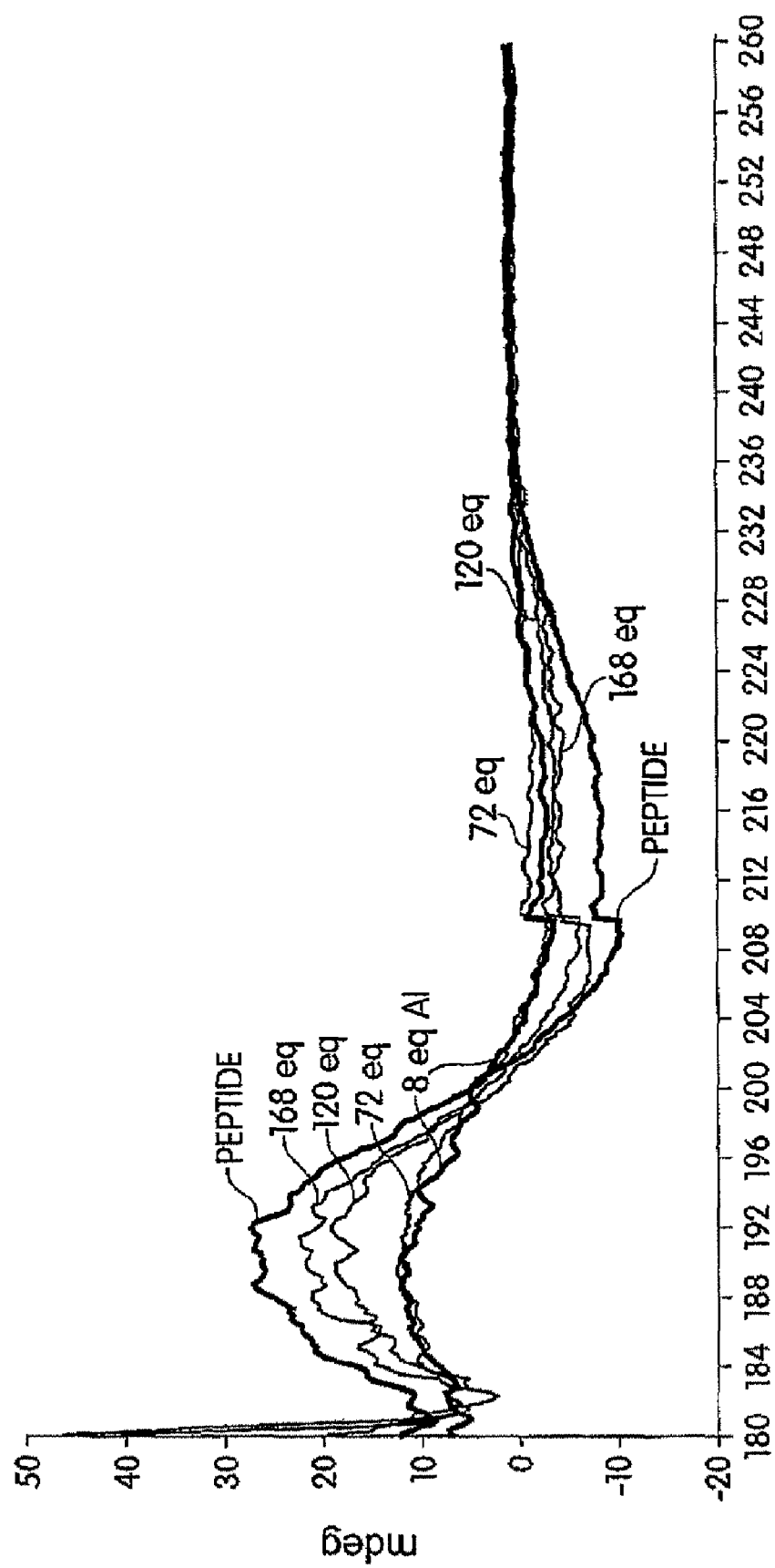
FIG. 22 illustrates the effect of sodium orthosilicate on A-beta$_{1-42}$, as illustrated by CD data.

FIG. 36C shows the same pretreated sample as in FIG. 36B after pretreatment with silane, as aluminum was added. It was noted that the silane appeared to preserve the helicity until about 1 equivalent of Al had been added (equimolar silane and aluminum 7.4:7.4). At that point, the helicity dropped, indicating amyloid formation, eventually to an extent approximately equivalent to that seen with no silane present (FIG. 36C, 22 equivalents of Al).

While several embodiments of the invention have been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

The definitions, as used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for reducing the amount of A-beta antigen in the tissues of a subject having Alzheimer's disease, comprising:
   administering, to the subject, a composition comprising a compound having a structure:

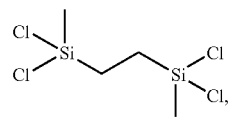

whereby the composition, when administered to a subject, is able to extract or remove A-beta antigen from the tissues of the subject.

2. The method of claim 1, wherein administrating comprises administrating the composition into the brain of the subject.

* * * * *

UNITED STATES PATENT AND TRADEMARK OFFICE
CERTIFICATE OF CORRECTION

| | |
|---|---|
| PATENT NO. | : 7,595,308 B2 |
| APPLICATION NO. | : 11/132170 |
| DATED | : September 29, 2009 |
| INVENTOR(S) | : Friedman et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this

Twenty-eighth Day of September, 2010

David J. Kappos
*Director of the United States Patent and Trademark Office*